United States Patent
Butlin et al.

(10) Patent No.: US 10,273,256 B2
(45) Date of Patent: *Apr. 30, 2019

(54) MACROCYCLES

(71) Applicant: LUMIPHORE, INC., Berkeley, CA (US)

(72) Inventors: Nathaniel G. Butlin, Pacifica, CA (US); Darren Magda, San Leandro, CA (US); Jide Xu, Richmond, CA (US)

(73) Assignee: LUMIPHORE, INC., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/015,911

(22) Filed: Jun. 22, 2018

(65) Prior Publication Data

US 2018/0298040 A1     Oct. 18, 2018

Related U.S. Application Data

(63) Continuation of application No. 15/300,626, filed as application No. PCT/US2015/023818 on Apr. 1, 2015.

(60) Provisional application No. 61/977,301, filed on Apr. 9, 2014.

(51) Int. Cl.
| | | |
|---|---|---|
| *C07F 9/00* | (2006.01) | |
| *C07D 487/08* | (2006.01) | |
| *C07D 259/00* | (2006.01) | |
| *C07D 471/22* | (2006.01) | |
| *G01N 33/60* | (2006.01) | |

(52) U.S. Cl.
CPC ............ *C07F 9/005* (2013.01); *C07D 259/00* (2013.01); *C07D 471/22* (2013.01); *C07D 487/08* (2013.01); *G01N 33/60* (2013.01)

(58) Field of Classification Search
None
See application file for complete search history.

(56) References Cited

U.S. PATENT DOCUMENTS

| | | | |
|---|---|---|---|
| 5,049,280 A | 9/1991 | Raymond et al. | |
| 5,624,901 A | 4/1997 | Raymond et al. | |
| 6,406,297 B1 | 6/2002 | Raymond et al. | |
| 6,515,113 B2 | 2/2003 | Raymond et al. | |
| 6,846,915 B2 | 1/2005 | Raymond et al. | |
| 7,018,850 B2 | 3/2006 | Raymond et al. | |
| 2008/0213780 A1 | 9/2008 | Butlin et al. | |
| 2008/0213917 A1 | 9/2008 | Raymond et al. | |
| 2009/0023928 A1 | 1/2009 | Raymond et al. | |
| 2010/0015725 A1 | 1/2010 | Raymond et al. | |

FOREIGN PATENT DOCUMENTS

| | | |
|---|---|---|
| WO | WO 2008/008797 A1 | 1/2008 |
| WO | WO 2011/025790 A1 | 3/2011 |
| WO | WO 2011/079291 A1 | 6/2011 |
| WO | WO 2014/078690 A1 | 5/2014 |
| WO | WO 2015/157057 A1 | 10/2015 |

OTHER PUBLICATIONS

Berge et al., "Pharmaceutical Salts." Journal of Pharmaceutical Sciences, vol. 66, No. 1 (1977).
Doble et al., "Toward Optimized High-Relaxivity MRI Agents: The Effect of Ligand Basicity on the Thermodynamic Stability of Hexadentate Hydroxypyridonate/Catecholate Gadolinium(III) Complexes." Inorganic Chemistry, vol. 42, No. 16 (2003).
Keana and Cai, "New reagents for photoaffinity labeling: Synthesis and photolysis of functionalized perfluorophenyl azides." The Journal of Organic Chemistry, vol. 55, pp. 3640-3647 (1990).
Moore et al., "Eu(III) Complexes of Functionalized Octadentate 1-Hydroxypyridin-2-ones: Stability, Bioconjugation, and Luminescence Resonance Energy Transfer Studies." Inorganic Chemistry, vol. 49, pp. 9928-9939 (2010).
Petoud et al., "Stable Lanthanide Luminescence Agents Highly Emissive in Aqueous Solution: Multidentate 2-Hydroxyisophthalamide Complexes of $Sm^{3+}$, $Eu^{3+}$, $Tb^{3+}$, $Dy^{3+}$." J. Am. Chem. Soc., vol. 125, pp. 13324-13325 (2003).
Samuel et al., "Water-Soluble 2-Hydroxyisophthalamides for Sensitization of Lanthanide Luminescence." Inorganic Chemistry, vol. 47, No. 17, pp. 7535-7544 (2008).
Xu et al., "Gadolinium(III) 1,2-Hydroxypyridonate-Based Complexes: Toward MRI Contrast Agents of High Relaxivity." Inorganic Chemistry. vol. 43, pp. 5492-5494 (2004).

*Primary Examiner* — James W Rogers
(74) *Attorney, Agent, or Firm* — Morgan, Lewis & Bockius LLP; Jeffry S. Mann

(57) ABSTRACT

The invention relates to chemical compounds and complexes that can be used in therapeutic and diagnostic applications.

24 Claims, 1 Drawing Sheet

MACROCYCLES

CROSS-REFERENCES TO RELATED APPLICATIONS

This application is a Continuation of U.S. application Ser. No. 15/300,626 filed Sep. 29, 2016, which is a 371 National Phase of PCT/US2015/023818 filed Apr. 1, 2015, which claims the benefit under 35 U.S.C. § 119(e) of U.S. Provisional Application No. 61/977,301 filed on Apr. 9, 2014, all of which are incorporated herein by reference in their entireties for all purposes.

STATEMENT REGARDING FEDERALLY SPONSORED RESEARCH OR DEVELOPMENT

This invention was made with Government support under SBIR Phase I grant No. IIP-1215462 awarded by the National Science Foundation. The Government has certain rights in the invention.

FIELD OF THE INVENTION

The invention relates to chemical compounds and complexes that can be used in therapeutic and diagnostic applications.

DESCRIPTION OF EMBODIMENTS

1. Definitions

Figure 1A:
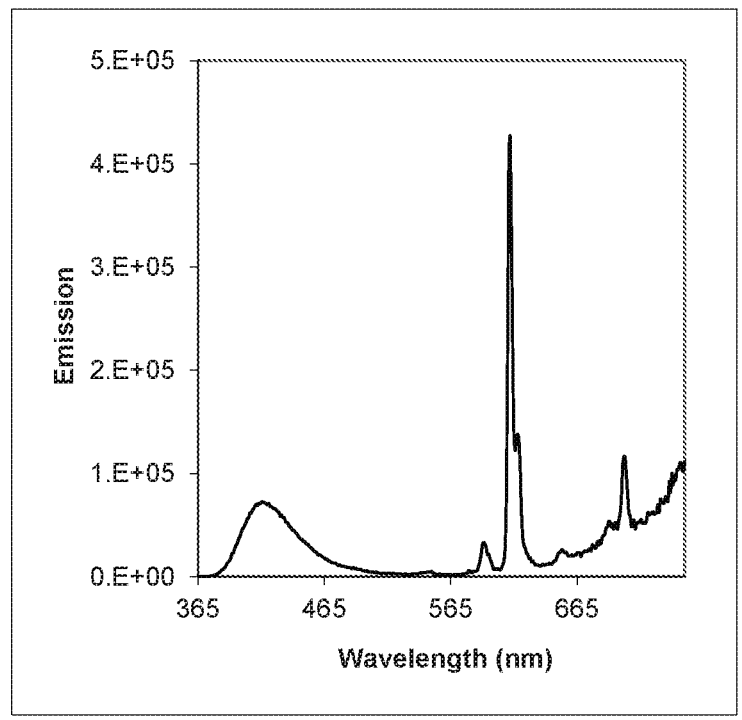
FIG. 1A shows an emission spectrum of bi-macrocyclic chelator 8 with europium(III).

Where substituent groups are specified by their conventional chemical formulae, written from left to right, they optionally equally encompass the chemically identical substituents, which would result from writing the structure from right to left, e.g., —$CH_2$O— is intended to also recite —O$CH_2$—.

The term "alkyl", by itself or as part of another substituent, means a straight or branched chain hydrocarbon, which may be fully saturated, mono- or polyunsaturated and includes mono-, di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl" can refer to "alkylene", which by itself or as part of another substituent means a divalent radical derived from an alkane, as exemplified, but not limited, by —$CH_2CH_2CH_2CH_2$—. Typically, an alkyl (or alkylene) group will have from 1 to 30 carbon atoms. A "lower alkyl" or "lower alkylene" is a shorter chain alkyl or alkylene group, generally having eight or fewer carbon atoms. In some embodiments, alkyl refers to an alkyl or combination of alkyls selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The term "heteroalkyl," by itself or in combination with another term, means an alkyl in which one or more carbons are replaced with one or more heteroatoms selected from the group consisting of O, N, Si and S, (preferably O, N and S), wherein the nitrogen and sulfur atoms may optionally be oxidized and the nitrogen heteroatom may optionally be quaternized. The heteroatoms O, N, Si and S may be placed at any interior position of the heteroalkyl group or at the position at which the alkyl group is attached to the remainder of the molecule. In some embodiments, depending on whether a heteroatom terminates a chain or is in an interior position, the heteroatom may be bonded to one or more H or substituents such as ($C_1$, $C_2$, $C_3$, $C_4$, $C_5$ or $C_6$) alkyl according to the valence of the heteroatom. Examples of heteroalkyl groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. No more than two heteroatoms may be consecutive, as in, for example, —$CH_2$—NH—O$CH_3$ and —$CH_2$—O—Si($CH_3$)$_3$, and in some instances, this may place a limit on the number of heteroatom substitutions. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. The designated number of carbons in heteroforms of alkyl, alkenyl and alkynyl includes the heteroatom count. For example, a ($C_1$, $C_2$, $C_3$, $C_4$, $C_5$ or $C_6$) heteroalkyl will contain, respectively, 1, 2, 3, 4, 5 or 6 atoms selected from C, N, O, Si and S such that the heteroalkyl contains at least one C atom and at least one heteroatom, for example 1-5 C and 1 N or 1-4 C and 2 N. Further, a heteroalkyl may also contain one or more carbonyl groups. In some embodiments, a heteroalkyl is any $C_2$-$C_{30}$ alkyl, $C_2$-$C_{25}$ alkyl, $C_2$-$C_{20}$ alkyl, $C_2$-$C_{15}$ alkyl, $C_2$-$C_{10}$ alkyl or $C_2$-$C_6$ alkyl in any of which one or more carbons are replaced by one or more heteroatoms selected from O, N, Si and S (or from O, N and S). In some embodiments, each of 1, 2, 3, 4 or 5 carbons is replaced with a heteroatom. The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

The terms "cycloalkyl" and "heterocycloalkyl", by themselves or in combination with other terms, refer to cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means a polyunsaturated, aromatic substituent that can be a single ring or optionally multiple rings (preferably 1, 2 or 3 rings) that are fused together or linked covalently. In some embodiments, aryl is a 3, 4, 5, 6, 7 or 8 membered ring, which is optionally fused to one or two other 3, 4, 5, 6, 7 or 8 membered rings. The term "heteroaryl" refers to aryl groups (or rings) that contain 1, 2, 3 or 4 heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

In some embodiments, any of alkyl, heteroalkyl, cycloalkyl, heterocycloalkyl, aryl and heteroaryl is optionally substituted. That is, in some embodiments, any of these groups is substituted or unsubstituted. In some embodiments, substituents for each type of radical are selected from those provided below.

Substituents for the alkyl, heteroalkyl, cycloalkyl and heterocycloalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents". In some embodiments, an alkyl group substituent is selected from -halogen, —OR', =O, =NR', =N—OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. In one embodiment, R', R", R''' and R"" are each independently selected from hydrogen, alkyl (e.g., $C_1$, $C_2$, $C_3$, $C_4$, $C_5$ and $C_6$ alkyl). In one embodiment, R', R", R''' and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. In one embodiment, R', R", R''' and R"" are each independently selected from hydrogen, alkyl, heteroalkyl, cycloalkyl, heterocycloalkyl, aryl, heteroaryl, alkoxy, thioalkoxy groups, and arylalkyl. When R' and R" are attached to the same nitrogen atom, they can be combined with the nitrogen atom to form a 5-, 6-, or 7-membered ring. For example, —NR'R" can include 1-pyrrolidinyl and 4-morpholinyl. In some embodiments, an alkyl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Similar to the substituents described for the alkyl radical, substituents for the aryl and heteroaryl groups are generically referred to as "aryl group substituents". In some embodiments, an aryl group substituent is selected from -halogen, —OR', =O, =NR', =N—OR', —NR'R", —SR', —SiR'R"R''', —OC(O)R', —C(O)R', —CO$_2$R', —CONR'R", —OC(O)NR'R", —NR"C(O)R', —NR'—C(O)NR"R''' —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system. In some embodiments, R', R", R''' and R"" are independently selected from hydrogen and alkyl (e.g., $C_1$, $C_2$, $C_3$, $C_4$, $C_5$ and $C_6$ alkyl). In some embodiments, R', R", R''' and R"" are independently selected from hydrogen, substituted or unsubstituted alkyl, substituted or unsubstituted heteroalkyl, substituted or unsubstituted aryl and substituted or unsubstituted heteroaryl. In some embodiments, R', R", R''' and R"" are independently selected from hydrogen, alkyl, heteroalkyl, aryl and heteroaryl. In some embodiments, an aryl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl.

The term "acyl" refers to a species that includes the moiety —C(O)R, where R has the meaning defined herein. Exemplary species for R include H, halogen, substituted or unsubstituted alkyl, substituted or unsubstituted aryl, substituted or unsubstituted heteroaryl, and substituted or unsubstituted heterocycloalkyl. In some embodiments, R is selected from H and ($C_1$-$C_6$)alkyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. In some embodiments, halogen refers to an atom selected from F, Cl and Br.

The term "heteroatom" includes oxygen (O), nitrogen (N), sulfur (S) and silicon (Si). In some embodiments, a heteroatom is selected from N and S. In some embodiments, the heteroatom is O.

Unless otherwise specified, the symbol "R" is a general abbreviation that represents a substituent group that is selected from acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound includes more than one R, R', R", R'" and R"" group, they are each independently selected.

For groups with solvent exchangeable protons, the ionized form is equally contemplated. For example, —COOH also refers to —COO— and —OH also refers to —O⁻.

Any of the compounds disclosed herein can be made into a pharmaceutically acceptable salt. The term "pharmaceutically acceptable salts" includes salts of compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides any of the compounds disclosed herein in a prodrug form. Prodrugs of the compounds described herein are those compounds that readily undergo chemical changes under physiological conditions to provide the compounds of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. For example, the compounds may be labeled with deuterium ($^2$H) or radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The symbol , displayed perpendicular to a bond, indicates the point at which the displayed moiety is attached to the remainder of the molecule.

In some embodiments, the definition of terms used herein is according to IUPAC.

2. Compositions

The invention provides numerous chelators and metal ion complexes thereof. Generally, a chelator comprises a plurality of chelating agents that are linked together by way of two or more scaffold moieties. Chelating moieties bound together by two scaffold moieties such that at least one closed ring is formed can be referred to as closed chelators, macrocycles or macrocyclic chelators.

There are several factors to be considered in the design for an alpha chelating agent for anticancer therapy. Some of the key issues apart from the kinetics will be the high affinity for the target metal (such as Th) which at the same time needs to have a low exchange rate for other biologically significant metal ions. So, in our ligand design, the electronic properties of the target metal and ligand are considered and matched. The chelate should also be able to assume the appropriate coordination cavity size and geometry for the desired metal. In this case, Th, an actinide ion, is a "hard" cation and has a large charge-to-radius ratio. Hence, Th prefers "hard" electron donors and negatively charged oxygen donors. A coordination number of 8 or greater is generally preferred by actinide ions as they have a tendency to form stable complexes with ligands of high denticity; however, the selectivity towards the binding of the thorium will be determined by our design of the chelating unit. The effective but nonselective amino-carboxylic acid ligands such as DTPA can deplete essential biological metal ions from patients, thus causing serious health problems. Selecting the correct type of chelating unit, therefore, is an important factor in achieving high selectivity toward the specific metal ion.

A chelator can comprise numerous chelating moieties. Particularly useful chelators contain a number of chelating moieties sufficient to provide, for example, 6, 8 or 10 heteroatoms such as oxygen that coordinate with a metal ion to form a complex. The heteroatoms such as oxygen provide electron density for forming coordinate bonds with a positively charged ion, and such heteroatoms can thus be considered "donors". In some embodiments, the plurality of chelating moieties of a chelator comprises a plurality of oxygen donors and a metal ion (such as a radionuclide) is chelated to the chelator via at least one of the oxygen donors. In some embodiments, a chelator comprises a plurality of oxygen donors and a metal ion (such as a radionuclide) is chelated to the chelator via a plurality or all of the oxygen donors.

2.1. Macrocycles

In one aspect, the invention provides a macrocycle of formula (M2+) or (M3+):

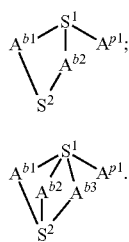

(M2+)

(M3+)

wherein $S^1$ and $S^2$ are independently selected scaffold moieties.

$A^{b1}$, $A^{b2}$, $A^{b3}$, and $A^{p1}$ are independently selected chelating moieties.

Scaffold moieties and chelating moieties are as defined herein.

Any of the combinations of $S^1$, $S^2$, $A^{b1}$, $A^{b2}$, $A^{b3}$, and $A^{p1}$ are encompassed by this disclosure and specifically provided by the invention.

In some embodiments, the macrocycle comprises a linker. In some embodiments, the linker is attached to a targeting moiety. In some embodiments, the macrocycle comprises a targeting moiety.

In some embodiments, the macrocycle comprises one or more additional, pendant chelating moieties ($A^{px}$), which may be attached to $S^1$, $S^2$, or $A^{p1}$. Chelating moieties are as defined herein.

In some embodiments, the macrocycle comprises one, two or more modifying moieties. The modifying moieties can be the same or different.

2.1.1. Chelating Moieties $A^{b1}$, $A^{b2}$, $A^{b3}$, and $A^{p1}$ are chelating moieties having a structure independently selected from:

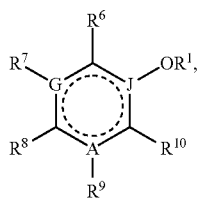

(I)

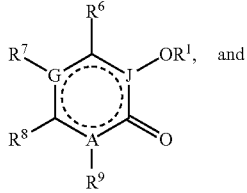

(II)

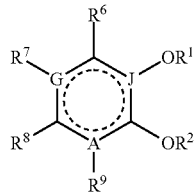

(III)

wherein
A and G are independently selected from carbon, nitrogen and oxygen;

wherein when A is oxygen, $R^9$ is not present; and when G is oxygen, $R^7$ is not present;

J is selected from carbon and nitrogen;

each $R^1$ and $R^2$ are independently selected from H, an enzymatically labile group, a hydrolytically labile group, a metabolically labile group, a photolytically labile group and a single negative charge;

each $R^6$, $R^7$, $R^8$, $R^9$, and $R^{10}$ are independently selected from a bond to $S^1$ or $S^2$, alkanediyl attached to S or $S^2$, H, substituted or unsubstituted alkyl, substituted or unsubstituted heteroalkyl, halogen, CN, —$CF_3$, —$C(O)R^{17}$, —$SO_2NR^{17}R^{18}$, —$NR^{17}R^{18}$, —$OR^{17}$, —$S(O)_2R^{17}$, —$COOR^{17}$, —$S(O)_2OR^{17}$, —$OC(O)R^{17}$, —$C(O)NR^{17}R^{18}$, —$NR^{17}C(O)R^{18}$, —$NR^{17}SO_2R^{18}$, and —$NO_2$, wherein at least two of $R^6$, $R^7$, $R^8$, $R^9$, and $R^{10}$ are optionally joined to form a ring system selected from substituted or unsubstituted cycloalkyl, substituted or unsubstituted heterocycloalkyl, substituted or unsubstituted aryl and substituted or unsubstituted heteroaryl;

$R^{17}$ and $R^{18}$ are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and $R^{17}$ and $R^{18}$, together with the atoms to which they are attached, are optionally joined to form a 5-, 6- or 7-membered ring;

wherein $A^{b1}$, $A^{b2}$, and $A^{b3}$ are each attached to $S^1$ and $S^2$ through two members selected from $R^6$, $R^7$, $R^8$, $R^9$, and $R^{10}$; and $A^{p1}$ is attached to $S^1$ through a member selected from $R^6$, $R^7$, $R^8$, $R^9$, and $R^{10}$.

In some embodiments, when any of $A^{b1}$, $A^{b2}$, and $A^{b3}$ has a structure according to formula (I), the respective chelating moiety is attached to $S^1$ and $S^2$ through $R^6$ and $R^{10}$. In some embodiments, when any of $A^{b1}$, $A^{b2}$, and $A^{b3}$ has a structure according to formula (II) or (III), the respective chelating moiety is attached to $S^1$ and $S^2$ through $R^6$ and $R^9$.

In some embodiments, when $A^{p1}$ has a structure according to formula (I), $A^{p1}$ is attached to $S^1$ through $R^6$ or $R^{10}$.

In some embodiments, when $A^{p1}$ has a structure according to formula (II) or (III), $A^{p1}$ is attached to $S^1$ through $R^6$ or $R^9$.

In some embodiments, at least one of $R^6$ and $R^{10}$ in (I) is a bond attached to $S^1$ or $S^2$.

In some embodiments, $A^{b1}$, $A^{b2}$, $A^{b3}$, and $A^{p1}$ are chelating moieties having a structure independently selected from:

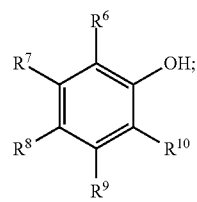

(1)

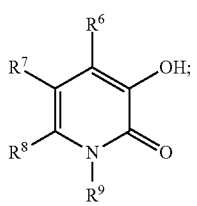

(2a)

-continued

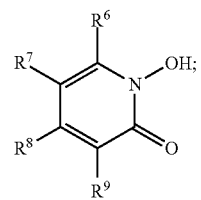
(2b)

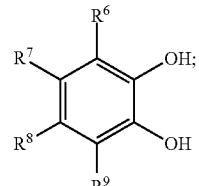
(3)

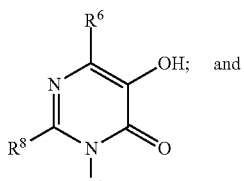
(4)

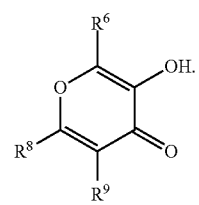
(5)

$R^6$, $R^7$, $R^8$, $R^9$, and $R^{10}$ are as defined herein.

In some embodiments, $A^{b1}$, $A^{b2}$, $A^{b3}$, and $A^{p1}$ are chelating moieties having a structure independently selected from:

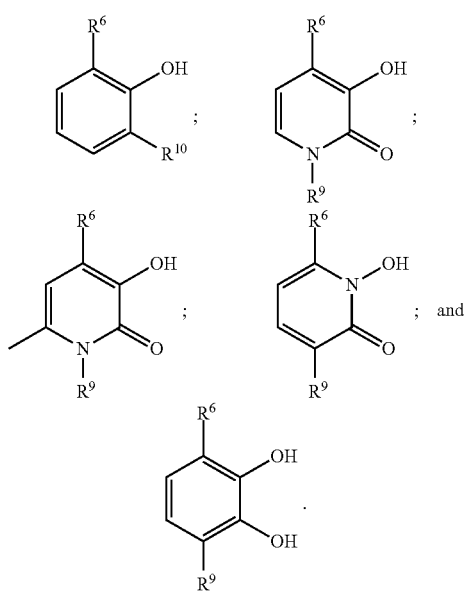

$R^6$, $R^9$, and $R^{10}$ are as defined herein.

In some embodiments, $A^{b1}$ and $A^{b2}$ in formula (M2+) are the same. In some embodiments, $A^{b1}$, $A^{b2}$, and $A^{b3}$ in formula (M3+) are the same.

In some embodiments, at least one of $A^{b1}$, $A^{b2}$, and $A^{b3}$ does not have the structure:

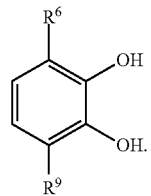

In some embodiments, $A^{b1}$, $A^{b2}$, and $A^{b3}$ do not have the structure:

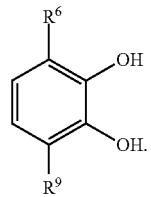

In some embodiments, $A^{p1}$ comprises a linker. In some embodiments, the linker is attached to a targeting moiety. In some embodiments, $A^{p1}$ comprises a targeting moiety. In some embodiments, $R^6$, $R^7$, $R^8$, $R^9$, or $R^{10}$ of $A^{p1}$ comprises a linker. In some embodiments, $R^6$, $R^7$, $R^8$, $R^9$, or $R^{10}$ of $A^{p1}$ is a linker.

In some embodiments, $R^6$, $R^7$, $R^8$, $R^9$, or $R^{10}$ of $A^{p1}$ is —C(O)NR$^{17}$R$^{18}$, wherein $R^{17}$ or $R^{18}$ comprises a linker. In some embodiments, $R^6$, $R^7$, $R^8$, $R^9$, or $R^{10}$ of $A^{p1}$ is —C(O)NR$^{17}$R$^{18}$, wherein $R^{17}$ is H and $R^{18}$ comprises a linker. In some embodiments, $R^6$, $R^7$, $R^8$, $R^9$, or $R^{10}$ of $A^{p1}$ is —C(O)NR$^{17}$R$^{18}$, wherein $R^{17}$ is H and $R^{18}$ is a linker.

In some embodiments, when $A^{p1}$ has a structure according to formula (I) or (1), $A^{p1}$ is attached to $S^1$ through $R^6$, and $R^{10}$ comprises a linker.

In some embodiments, when $A^{p1}$ has a structure according to formula (I) or (1), $A^{p1}$ is attached to $S^1$ through $R^{10}$, and $R^6$ comprises a linker.

In some embodiments, when $A^{p1}$ has a structure according to formula (II), (III), (2a), (2b), (3), (4), or (5), $A^{p1}$ is attached to $S^1$ through $R^6$, and $R^9$ comprises a linker.

In some embodiments, when $A^{p1}$ has a structure according to formula (II), (III), (2a), (2b), (3), (4), or (5), $A^{p1}$ is attached to $S^1$ through $R^9$, and $R^6$ comprises a linker.

Linkers are as defined herein.

In some embodiments, $A^{p1}$ comprises a modifying moiety. In some embodiments, $R^6$, $R^7$, $R^8$, $R^9$, or $R^{10}$ of $A^{p1}$ comprises a modifying moiety. In some embodiments, $R^6$, $R^7$, $R^8$, $R^9$, or $R^{10}$ of $A^{p1}$ is a modifying moiety.

In some embodiments, $R^6$, $R^7$, $R^8$, $R^9$, or $R^{10}$ of $A^{p1}$ is —C(O)NR$^{17}$R$^{18}$, wherein $R^{17}$ or $R^1$ comprises a modifying moiety. In some embodiments, $R^6$, $R^7$, $R^8$, $R^9$, or $R^{10}$ of $A^{p1}$ is —C(O)NR$^{17}$R$^{18}$, wherein $R^{17}$ is H and $R^{18}$ comprises a modifying moiety. In some embodiments, $R^6$, $R^7$, $R^8$, $R^9$, or $R^{10}$ of $A^{p1}$ is —C(O)NR$^{17}$R$^{18}$, wherein $R^{17}$ is H and $R^{18}$ is a modifying moiety.

In some embodiments, when $A^{p1}$ has a structure according to formula (I) or (1), $A^{p1}$ is attached to $S^1$ through $R^6$, and $R^{10}$ comprises a modifying moiety.

In some embodiments, when $A^{p1}$ has a structure according to formula (I) or (1), $A^{p1}$ is attached to $S^1$ through $R^{10}$, and $R^6$ comprises a modifying moiety.

In some embodiments, when $A^{p1}$ has a structure according to formula (II), (III), (2a), (2b), (3), (4), or (5), $A^{p1}$ is attached to $S^1$ through $R^6$, and $R^9$ comprises a modifying moiety. In some embodiments, when $A^{p1}$ has a structure according to formula (II), (III), (2a), (2b), (3), (4), or (5), $A^{p1}$ is attached to $S^1$ through $R^9$, and $R^6$ comprises a modifying moiety. Modifying moieties are as defined herein.

2.1.2. Scaffold Moieties

A "scaffold moiety" is any moiety useful for covalently linking two or more chelating moieties in any of the chelators (macrocycles) disclosed herein. In exemplary embodiments, any two scaffold moieties disclosed herein are joined via a plurality of chelating moieties to form a macrocycle. In exemplary embodiments, one or more scaffold moieties of a chelator is substituted with a linker. In one embodiment, the scaffold moiety is selected from substituted or unsubstituted alkyl and substituted or unsubstituted heteroalkyl. Exemplary scaffold moieties include linear or branched ethers and amines. In some embodiments, the linker is attached to a targeting moiety. In some embodiments, the scaffold moiety comprises a targeting moiety.

Other exemplary scaffold moieties include, but are not limited to:

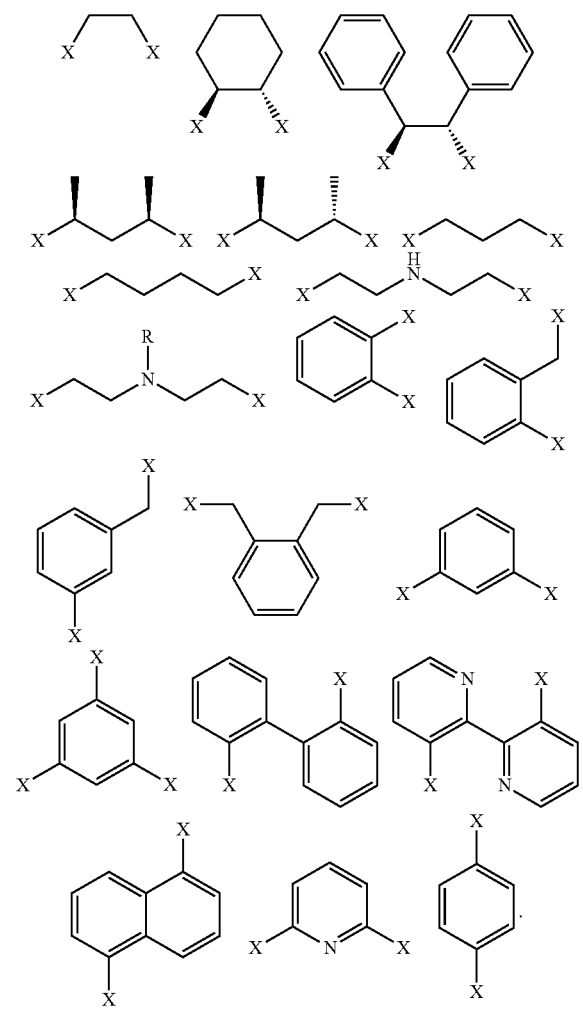

"X" represents a locus of attachment for a chelating moiety, and in exemplary embodiments includes a heteroatom such as nitrogen. Thus, in some embodiments, X is NR'R", wherein R' and R" are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, halogen, CN, $CF_3$, $-C(O)R^{17}$, $-SO_2NR^{17}R^{18}$, $-NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, $-NO_2$; and $R^{17}$ and $R^{18}$ are each independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; wherein at least one R' or R" comprises a bond to a chelating moiety. The chelating moiety can be attached to a scaffold via any appropriate linker.

In some embodiments, a scaffold moiety is linear. One exemplary scaffold moiety is $X-(CH_2)_3-X-(CH_2)_4-X-(CH_2)_3-X$, which is preferably substituted (e.g. with a linker) at at least one of the alkyl moieties. That is, one exemplary scaffold moiety is spermine based. Other exemplary scaffold moieties include

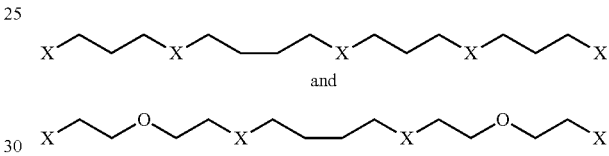

and any of which is preferably substituted (e.g. with a linker) at at least one of the alkyl moieties. X is as given in the previous paragraph.

One preferred moiety for at least one of the X moieties is the 1,2-HOPO amide moiety, but those of skill in the art will appreciate that other chelating moieties in any used in any combination. In each of the scaffold structures, an aryl moiety or alkyl moiety can be substituted with one or more "aryl group substituent" or "alkyl group substituent" as defined herein.

A particularly useful scaffold moiety for any chelator described herein has the structure

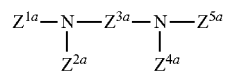

wherein $Z^{1a}$, $Z^{2a}$, $Z^{3a}$, $Z^{4a}$ and $Z^{5a}$ are selected from substituted or unsubstituted alkyl and substituted or unsubstituted heteroalkyl; and $Z^{1a}$, $Z^{2a}$, $Z^{4a}$ and $Z^{5a}$ comprise a bond to one of the chelating moieties.

In some embodiments, $Z^{3a}$ is substituted or unsubstituted ($C_1$, $C_2$, $C_3$, $C_4$, $C_5$ or $C_6$) alkyl. In some embodiments, $Z^{3a}$ is substituted or unsubstituted $-(CH_2)_m(CH_2CH_2O)_n-(CH_2)_p-$, wherein m, n and p are integers independently selected from 1, 2, 3, 4, 5 and 6. In some embodiments, $Z^{3a}$ is ethyl. In some embodiments, $Z^{3a}$ is ethyl substituted with =O.

In some embodiments, $Z^{1a}$, $Z^{2a}$, $Z^{4a}$ and $Z^{5a}$ have a structure selected from $Z'R^{20a}N(H)C(O)Z''$, $Z'R^{20a}N(H)C(O)R^{21a}Z''$ and $Z'R^{21a}Z''$ wherein Z' is a bond to the second scaffold moiety, Z" is a bond to one of the plurality of chelating moieties, $R^{20a}$ is selected from substituted or unsubstituted alkyl and substituted or unsubstituted heteroalkyl, and $R^{21a}$ is selected from substituted or unsubstituted alkyl and substituted or unsubstituted heteroalkyl. In some embodiments, $R^{20a}$ is selected from substituted or unsubstituted ($C_1$, $C_2$, $C_3$, $C_4$, $C_5$ or $C_6$) alkyl and substituted or unsubstituted ($C_1$, $C_2$, $C_3$, $C_4$, $C_5$ or $C_6$) heteroalkyl. In some embodiments, $R^{20a}$ is selected from substituted or unsubstituted ethyl. In some embodiments, $R^{21a}$ is from substituted or unsubstituted —$(CH_2)_wO$— wherein w is selected from 1, 2, 3, 4, 5 and 6. In exemplary embodiments, w is 1 or 3.

In some embodiments, at least one of $Z^{1a}$, $Z^{2a}$, $Z^{3a}$, $Z^{4a}$ and $Z^{5a}$ is substituted with a linker.

Another particularly useful scaffold moiety for any chelator herein has the structure

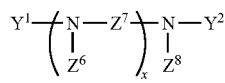

x is selected from 1, 2, 3 and 4. In exemplary embodiments, x is 1. In exemplary embodiments, x is 2. In exemplary embodiments, x is 3. In exemplary embodiments, x is 4.

$Y^1$ and $Y^2$ are each independently selected from H, substituted or unsubstituted alkyl and substituted or unsubstituted heteroalkyl. In exemplary embodiments, $Y^1$ and $Y^2$ are H.

$Z^7$ is selected from substituted or unsubstituted alkyl and substituted or unsubstituted heteroalkyl. In exemplary embodiments, at least one $Z^7$ is substituted with a linker. In some embodiments, each $Z^7$ is independently substituted or unsubstituted ($C_1$, $C_2$, $C_3$, $C_4$, $C_5$ or $C_6$) alkyl. In exemplary embodiments, each $Z^7$ is independently substituted or unsubstituted propyl or butyl. In some embodiments, each $Z^7$ is independently substituted or unsubstituted heteroalkyl.

In exemplary embodiments, each $Z^7$ is independently substituted or unsubstituted —$(CH_2)_m(CH_2CH_2O)_n$-$(CH_2)_p$—, wherein m, n and p are integers independently selected from 1, 2, 3, 4, 5 and 6. In exemplary embodiments, each $Z^7$ is substituted or unsubstituted —$(CH_2)_2O(CH_2)_2$—.

$Z^6$ and $Z^8$ are independently selected from —C(O)—, substituted or unsubstituted alkyl, and substituted or unsubstituted heteroalkyl; and each of $Z^6$ and $Z^8$ comprises a bond to one of the chelating moieties.

In exemplary embodiments, $Z^6$ and $Z^8$ are —C(O)—.

Another useful scaffold moiety has the structure:

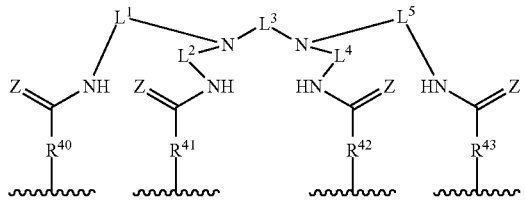

in which each Z is independently selected from O and S. In some embodiments, $L^3$ comprises —$(CH_2CH_2O)_mR^{31}$— wherein m is an integer selected from 0, 1, 2, 3, 4, 5, 6, 7, 8 and 9. In some embodiments, m is 0. In some embodiments, m is 1. In some embodiments, $L^3$ is —$CH_2CH_2OCH_2CH_2$—. $L^1$, $L^2$, $L^4$, $L^5$ and $R^{31}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In exemplary embodiments, $L^1$, $L^2$, $L^4$, $L^5$ are independently selected substituted or unsubstituted ($C_1$, $C_2$, $C_3$, $C_4$, $C_5$ or $C_6$) alkyl. In some embodiments, $R^{31}$ is substituted or unsubstituted ($C_1$, $C_2$, $C_3$, $C_4$, $C_5$ or $C_6$) alkyl. In exemplary embodiments, $L^1$, $L^2$, $L^4$, $L^5$ are independently selected substituted or unsubstituted ethyl. In some embodiments, $R^{31}$ is substituted or unsubstituted ethyl. In exemplary embodiments, $L^1$, $L^2$, $L^4$, $L^5$ are ethyl, one or more of which is substituted with a linker. In some embodiments, $L^1$ is substituted with a linker. In some embodiments, $L^2$ is substituted with a linker. In some embodiments, $L^3$ is substituted with a linker. In some embodiments, $L^4$ is substituted with a linker. In some embodiments, $L^5$ is substituted with a linker. In some embodiments, $L^1$ is ethyl substituted with a linker. In some embodiments, $L^2$ is ethyl substituted with a linker. In some embodiments, $L^3$ is ethyl substituted with a linker. In some embodiments, $L^4$ is ethyl substituted with a linker. In some embodiments, $L^5$ is ethyl substituted with a linker. In some embodiments, $R^{40}$, $R^{41}$, $R^{42}$ and $R^{43}$ are bonds. In some embodiments, $R^{40}$, $R^{41}$, $R^{42}$ and $R^{43}$ are —$(CH_2)_wO$—, wherein w is selected from 0, 1, 2, 3, 4, 5, 6, 7, 8, 9 and 10. In exemplary embodiments, w is 3.

Another useful scaffold has the structure

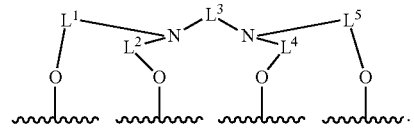

In some embodiments, $L^3$ comprises —$(CH_2CH_2O)_mR^{31}$— wherein m is an integer selected from 0, 1, 2, 3, 4, 5, 6, 7, 8 and 9. In some embodiments, m is 0. In some embodiments, m is 1. In some embodiments, $L^3$ is —$CH_2CH_2OCH_2CH_2$—. In some embodiments, $L^3$ is —$C(O)C(O)$—. $L^1$, $L^2$, $L^4$, $L^5$ and $R^{31}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In exemplary embodiments, $L^1$, $L^2$, $L^4$, $L^5$ are independently selected substituted or unsubstituted ($C_1$, $C_2$, $C_3$, $C_4$, $C_5$ or $C_6$) alkyl. In exemplary embodiments, $R^{31}$ is substituted or unsubstituted ($C_1$, $C_2$, $C_3$, $C_4$, $C_5$ or $C_6$) alkyl. In exemplary embodiments, $L^1$, $L^2$, $L^4$, $L^5$ are independently selected substituted or unsubstituted ethyl. In exemplary embodiments, $L^1$, $L^2$, $L^4$, $L^5$ are independently selected substituted or unsubstituted propyl. In some embodiments, $R^{31}$ is substituted or unsubstituted ethyl. In exemplary embodiments, $L^1$, $L^2$, $L^4$, $L^5$ are ethyl, one or more of which is substituted with a linker. In some embodiments, $L^1$ is substituted with a linker. In some embodiments, $L^2$ is substituted with a linker. In some embodiments, $L^3$ is substituted with a linker. In some embodiments, $L^4$ is substituted with a linker. In some embodiments, $L^5$ is substituted with a linker. In some embodiments, $L^1$ is propyl substituted with a linker. In some embodiments, $L^2$ is propyl substituted with a linker. In some embodiments, $L^3$ is propyl substituted with a linker. In some embodiments, $L^4$ is propyl substituted with a linker. In some embodiments, $L^5$ is propyl substituted with a linker.

In some embodiments, a scaffold is selected from:

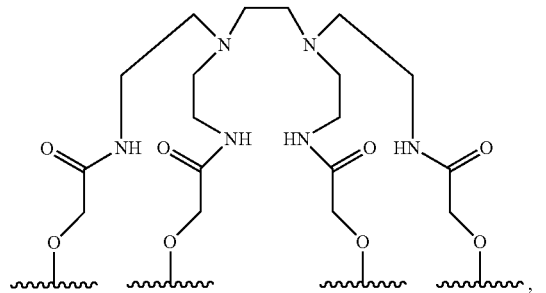

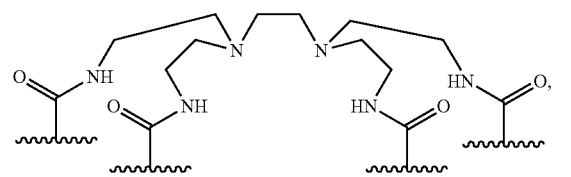

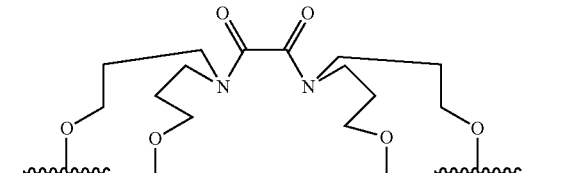

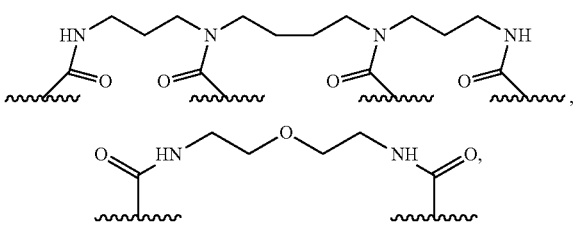

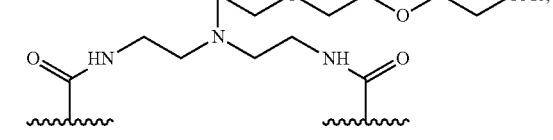

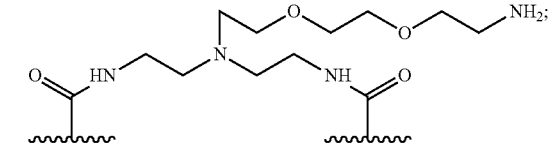

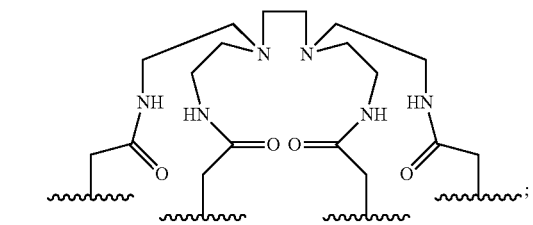

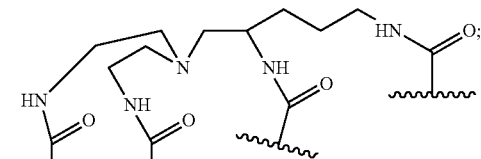

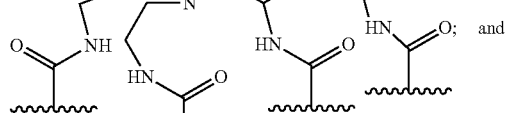

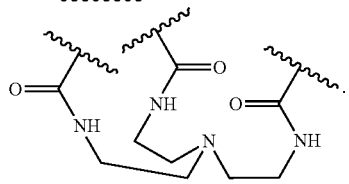

In any of these structures, one or more methyl, ethyl, propyl or butyl moieties can be substituted with one or more linkers. In some embodiments, two of these scaffold moieties, in which one or more methyl, ethyl, propyl or butyl moieties are optionally substituted with one or more linkers, are used to form a macrocycle.

In some embodiments, $S^1$, $S^2$, or both comprise a linker. In some embodiments, $S^1$ comprises a linker. In some embodiments, $S^2$ comprises a linker. In some embodiments, the linker is attached to a targeting moiety. In some embodiments, $S^1$, $S^2$, or both comprise a targeting moiety. In some embodiments, $S^1$ comprises a targeting moiety. In some embodiments, $S^2$ comprises a targeting moiety.

$S^1$

In some embodiments, $S^1$ has the structure:

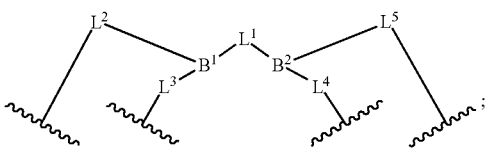

wherein $L^1$, $L^2$, $L^3$, $L^4$, and $L^5$ are independently selected from substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, $L^1$, $L^2$, $L^3$, $L^4$, and $L^5$ are independently selected from substituted or unsubstituted alkyl and substituted or unsubstituted heteroalkyl. In some embodiments, $L^1$, $L^2$, $L^3$, $L^4$, and $L^5$ are independently selected from substituted or unsubstituted $C_1$-$C_6$ alkyl and substituted or unsubstituted $C_1$-$C_6$ heteroalkyl.

In some embodiments, $A^{p1}$ is attached to $L^5$, and $L^5$ comprises a cleavable bond, allowing $A^{p1}$ to be cleaved from the macrocycle under appropriate conditions (for instance, by an enzyme). In some embodiments, the cleavable bond is an enzymatically cleavable bond, a hydrolytically cleavable bond, a metabolically cleavable bond, or a photolytically cleavable bond. In some embodiments, the cleavable bond is part of a peptide, oligonucleotide, or DNA.

In some embodiments, one of $L^5$ and $L^1$ is substituted with a linker. In some embodiments, $L^5$ is substituted with a linker. Linkers are as defined herein.

$B^1$ and $B^2$ are independently selected from the elements capable of 3, 4, or 5 covalent bonds. In some embodiments, $B^1$ and $B^2$ are independently selected from N, C, B, Si, and P. In some embodiments, $B^1$ and $B^2$ are independently selected from N and C. In some embodiments, $B^1$ and $B^2$ are N.

In some embodiments, $S^1$ has the structure:

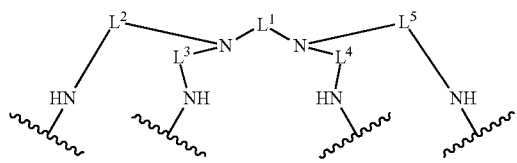

wherein $L^1$, $L^2$, $L^3$, $L^4$, and $L^5$ are as defined herein.

In some embodiments, S has the structure:

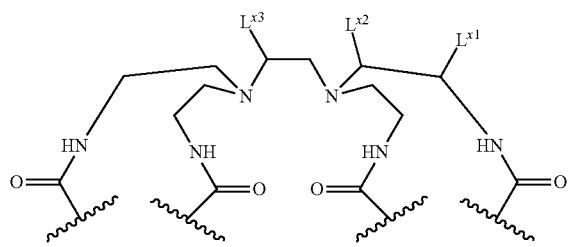

wherein $L^{x1}$, $L^{x2}$ and $L^{x3}$ are independently selected from H and a linker. In some embodiments, only one of $L^{x1}$, $L^{x2}$ and $L^{x3}$ is a linker. In some embodiments, $L^{x1}$ is a linker. Linkers are as defined herein. In some embodiments, $L^{x1}$, $L^{x2}$ and $L^{x3}$ are H.

In some embodiments, $S^1$ has the structure:

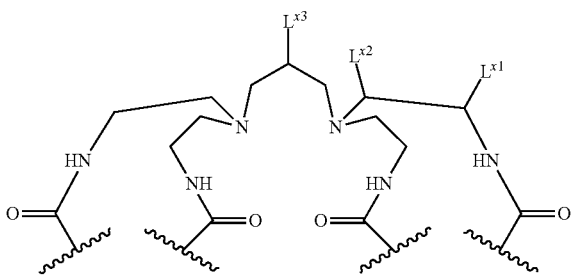

wherein $L^{x1}$, $L^{x2}$ and $L^{x3}$ are independently selected from H and a linker. In some embodiments, only one of $L^{x1}$, $L^{x2}$ and $L^{x3}$ is a linker. In some embodiments, $L^{x3}$ is a linker. Linkers are as defined herein. In some embodiments, $L^{x1}$, $L^{x2}$ and $L^{x3}$ are H.

In some embodiments, $S^1$ has the structure:

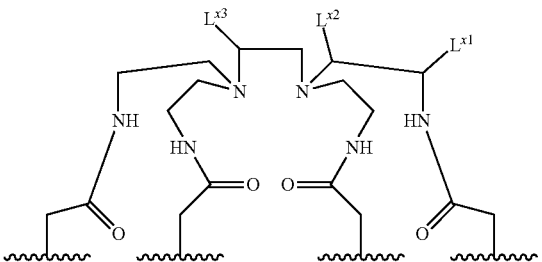

wherein $L^{x1}$, $L^{x2}$ and $L^{x3}$ are independently selected from H and a linker. In some embodiments, only one of $L^{x1}$, $L^{x2}$ and $L^{x3}$ is a linker. In some embodiments, $L^{x1}$ is a linker. Linkers are as defined herein. In some embodiments, $L^{x1}$, $L^{x2}$ and $L^{x3}$ are H.

In some embodiments, $S^1$ has the structure:

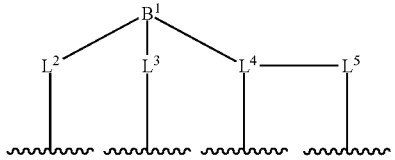

wherein $B^1$, $L^2$, $L^3$, $L^4$, and $L^5$ are as defined herein.

In some embodiments, one of $L^2$, $L^3$, $L^4$, and $L^5$ is substituted with a linker. In some embodiments, $L^2$ is substituted with a linker. In some embodiments, $L^5$ is substituted with a linker. Linkers are as defined herein.

In some embodiments, S has the structure:

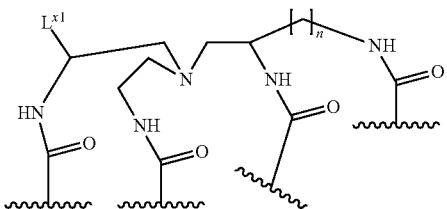

wherein n is 1, 2, 3, 4, 5, or 6; and $L^{x1}$ is H or a linker.

In some embodiments, $S^1$ has the structure:

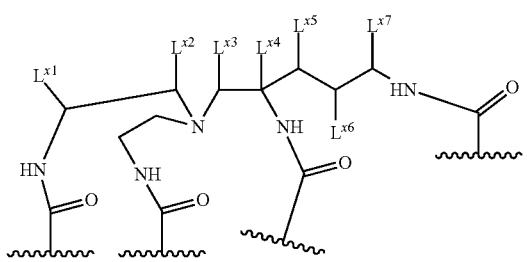

wherein $L^{x1}$, $L^{x2}$, $L^{x3}$, $L^{x4}$, $L^{x5}$, $L^{x6}$, and $L^{x7}$ are independently selected from H and a linker. In some embodiments, only one of $L^{x1}$, $L^{x2}$, $L^{x3}$, $L^{x4}$, $L^{x5}$, $L^{x6}$, and $L^{x7}$ is a linker. In some embodiments, $L^{x1}$ is a linker. Linkers are as defined herein. In some embodiments, $L^{x1}$, $L^{x2}$, $L^{x3}$, $L^{x4}$, $L^{x5}$, $L^{x6}$, and $L^{x7}$ are H.

In some embodiments, $S^1$ has the structure:

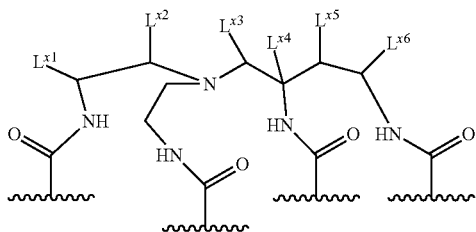

wherein $L^{x1}$, $L^{x2}$, $L^{x3}$, $L^{x4}$, $L^{x5}$, and $L^{x6}$ are independently selected from H and a linker. In some embodiments, only one of $L^{x1}$, $L^{x2}$, $L^{x3}$, $L^{x4}$, $L^{x5}$, and $L^{x6}$ is a linker. In some embodiments, $L^{x1}$ is a linker. Linkers are as defined herein. In some embodiments, $L^{x1}$, $L^{x2}$, $L^{x3}$, $L^{x4}$, $L^{x5}$, and $L^{x6}$ are H.

In some embodiments, $S^1$ has the structure:

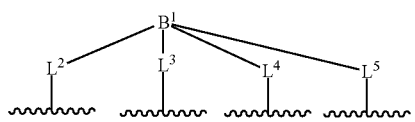

wherein $B^1$, $L^2$, $L^3$, $L^4$, and $L^5$ are as defined herein.

In some embodiments, one of $L^2$, $L^3$, $L^4$, and $L^5$ is substituted with a linker. In some embodiments, $L^2$ is substituted with a linker. In some embodiments, $L^5$ is substituted with a linker. Linkers are as defined herein.

In some embodiments, $S^1$ has the structure:

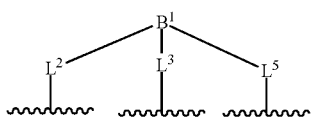

wherein $B^1$, $L^2$, $L^3$, and $L^5$ are as defined herein.

In some embodiments, one of $L^2$, $L^3$, and $L^5$ is substituted with a linker. In some embodiments, $L^2$ is substituted with a linker. In some embodiments, $L^5$ is substituted with a linker. Linkers are as defined herein.

In some embodiments, $S^1$ has the structure:

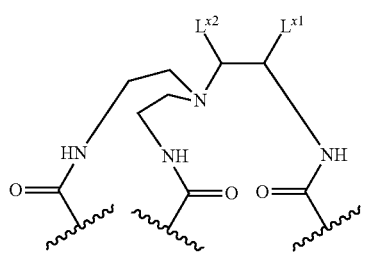

wherein $L^{x1}$ and $L^{x2}$ are independently selected from H and a linker. In some embodiments, only one of $L^{x1}$ and $L^{x2}$ is a linker. In some embodiments, $L^{x1}$ is a linker. Linkers are as defined herein. In some embodiments, $L^{x1}$ and $L^{x2}$ are H.

$S^2$

In some embodiments, $S^2$ has the structure:

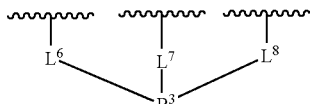

wherein $L^6$, $L^7$, and $L^8$ are independently selected from substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, $L^6$, $L^7$, and $L^8$ are independently selected from substituted or unsubstituted alkyl and substituted or unsubstituted heteroalkyl. In some embodiments, $L^6$, $L^7$, and $L^8$ are independently selected from substituted or unsubstituted $C_1$-$C_6$ alkyl and substituted or unsubstituted $C_1$-$C_6$ heteroalkyl. In some embodiments, one of $L^6$, $L^7$, and $L^8$ is substituted with a linker. Linkers are as defined herein. $B^3$ is selected from the elements capable of 3, 4, or 5 covalent bonds. In some embodiments, $B^3$ is selected from N, C, B, Si, and P. In some embodiments, $B^3$ is selected from N and C. In some embodiments, $B^3$ is N.

In some embodiments, $S^2$ has the structure:

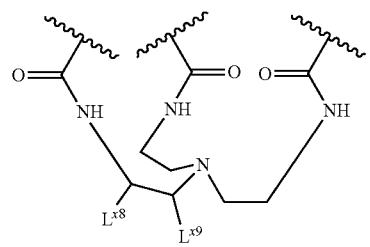

wherein $L^{x8}$ and $L^{x9}$ are independently selected from H and a linker. In some embodiments, only one of $L^{x8}$ and $L^{x9}$ is a linker. In some embodiments, $L^{x8}$ is a linker. Linkers are as defined herein. In some embodiments, $L^{x8}$ and $L^{x9}$ are H.

In some embodiments, $S^2$ has the structure:

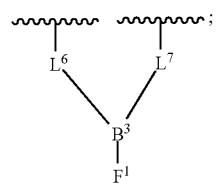

wherein $L^6$ and $L^7$ are independently selected from substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, $L^6$ and $L^7$ are independently selected from substituted or unsubstituted alkyl and substituted or unsubstituted heteroalkyl. In some embodiments, $L^6$ and $L^7$ are independently selected from substituted or unsubstituted $C_1$-$C_6$ alkyl and substituted or unsubstituted $C_1$-$C_6$ heteroalkyl. In some embodiments, one of $L^6$ and $L^7$ is substituted with a linker. Linkers are as defined herein. $B^3$ is as defined herein.

$F^1$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, $F^1$ is as defined herein.

In some embodiment $S^2$ has the structure:

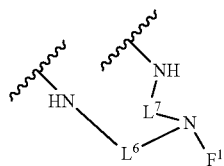

wherein $L^6$, $L^7$ and $F^1$ are as defined herein.

In some embodiment $S^2$ has the structure:

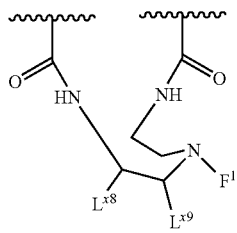

wherein $L^{x8}$ and $L^{x9}$ are independently selected from H and a linker. In some embodiments, only one of $L^{x8}$ and $L^{x9}$ is a linker. In some embodiments, $L^{x8}$ is a linker. Linkers are as defined herein. In some embodiments, $L^{x8}$ and $L^{x9}$ are H. $F^1$ is as defined herein.

In some embodiment $S^2$ has the structure:

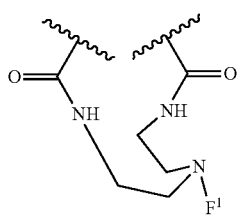

wherein $F^1$ is as defined herein.

In some embodiment $S^2$ has the structure:

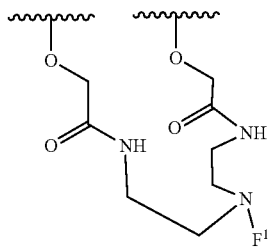

wherein $F^1$ is as defined herein.

In some embodiment $S^2$ has the structure:

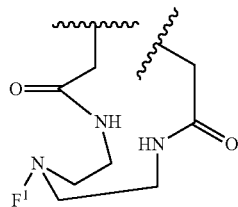

wherein $F^1$ is as defined herein.

2.1.3. Linker to Functional/Targeting Moiety

A "linker", "linking member", or "linking moiety" as used herein is a moiety that joins or potentially joins, covalently or noncovalently, a first moiety to a second moiety. In particular, a linker attaches or could potentially attach a chelator described herein to another molecule, such as a targeting moiety. In some embodiments, a linker attaches or could potentially attach a chelator described herein to a solid support. A linker comprising a reactive functional group that can be further reacted with a reactive functional group on a structure of interest in order to attach the structure of interest to the linker is referred to as a "functionalized linker". In exemplary embodiments, a linker is a functionalized linker. In exemplary embodiments, a chelator comprises one or more functionalized linkers. In some embodiments, a linker comprises a targeting moiety. In some embodiments, a linker to a targeting moiety comprises a bond to the targeting moiety.

A linker can be any useful structure for that joins a chelator to a reactive functional group or a targeting moiety, such as an antibody. Examples of a linker include 0-order linkers (i.e., a bond), substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Further exemplary linkers include substituted or unsubstituted ($C_1$, $C_2$, $C_3$, $C_4$, $C_5$, $C_6$, $C_7$, $C_8$, $C_9$ or $C_{10}$) alkyl, substituted or unsubstituted heteroalkyl, —C(O)NR'—, —C(O)O—, —C(O)S—, and —C(O)CR'R", wherein R' and R" are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, a linker includes at least one heteroatom. Exemplary linkers also include —C(O)NH—, —C(O), —NH—, —S—, —O—, and the like. In an exemplary embodiment, a linker is a heteroalkyl substituted with a reactive functional group.

Reactive Functional Groups

In one embodiment, a linker comprises a reactive functional group (or a "reactive functional moiety", used synonymously), which can be further reacted to covalently attach the linker to a targeting moiety. Reactive functional groups and classes of reactions useful in practicing the present invention are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in March, Advanced Organic Chemistry (3rd Ed., John Wiley & Sons, New York, 1985); Hermanson, Bioconjugate Techniques (Academic Press, San Diego, 1996); and Feeney et al., Modification of Proteins, Advances in Chemistry Series, Vol. 198 (American Chemical Society, Washington, D.C., 1982).

In some embodiments, a reactive functional group refers to a group selected from olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds., Organic Functional Group Preparations, (Academic Press, San Diego, 1989)).

A reactive functional group can be chosen according to a selected reaction partner. As an example, an activated ester, such as an NHS ester will be useful to label a protein via lysine residues. Sulfhydryl reactive groups, such as maleimides can be used to label proteins via amino acid residues carrying an SH-group (e.g., cystein). Antibodies may be labeled by first oxidizing their carbohydrate moieties (e.g., with periodate) and reacting resulting aldehyde groups with a hydrazine containing ligand.

The reactive functional groups can be chosen such that they do not participate in, or interfere with, the reactions necessary to assemble the reactive ligand. Alternatively, a reactive functional group can be protected from participating in the reaction by means of a protecting group. Those of skill in the art understand how to protect a particular functional group so that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Amines and Amino-Reactive Groups

In one embodiment, a reactive functional group is selected from an amine, (such as a primary or secondary amine), hydrazine, hydrazide and sulfonylhydrazide. Amines can, for example, be acylated, alkylated or oxidized. Useful non-limiting examples of amino-reactive groups include N-hydroxysuccinimide (NHS) esters, sulfur-NHS esters, imidoesters, isocyanates, isothiocyanates, acylhalides, arylazides, p-nitrophenyl esters, aldehydes, sulfonyl chlorides, thiazolides and carboxyl groups.

NHS esters and sulfur-NHS esters react preferentially with a primary (including aromatic) amino groups of a reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with amine groups of a molecule such as a protein. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus cross-linking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of carboxylic acids are also useful amino-reactive groups. Although the reagent specificity is not very high, $\alpha$- and $\epsilon$-amino groups appear to react most rapidly.

Aldehydes react with primary amines of the conjugate components (e.g., $\epsilon$-amino group of lysine residues). Although unstable, Schiff bases are formed upon reaction of the protein amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., *Biochemistry*, 1981, 20: 4836-4842, e.g., teach how to modify a protein with carbodiimides.

Sulfhydryl and Sulfhydryl-Reactive Groups

In another embodiment, a reactive functional group is selected from a sulfhydryl group (which can be converted to disulfides) and sulfhydryl-reactive group. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

Other Reactive Functional Groups

Other exemplary reactive functional groups include:
(i) carboxyl groups and various derivatives thereof including, but not limited to, N-hydroxybenztriazole esters, acid halides, acyl imidazoles, thioesters, p-nitrophenyl esters, alkyl, alkenyl, alkynyl and aromatic esters;
(ii) hydroxyl groups, which can be converted to esters, ethers, aldehydes, etc.;
(iii) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(iv) dienophile groups, which are capable of participating in Diels-Alder reactions such as, for example, maleimido groups;
(v) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(vi) alkenes, which can undergo, for example, cycloadditions, acylation, Michael addition, etc;
(vii) epoxides, which can react with, for example, amines and hydroxyl groups;
(ix) phosphoramidites and other standard functional groups useful in nucleic acid synthesis and
(x) any other functional group useful to form a covalent bond between the functionalized ligand and a molecular entity or a surface.

Functional Groups with Non-Specific Reactivities

In addition to the use of site-specific reactive moieties, the present invention contemplates the use of non-specific reactive groups to link a chelator to a targeting moiety. Non-specific groups include photoactivatable groups, for example.

Photoactivatable groups are ideally inert in the dark and are converted to reactive species in the presence of light. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein crosslinks.

In exemplary embodiments, a linker joins a chelator to a targeting moiety. That is, in exemplary embodiments, a linker comprises a targeting moiety. In some embodiments, a chelator comprises a linker to a targeting moiety. Any linker described herein may be a linker comprising a reactive functional group that could react with a reactive functional group on a targeting moiety to join the linker to the targeting moiety. Any linker described herein may be a linker comprising a bond to a targeting moiety. The term "targeting moiety" refers to a moiety serves to target or direct the molecule to which it is attached (e.g., a chelator or a chelator complexed to a metal ion (such as a radionuclide)) to a particular location or molecule. Thus, for example, a targeting moiety may be used to target a molecule to a specific target protein or enzyme, or to a particular cellular location, to a particular cell type or to a diseased tissue. As will be appreciated by those in the art, the localization of proteins within a cell is a simple method for increasing effective concentration. For example, shuttling an imaging agent and/or therapeutic into the nucleus confines them to a smaller space thereby increasing concentration. Finally, the physiological target may simply be localized to a specific compartment, and the agents must be localized appropriately.

The targeting moiety can be a small molecule (e.g., MW<500D), which includes both non-peptides and peptides. Examples of a targeting moiety also include peptides, polypeptides (including proteins, and in particular antibodies, which includes antibody fragments), nucleic acids, oligonucleotides, carbohydrates, lipids, hormones (including proteinaceous and steroid hormones (for instance, estradiol)), growth factors, lectins, receptors, receptor ligands, cofactors and the like. Targets of a targeting moiety can include a complementary nucleic acid, a receptor, an antibody, an antigen or a lectin, for example.

In exemplary embodiments, a targeting moiety can bind to a target with high binding affinity. In other words, a targeting moiety with high binding affinity to a target has a high specificity for or specifically binds to the target. In some embodiments, a high binding affinity is given by a dissociation constant $K_d$ of about $10^{-7}$ M or less. In exemplary embodiments, a high binding affinity is given by a dissociation constant $K_d$ of about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less or about $10^{-15}$ M or less. A compound may have a high binding affinity for a target if the compound comprises a portion, such as a targeting moiety, that has a high binding affinity for the target.

In exemplary embodiments, a targeting moiety is an antibody. An "antibody" refers to a protein comprising one or more polypeptides substantially encoded by all or part of the recognized immunoglobulin genes. The recognized immunoglobulin genes, for example in humans, include the kappa (κ), lambda (λ) and heavy chain genetic loci, which together compose the myriad variable region genes, and the constant region genes mu (μ), delta (δ), gamma (γ), epsilon (ε) and alpha (α), which encode the IgM, IgD, IgG, IgE, and IgA isotypes respectively. Antibody herein is meant to include full length antibodies and antibody fragments, and may refer to a natural antibody from any organism, an engineered antibody or an antibody generated recombinantly for experimental, therapeutic or other purposes as further defined below. Antibody fragments include Fab, Fab', F(ab')$_2$, Fv, scFv or other antigen-binding subsequences of antibodies and can include those produced by the modification of whole antibodies or those synthesized de novo using recombinant DNA technologies. The term "antibody" refers to both monoclonal and polyclonal antibodies. Antibodies can be antagonists, agonists, neutralizing, inhibitory or stimulatory.

While a targeting moiety may be appended to a chelator in order to localize the compound to a specific region in an animal, certain chelators have a natural affinity for cells, tissue, organs or some other part of the animal. For example, a chelator disclosed herein might have a natural or intrinsic affinity for bone. Thus, in some embodiments, a chelator (macrocycle), does not comprise a targeting moiety or a linker to a targeting moiety. A chelator lacking a targeting moiety can be used in any method that does not require specific targeting.

In some embodiments, a chelator comprises a linker to a solid support. That is, any linker described herein may be a linker comprising a reactive functional group that could react with a reactive functional group on a solid support to join the linker to the solid support. Any linker described herein may be a linker comprising a bond to a solid support. A "solid support" is any material that can be modified to contain discrete individual sites suitable for the attachment or association of a chelator. Suitable substrates include biodegradable beads, non-biodegradable beads, silica beads, magnetic beads, latex beads, glass beads, quartz beads, metal beads, gold beads, mica beads, plastic beads, ceramic beads, or combinations thereof. Of particular use are biocompatible polymers, including biodegradable polymers that are slowly removed from the system by enzymatic degradation. Example biodegradable materials include starch, cross-linked starch, poly(ethylene glycol), polyvinylpyrrolidine, polylactides (PLA), polyglycolides (PGA), poly(lactide-co-glycolides) (PLGA), polyanhydrides, polyorthoesters, poly(DTH iminocarbonate), poly(bisphenol A iminocarbonate), polycyanoacrylate, polyphosphazene, mixtures thereof and combinations thereof. Other suitable substances for forming the particles exist and can be used. In some embodiments, a solid support is a bead comprising a cross-linked starch, for example, cross-linked potato starch. Beads made from starch are completely biodegradable in the body, typically by serum amylase, a naturally occurring enzyme found in the body. In these embodiments, the chelator optionally further comprises a targeting moiety or a linker to a targeting moeity. In cases where a chelator that is attached to a solid support does not comprise a targeting moiety, the chealtor can be localized directly by the practitioner, for example, by direct surgical implantation.

In some embodiments, a linker has the structure -$L^{11}$-X, wherein $L^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and X is a reactive functional group or a targeting moiety.

In some embodiments, $L^{11}$ is selected from substituted or unsubstituted alkyl and substituted or unsubstituted heteroalkyl. In some embodiments, $L^{11}$ is heteroalkyl. In some embodiments, $L^{11}$ is ($C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ or $C_{20}$) alkyl in which 1, 2 or 3 atoms are replaced with a heteroatom, such as nitrogen or oxygen.

In some embodiments, X is selected from —$NH_2$ and —CO(O)H.

In some embodiments, -$L^{11}$-X is selected from

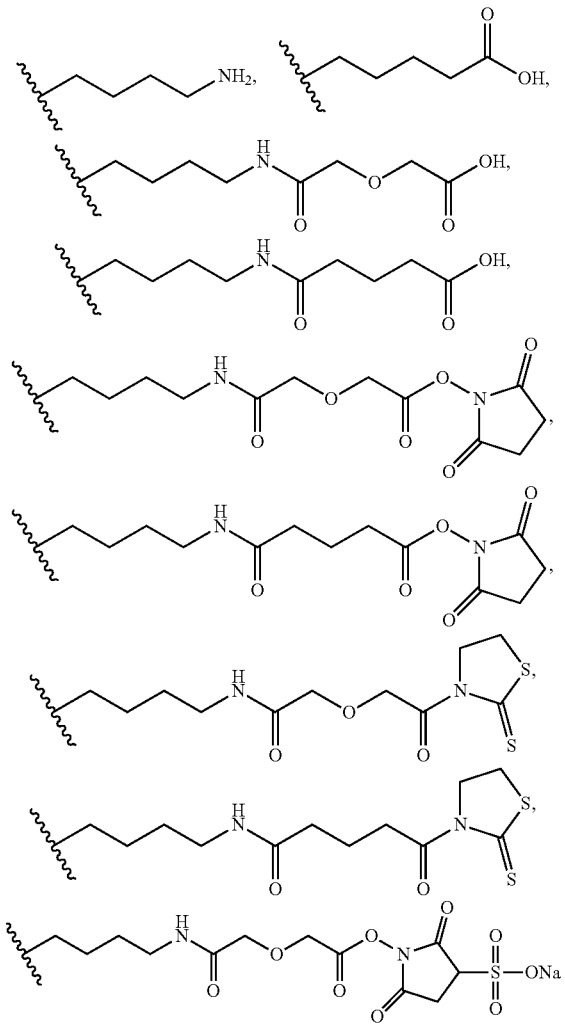

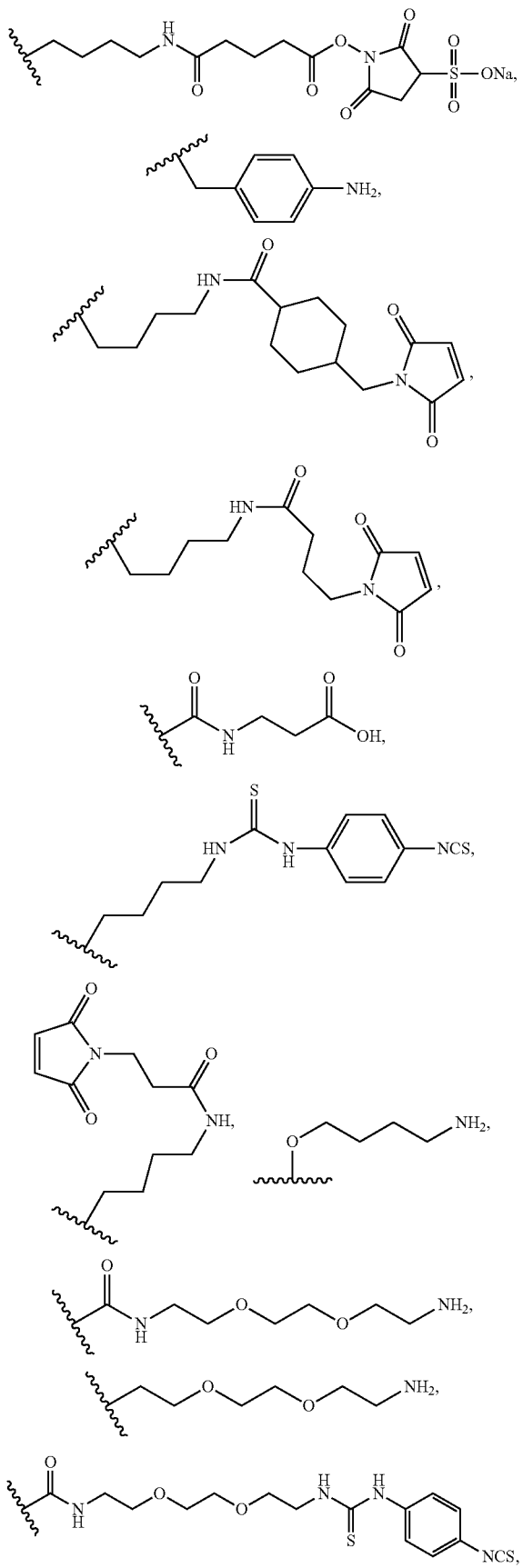

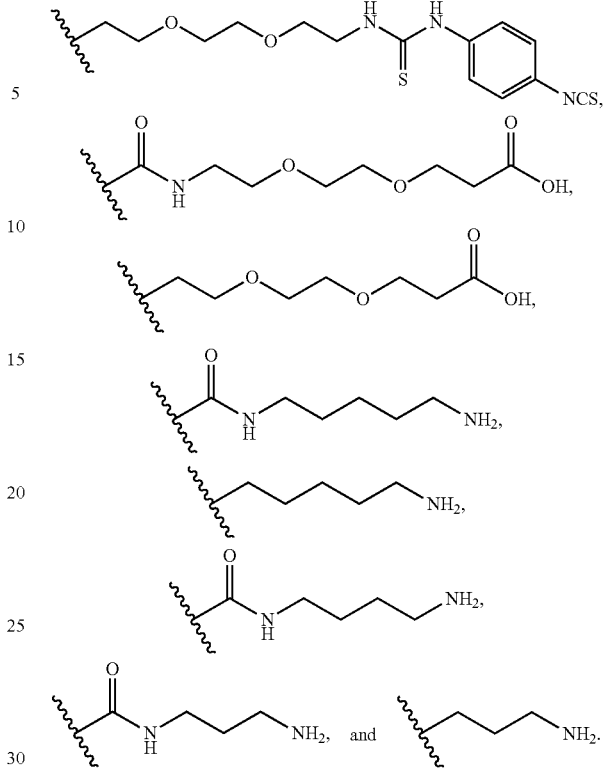

In exemplary embodiments, X is a targeting moiety.

In exemplary embodiments, a linker is a linker to a targeting moiety. In some embodiments, the targeting moiety is selected from a polypeptide, a nucleic acid, a lipid, a polysaccharide, a small molecule, a cofactor and a hormone. In exemplary embodiments, the targeting moiety is an antibody or antibody fragment.

In some embodiments, a linker includes an aliphatic carbon chain or a poly-ethyleneglycol (PEG) chain. Thus, a linker can comprise a structure selected from:

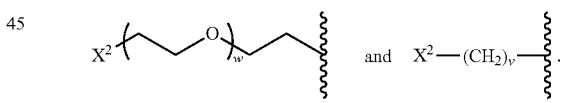

The integer v is selected from 1 to 20, and w is an integer from 1 to 1,000 or 1 to 500 or 1 to 100 or 1 to 50 or 1 to 10.

Exemplary $X^2$ groups include OH, alkoxy, and one of the following structures:

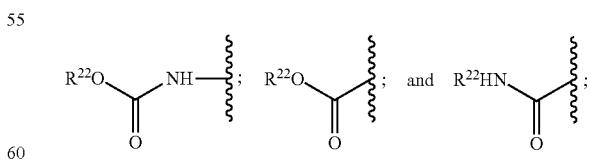

wherein $R^{22}$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl. The integer v is selected from 1 to 20, and w is an integer from 1 to 1,000 or 1 to 500 or 1 to 100 or 1 to 50 or 1 to 10.

In some embodiments, a linker has the structure:

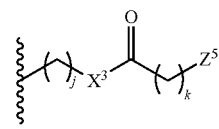

wherein $Z^5$ is selected from H, $OR^{23}$, $SR^{23}$, $NHR^{23}$, $OCOR^{24}$, $OC(O)NHR^{24}$, $NHC(O)OR^{23}$, $OS(O)_2OR^{23}$, and $C(O)R^{24}$. $R^{23}$ is selected from H, substituted or unsubstituted alkyl, and substituted or unsubstituted heteroalkyl. $R^{24}$ is selected from H, $OR^{25}$, $NR^{25}NH_2$, SH, $C(O)R^{25}$, $NR^{25}H$, substituted or unsubstituted alkyl and substituted or unsubstituted heteroalkyl. $R^{25}$ is selected from H, substituted or unsubstituted alkyl and substituted or unsubstituted alkyl. $X^3$ is selected from O, S and $NR^{26}$, wherein $R^{26}$ is a member selected from H, substituted or unsubstituted alkyl and substituted or unsubstituted heteroalkyl. The integers j and k are members independently selected from 1, 2, 3, 4, 5, 6, 7, 8, 9, 10, 11, 12, 13, 14, 15, 16, 17, 18, 19 and 20. In some embodiments, the integers j and k are members independently selected from 1, 2, 3, 4, 5, 6.

In a linker with multiple reactive functional groups, a particular functional group can be chosen such that it does not participate in, or interfere with, the reaction controlling the attachment of the functionalized spacer component to another ligand component. Alternatively, the reactive functional group can be protected from participating in the reaction by the presence of a protecting group. Those of skill in the art understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

2.1.4. Modifying Moiety

In some embodiments, one, two or all of $S^1$, $S^2$ and $A^{p1}$ comprise a modifying moiety. Each of the modifying moieties can be the same or different.

The modifying moiety modifies various properties of the macrocycle and/or a complex formed between the macrocycle and a metal ion, such as solubility, charge, or affinity. In some embodiments, the modifying moiety does not interact with the metal when the macrocycle is complexed to a metal. In some embodiments, the modifying moiety is a solubilizing group, a hormone-derived moiety, a prodrug moiety (for example, with a cleavable moiety), an oligonucleotide, ssDNA, dsDNA, RNA, or a peptide. The solubilizing group improves solubility of the macrocycle and/or a complex formed between the macrocycle and a metal ion in aqueous media. In some embodiments, the hormone (of the homone-derived moiety) is a steroid. In some embodiments, the steroid is estradiol. In some embodiments, the modifying moiety is an estradiol-derived moiety. Peptides of a hydrophilic and hydrophobic nature by virtue of their amino acid composition may be used to tune solubility of the macrocycle and/or a complex formed between the macrocycle and a metal ion.

In some embodiments, $S^2$ comprises a modifying moiety. In some embodiments, $A^{p1}$ comprises a linker; and $S^1$, $S^2$, or both comprise a modifying moiety. In some embodiments, $S^1$ comprises a linker; and $S^2$, $A^{p1}$, or both comprise a modifying moiety. In some embodiments, $S^1$ comprises a modifying moiety. In some embodiments, $S^1$ comprises a linker; and $A^{p1}$ comprises a modifying moiety.

In some embodiments, $F^1$ comprises a modifying moiety. In some embodiments, $F^1$ is a modifying moiety.

In some embodiments, $F^1$ is substituted or unsubstituted heteroalkyl. In some embodiments, $F^1$ is a substituted or unsubstituted polyether. In some embodiments, $F^1$ comprises an estradiol-derived moiety. In some embodiments, $F^1$ is a polyether substituted with an estradiol-derived moiety. In some embodiments, $F^1$ is selected from:

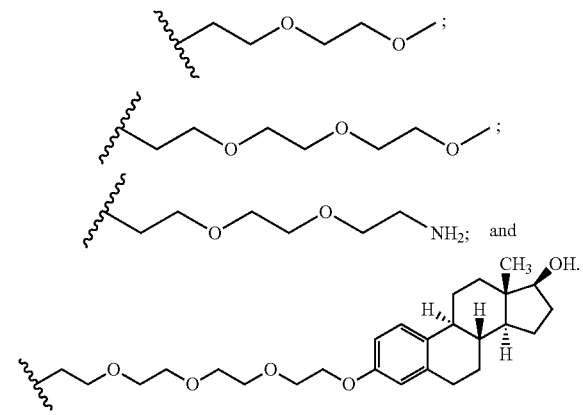

In some embodiments, $F^1$ is a peptide. In some embodiments, $F^1$ is

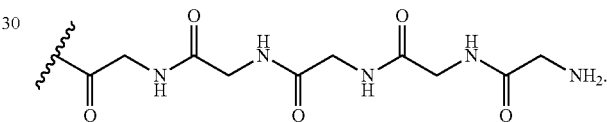

In some embodiments, $F^1$ comprises an oligunucleotide.
In some embodiments, $F^1$ is a linker.

2.1.5. Exemplary Macrocycles

In some embodiments, the invention provides a macrocycle having the structure:

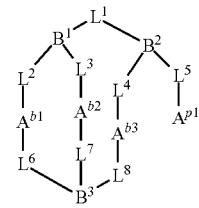

wherein
$B^1$, $B^2$, and $B^3$ are independently selected from N and C;
$L^1$, $L^2$, $L^3$, $L^4$, $L^5$, $L^6$, $L^7$, and $L^8$ are independently selected from substituted or unsubstituted alkyl, and substituted or unsubstituted heteroalkyl;
$A^{b1}$, $A^{b2}$, and $A^{b3}$ are members independently selected from:

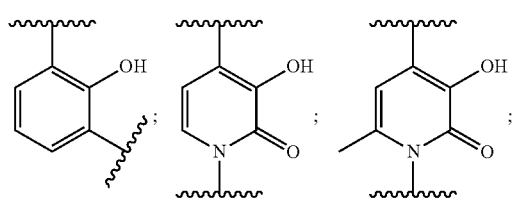

-continued

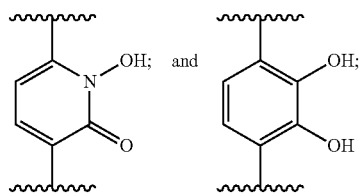

and
$A^{p1}$ is a member selected from:

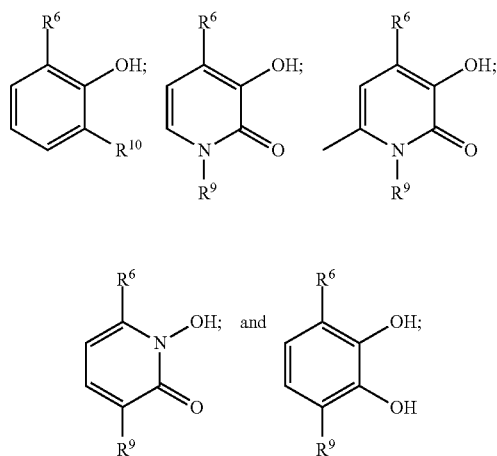

wherein $R^6$, $R^9$, and $R^{10}$ are as defined herein, with the proviso that $R^6$, $R^9$, or $R^{10}$ is a bond to $L^5$. In some embodiments, the macrocycle is covalently modified with at least one linker. In some embodiments, one of L, $L^2$, $L^3$, $L^4$, $L^5$, $L^6$, $L^7$, $L^8$, and $A^{p1}$ is substituted with a linker. In some embodiments, $A^{p1}$ is substituted with a linker. In some embodiments, $L^5$ is substituted with a linker. In some embodiments, $L^2$ is substituted with a linker.

In some embodiments, the invention provides a macrocycle having the structure:

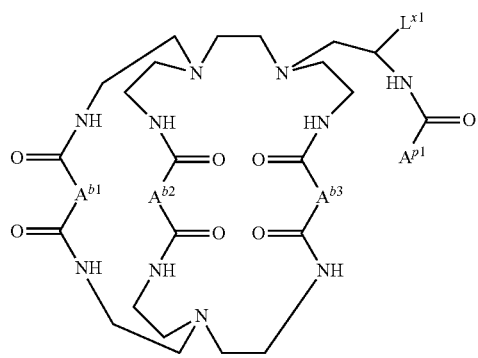

wherein
$A^{b1}$, $A^{b2}$, and $A^{b3}$ are members independently selected from:

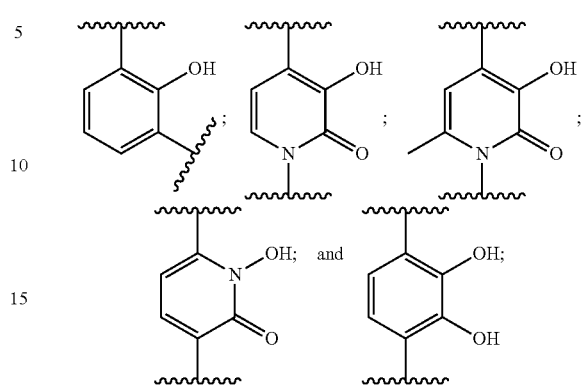

$A^{p1}$ is a member selected from:

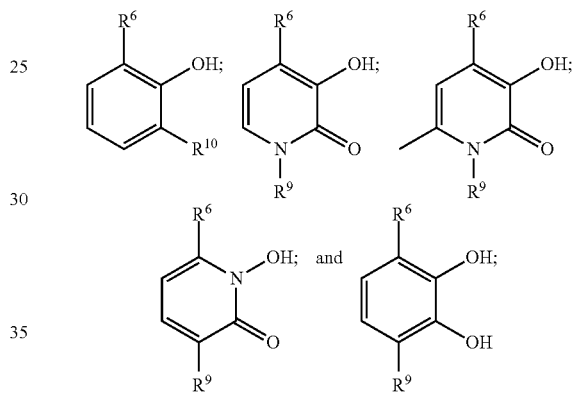

wherein $R^6$, $R^9$, and $R^{10}$ are as defined herein, with the proviso that $R^6$, $R^9$, or $R^{10}$ is a bond to $L^5$; and
$L^{x1}$ is H or a linker.
In some embodiments, the macrocycle is covalently modified with at least one linker. In some embodiments, $L^{x1}$ is a linker or $A^{p1}$ is substituted with a linker. In some embodiments, $A^{p1}$ is substituted with a linker. In some embodiments, $L^{x1}$ is a linker.

In some embodiments, the invention provides a macrocycle having the structure:

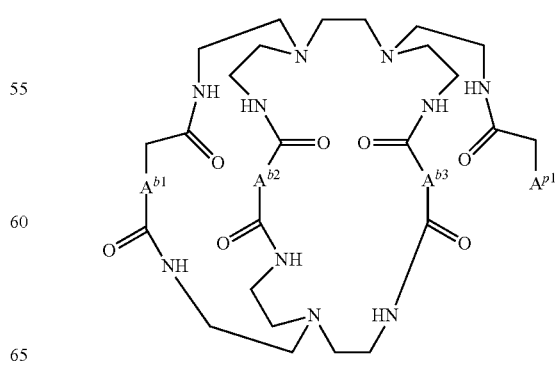

wherein $A^{b1}$, $A^{b2}$, and $A^{b3}$ are members independently selected from:

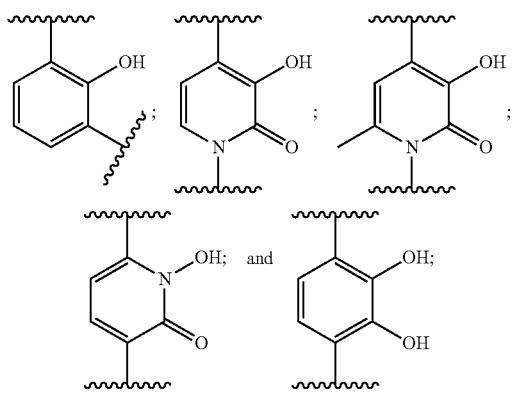

and $A^{p1}$ is a member selected from:

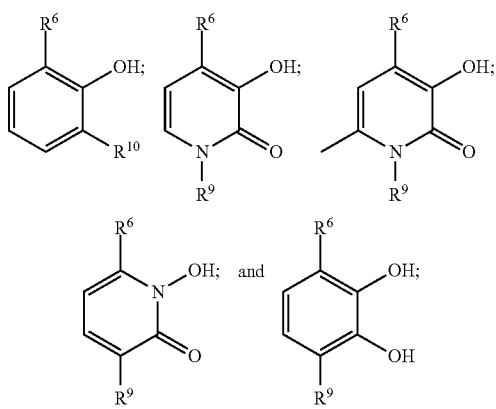

wherein $R^6$, $R^9$, and $R^{10}$ are as defined herein, with the proviso that $R^6$, $R^9$, or $R^{10}$ is a bond to $L^5$. In some embodiments, the macrocycle is covalently modified with at least one linker. In some embodiments, $A^{p1}$ is substituted with a linker.

In some embodiments, the invention provides a macrocycle having the structure:

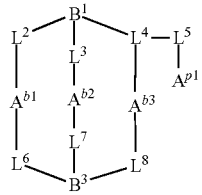

wherein $B^1$ and $B^3$ are independently selected from N and C;

$L^2$, $L^3$, $L^4$, $L^5$, $L^6$, $L^7$, and $L^8$ are independently selected from substituted or unsubstituted alkyl, and substituted or unsubstituted heteroalkyl;

$A^{b1}$, $A^{b2}$, and $A^{b3}$ are members independently selected from:

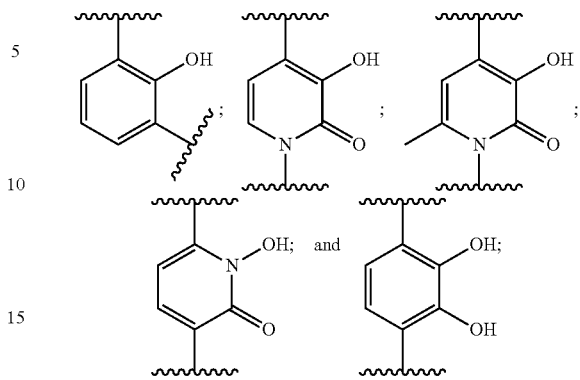

and $A^{p1}$ is a member selected from:

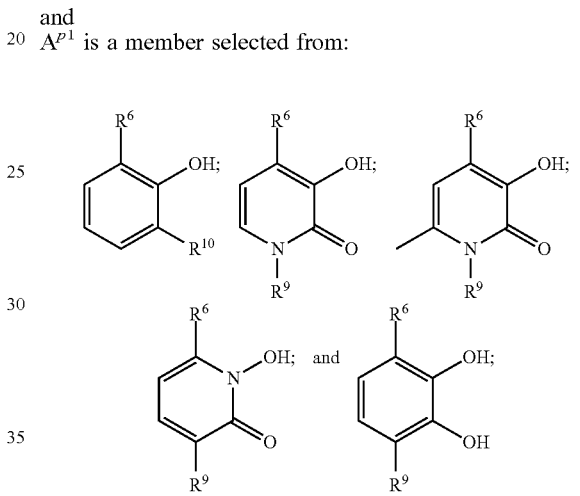

wherein $R^6$, $R^9$, and $R^{10}$ are as defined herein, with the proviso that $R^6$, $R^9$, or $R^{10}$ is a bond to $L^5$. In some embodiments, the macrocycle is covalently modified with at least one linker. In some embodiments, one of $L^2$, $L^3$, $L^4$, $L^5$, $L^6$, $L^7$, $L^8$, and $A^{p1}$ is substituted with a linker. In some embodiments, $A^{p1}$ is substituted with a linker. In some embodiments, $L^5$ is substituted with a linker. In some embodiments, $L^2$ is substituted with a linker.

In some embodiments, the invention provides a macrocycle having the structure:

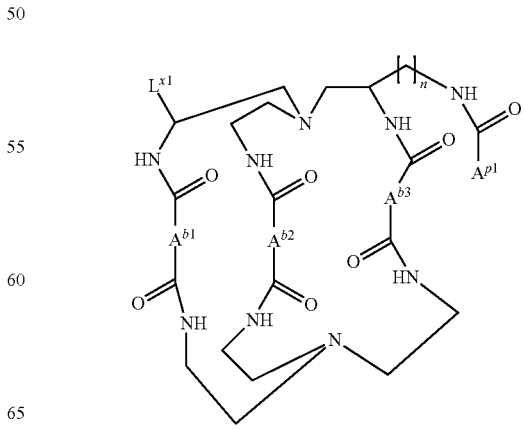

wherein
n is 1, 2, 3, 4, 5, or 6;
$A^{b1}$, $A^{b2}$, and $A^{b3}$ are members independently selected from:

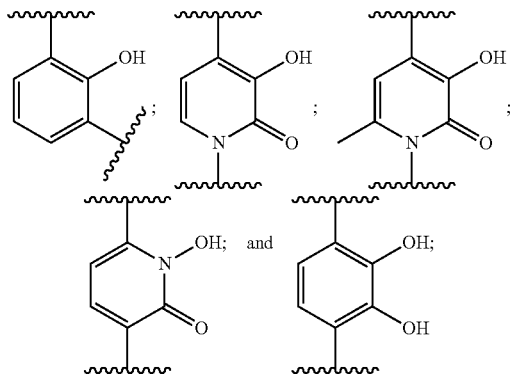

and
$A^{p1}$ is a member selected from:

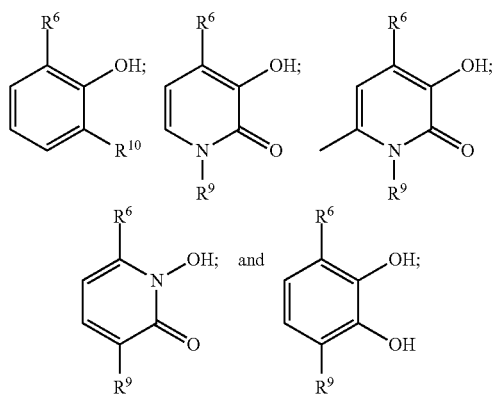

wherein $R^6$, $R^9$, and $R^{10}$ are as defined herein, with the proviso that $R^6$, $R^9$, or $R^{10}$ is a bond to $L^5$; and
$L^{x1}$ is H or a linker.

In some embodiments, the macrocycle is covalently modified with at least one linker. In some embodiments, $L^{x1}$ is a linker or $A^{p1}$ is substituted with a linker. In some embodiments, $A^{p1}$ is substituted with a linker. In some embodiments, $L^{x1}$ is a linker.

In some embodiments, the invention provides a macrocycle having the structure:

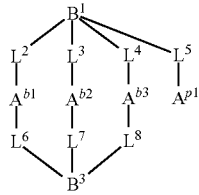

wherein
$B^1$ is C;
$B^3$ is N or C;
$L^2$, $L^3$, $L^4$, $L^5$, $L^6$, $L^7$, and $L^8$ are independently selected from substituted or unsubstituted alkyl, and substituted or unsubstituted heteroalkyl;

$A^{b1}$, $A^{b2}$, and $A^{b3}$ are members independently selected from:

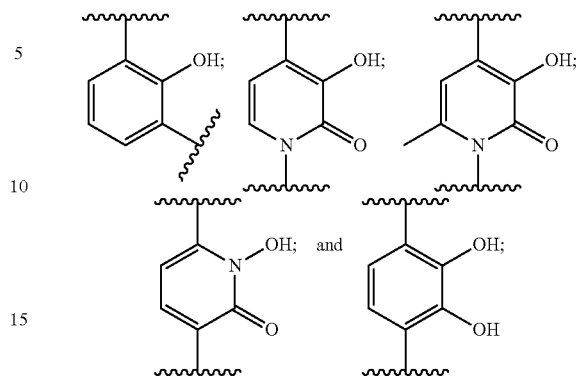

and
$A^{p1}$ is a member selected from:

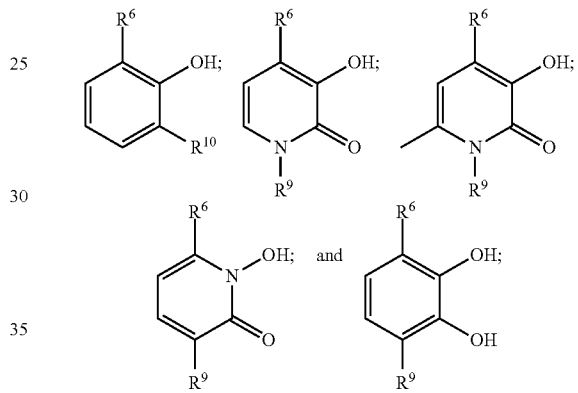

wherein $R^6$, $R^9$, and $R^{10}$ are as defined herein, with the proviso that $R^6$, $R^9$, or $R^{10}$ is a bond to $L^5$. In some embodiments, the macrocycle is covalently modified with at least one linker. In some embodiments, one of $L^2$, $L^3$, $L^4$, $L^5$, $L^6$, $L^7$, $L^8$, and $A^{p1}$ is substituted with a linker. In some embodiments, $A^{p1}$ is substituted with a linker. In some embodiments, $L^5$ is substituted with a linker. In some embodiments, $L^2$ is substituted with a linker.

In some embodiments, the invention provides a macrocycle having the structure:

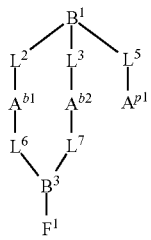

wherein
$B^1$ and $B^3$ are independently selected from N and C;
$F^1$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

$L^2$, $L^3$, $L^5$, $L^6$, and $L^7$ are independently selected from substituted or unsubstituted alkyl, and substituted or unsubstituted heteroalkyl;

$A^{b1}$ and $A^{b2}$ are members independently selected from:

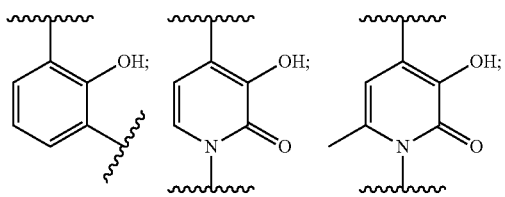

and

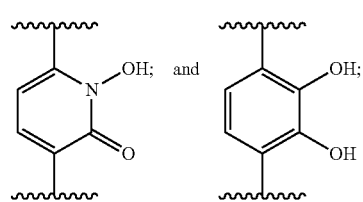

and $A^{p1}$ is a member selected from:

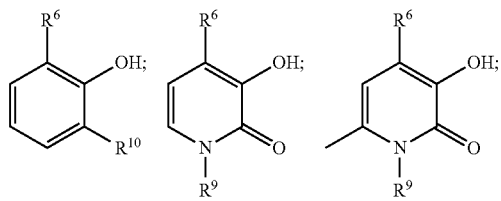

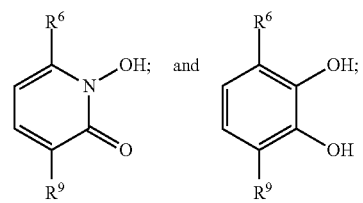

wherein $R^6$, $R^9$, and $R^{10}$ are as defined herein, with the proviso that $R^6$, $R^9$, or $R^{10}$ is a bond to $L^5$. In some embodiments, the macrocycle is covalently modified with at least one linker. In some embodiments, one of $L^2$, $L^3$, $L^5$, $L^6$, $L^7$, and $A^{p1}$ is substituted with a linker. In some embodiments, $A^{p1}$ is substituted with a linker. In some embodiments, $L^5$ is substituted with a linker. In some embodiments, $L^2$ is substituted with a linker.

In some embodiments, $F^1$ is modifying moiety. Modifying moieties are as defined herein.

In some embodiments, the invention provides a macrocycle having the structure:

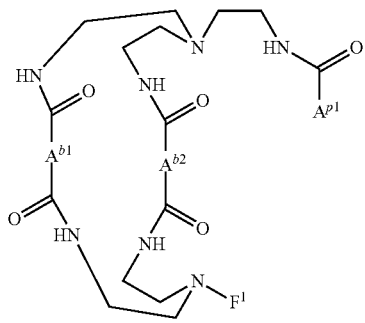

wherein
$F^1$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl;
$A^{b1}$ and $A^{b2}$ are members independently selected from:

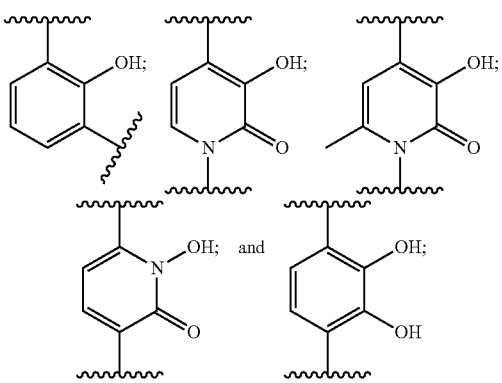

and
$A^{p1}$ is a member selected from:

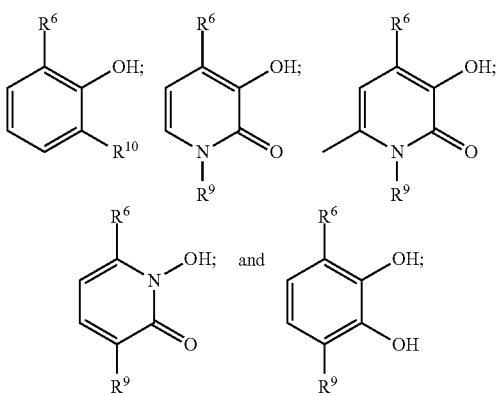

wherein $R^6$, $R^9$, and $R^{10}$ are as defined herein, with the proviso that $R^6$, $R^9$, or $R^{10}$ is a bond to $L^5$. In some embodiments, the macrocycle is covalently modified with at least one linker. In some embodiments, $A^{p1}$ is substituted with a linker.

In some embodiments, $F^1$ is modifying moiety. Modifying moieties are as defined herein.

Additional exemplary macrocycles are shown in the Examples.

2.2. Complexes

In one aspect, the invention provides a complex of a macrocycle disclosed herein with a metal ion.

Any of the combinations of macrocycles disclosed herein and a metal ion disclosed herein are encompassed by this disclosure and specifically provided by the invention.

In some embodiments, the complex is luminescent.

2.2.1. Metals

In some embodiments, the metal is an actinide. In some embodiments, the actinide is thorium (Th).

In some embodiments, the metal is a lanthanide. In some embodiments, the lanthanide is terbium (Tb). In some embodiments, the lanthanide is europium (Eu). In some embodiments, the lanthanide is dysprosium (Dy). In some embodiments, the lanthanide is lutetium (Lu). In some embodiments, the lanthanide is gadolinium (Gd).

In some embodiments the metal is yttrium (Y). In some embodiments, the metal is zirconium (Zr).

In some embodiments, the metal ion is yttrium(III). In some embodiments, the metal ion is europium(III). In some embodiments, the metal ion is terbium(III). In some embodiments, the metal ion is zirconium(IV). In some embodiments, the metal ion is thorium(IV).

In some embodiments, the metal (ion) is a radionuclide. In some embodiments, the metal ion is $^{227}$Th(IV). In some embodiments, the metal ion is $^{89}$Zr(IV).

In some embodiments, the metal is $^{177}$Lu. In some embodiments, the metal is $^{166}$Ho. In some embodiments, the metal is $^{153}$Sm. In some embodiments, the metal is $^{90}$Y. In some embodiments, the metal is $^{86}$Y. In some embodiments, the metal is $^{166}$Dy. In some embodiments, the metal is $^{165}$Dy. In some embodiments, the metal is $^{169}$Er. In some embodiments, the metal is $^{175}$Yb. In some embodiments, the metal is $^{225}$Ac. In some embodiments, the metal is $^{149}$Tb. In some embodiments, the metal is $^{153}$Gd. In some embodiments, the metal is $^{230}$U.

In some embodiments, the metal is $^{111}$In. In some embodiments, the metal is $^{67}$Ga. In some embodiments, the metal is $^{67}$Cu. In some embodiments, the metal is $^{64}$Cu. In some embodiments, the metal is $^{186}$Re. In some embodiments, the metal is $^{188}$Re. In some embodiments, the metal is $^{111}$Ag. In some embodiments, the metal is $^{109}$Pd. In some embodiments, the metal is $^{212}$Pb. In some embodiments, the metal is $^{203}$Pb. In some embodiments, the metal is $^{212}$Bi. In some embodiments, the metal is $^{213}$Bi. In some embodiments, the metal is $^{195m}$Pt. In some embodiments, the metal is $^{201}$Tl. In some embodiments, the metal is $^{55}$Co. In some embodiments, the metal is $^{99m}$Tc.

2.2.1.1. Radionuclides

The chelating moieties disclosed herein can be used to bind metal ions, in particular, a radionuclide. The term "radionuclide" or "radioisotope" refers to a radioactive isotope or element with an unstable nucleus that tends to undergo radioactive decay. Numerous decay modes are known in the art and include alpha decay, proton emission, neutron emission, double proton emission, spontaneous fission, cluster decay, β$^-$ decay, positron emission (β$^+$ decay), electron capture, bound state beta decay, double beta decay, double electron capture, electron capture with positron emission, double positron emission, isomeric transition and internal conversion.

Exemplary radionuclides include alpha-emitters, which emit alpha particles during decay. In some embodiments, a radionuclide is an emitter of a gamma ray or a particle selected from an alpha particle, an electron and a positron.

In some embodiments, the radionuclide is an actinide. In some embodiments, the radionuclide is a lanthanide. In some embodiments, the radionuclide is a 3$^+$ ion. In some embodiments, the radionuclide is a 4$^+$ ion. In some embodiments the radionuclide is a 2$^+$ ion.

Of particular use in the complexes provided herein are radionuclides selected from isotopes of U, Pu, Fe, Cu, Sm, Gd, Tb, Dy, Ho, Er, Yb, Lu, Y, Th, Zr, In, Ga, Bi, Ra, At and Ac. In some embodiments, a radionuclide is selected form radium-223, thorium-227, astatine-211, bismuth-213, Lutetium-177, and actinium-225. Other useful radioisotopes include bismuth-212, iodine-123, copper-64, iridium-192, osmium-194, rhodium-105, samarium-153, and yttrium-88, yttrium-90, and yttrium-91. In exemplary embodiments, the radionuclide is thorium, particularly selected from thorium-227 and thorium-232. In some embodiments, thorium-226 is excluded. In some embodiments, U is excluded. In some embodiments, uranium-230 is excluded. That is, in some embodiments, a radionuclide is not U, or a radionuclide is not uranium-230 or a radionuclide is not thorium-226.

$^{232}$Th exists in nature as an α-emitter with a half life of 1.4×10$^{10}$ yr. In aqueous solution, Th(IV) is the only oxidation state. Thorium(IV) ion is bigger than Pu(IV) and usually forms complexes with 9 or higher coordination number. For example, the crystal structure of both Th(IV) complexes of simple bidentate 1,2-HOPO and Me-3,2-HOPO have been determined as nine coordinated species.

Similar to other actinide ions, thorium(IV) prefers forming complexes with oxygen, especially negative oxygen donor ligands. Thorium(IV) also prefers octadentate or higher multidentate ligands:

| Ligand | Acac | NTA | HEDTA* | EDTA** | DTPA | TTHA |
|---|---|---|---|---|---|---|
| Ligand Type | Bi-dentate | Tetra- | Hexa- | Hexa- | Octa- | Deca- |
| Log K$_1$ | 7.85 | 16.9 | 18.5 | 25.3 | 30.34 | 31.9 |

*with one alcoholic oxygen and three carboxyl groups;
**with four carboxyl groups.

Other radionuclides with diagnostic and therapeutic value that can be used with the compounds disclosed herein can be found, for example, in U.S. Pat. Nos. 5,482,698 and 5,601,800; and Boswell and Brechbiel, Nuclear Medicine and Biology, 2007 October, 34(7): 757-778 and the manuscript thereof made available in PMC 2008 Oct. 1.

3. Uses

The chelators and complexes disclosed herein can be used in a wide variety of therapeutic and diagnostic settings.

In one aspect, the invention provides a method of treating a disease in an animal comprising administering a complex disclosed herein to the animal, whereby the disease is ameliorated or eliminated.

In one aspect, the invention provides a method of diagnosing a disease in an animal comprising (a) administering a complex disclosed herein to the animal and (b) detecting the presence or absence of a signal emitted by the complex. In some embodiments, the detecting step comprises obtaining an image based on the signal.

In some embodiments, the disease is cancer.

In some embodiments, the complex comprises a linker to a targeting moiety and the method further comprises localizing the complex to a targeting site in the animal by binding the targeting moiety to the targeting site.

The compounds disclosed herein are particularly well suited for the preparation of stable, pre-labeled antibodies for use in the diagnosis and treatment of cancer and other diseases. For example, antibodies expressing affinity for specific tumors or tumor-associated antigens are labeled with a diagnostic radionuclide-complexed chelate, and the labeled antibodies can be further stabilized through lyophilization. Where a chelate is used, it generally is covalently attached to the antibody. The antibodies used can be polyclonal or monoclonal, and the radionuclide-labeled antibodies can be prepared according to methods known in the art. The method of preparation will depend upon the type of radionuclide and antibody used. A stable, lyophilized, radiolabeled antibody can be reconstituted with suitable diluent at the time of intended use, thus greatly simplifying the on site preparation process. The methods of the invention can be applied to stabilize many types of pre-labeled antibodies, including, but not limited to, polyclonal and monoclonal antibodies to tumors associated with melanoma, colon cancer, breast cancer, prostate cancer, etc. Such antibodies are known in the art and are readily available.

In some embodiments, cleavage of $A^{P1}$ from the macrocycle (for example, when $L^5$ comprises a cleavable bond as disclosed herein) results in a detectable change in a property (such as MRI signal or fluorescence) of the macrocycle or complex thereof. This mechanism can be used, for example, to detect an enzyme capable of cleaving an enzymatically cleavable bond of $L^5$.

4. Synthesis

Any scaffold moiety can be derivatized with at least one linker, such as a functionalized linker. Thus, in one exemplary embodiment, a linker, such as a functionalized linker, can be attached to the scaffold moiety. In another exemplary embodiment, a linker, such as a functionalized linker, is attached to a chelating moiety. A functionalized linker can reacted to form a bond with a targeting moiety. The linker can also be attached to any other linker within a compound.

Scaffold moieties that include a linker can be prepared by the following exemplary methods.

Scheme 1.1.
Reverse synthetic scheme for carboxyl functionalized H22 cap-amine.

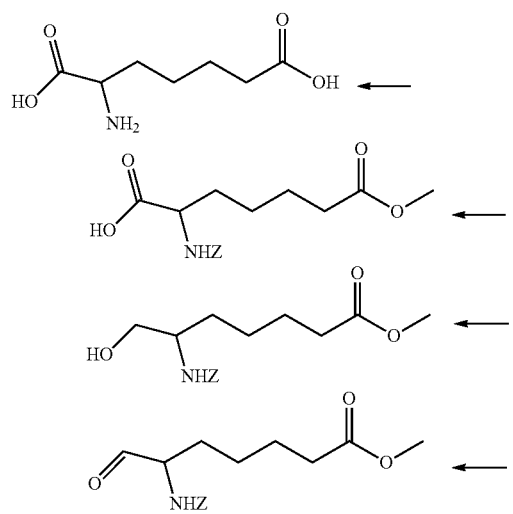

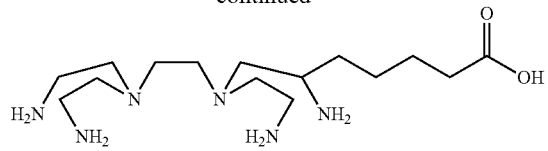

Other functionalize scaffolds include those in which the chiral carbon is placed on the central ethylene bridge of H22-amine. An exemplary route to such a scaffold initiates with 2,3-Diaminopropionic acid, as its carboxyl group is connected directly to the amine backbone to give a very rigid geometry, extended carboxyl chain is needed to provide flexibility for eventual protein conjugating. A synthetic scheme to the scaffold is shown in scheme 1.2.

Scheme 1.2

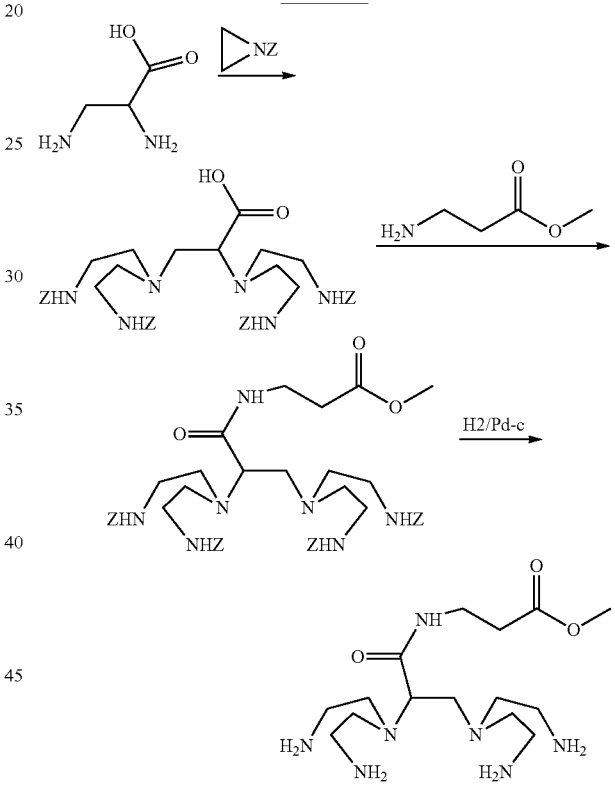

Variations on this synthesis include the use of a nitrophenylalanine or a BOC-amino group, which are optionally converted to carboxyl groups. Synthetic routes to these scaffolds are shown in Schemes 1.3 and 1.4.

Scheme 1.3

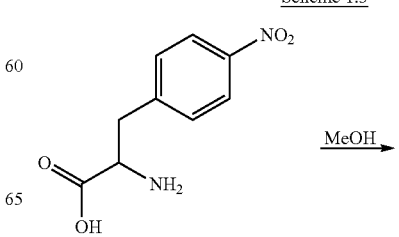

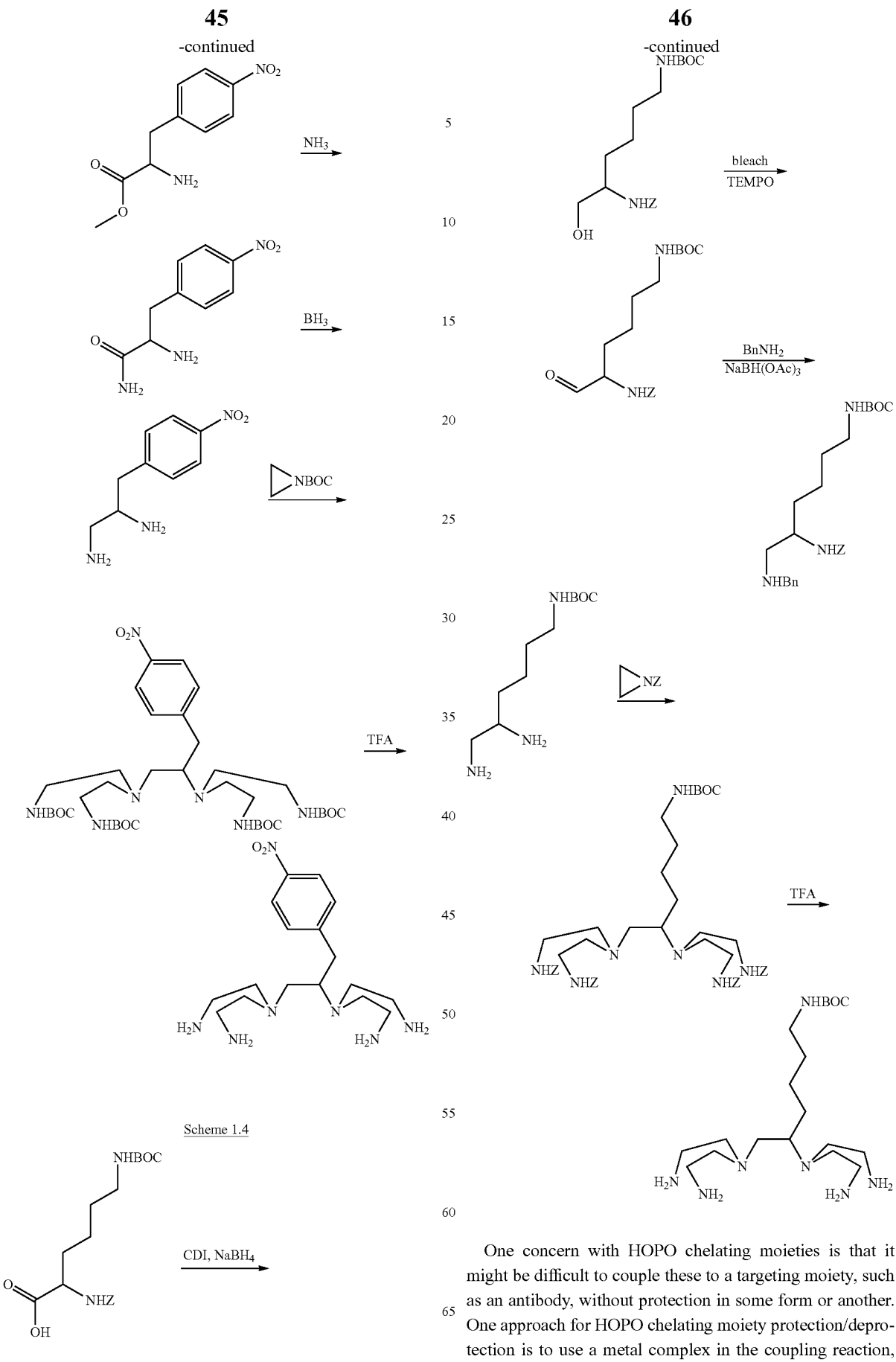
One concern with HOPO chelating moieties is that it might be difficult to couple these to a targeting moiety, such as an antibody, without protection in some form or another. One approach for HOPO chelating moiety protection/deprotection is to use a metal complex in the coupling reaction, then remove the metal from the metal complex-antibody conjugate after coupling to make room for the radionuclide (transmetalation). Another approach is to use ortho-nitrobenzyl in place of the benzyl protective group in the HOPO chelating moiety synthesis, and photodeprotect this after coupling the potential chelating moiety to the antibody.

Additional guidance for deprotecting, activating and attaching one or more chelating moieties to one or more scaffolds can be found, for example in U.S. Pat. Nos. 5,624,901; 6,406,297; 6,515,113 and 6,846,915; US Patent Application Publications 2008/0213780; 2008/0213917 and 2010/0015725; and PCT/US2010/046517.

Exemplary macrocycles, any of which can be derivatized with a linker (e.g., a functionalized linker or a linker comprising a targeting moiety) are disclosed throughout the application.

EXAMPLES

The compounds and complexes of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to limit the scope of reactions or reaction sequences that are useful in preparing the compounds of the present invention.

Example 1

Synthesis of an Octa-Coordinating Bi-Macrocyclic Bifunctional Chelator (Scheme 1).

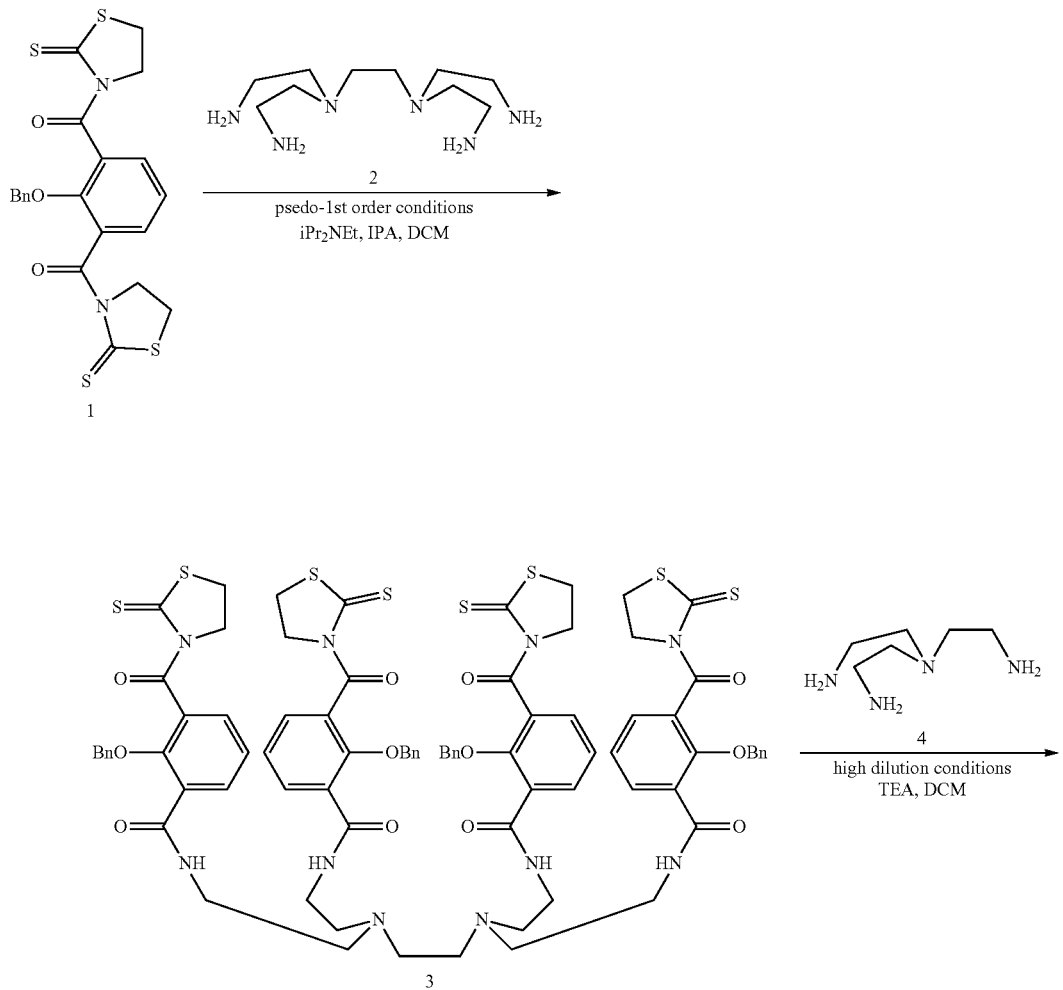

Scheme 1. Synthesis of bi-macrocyclic bifunctional chelator 8.

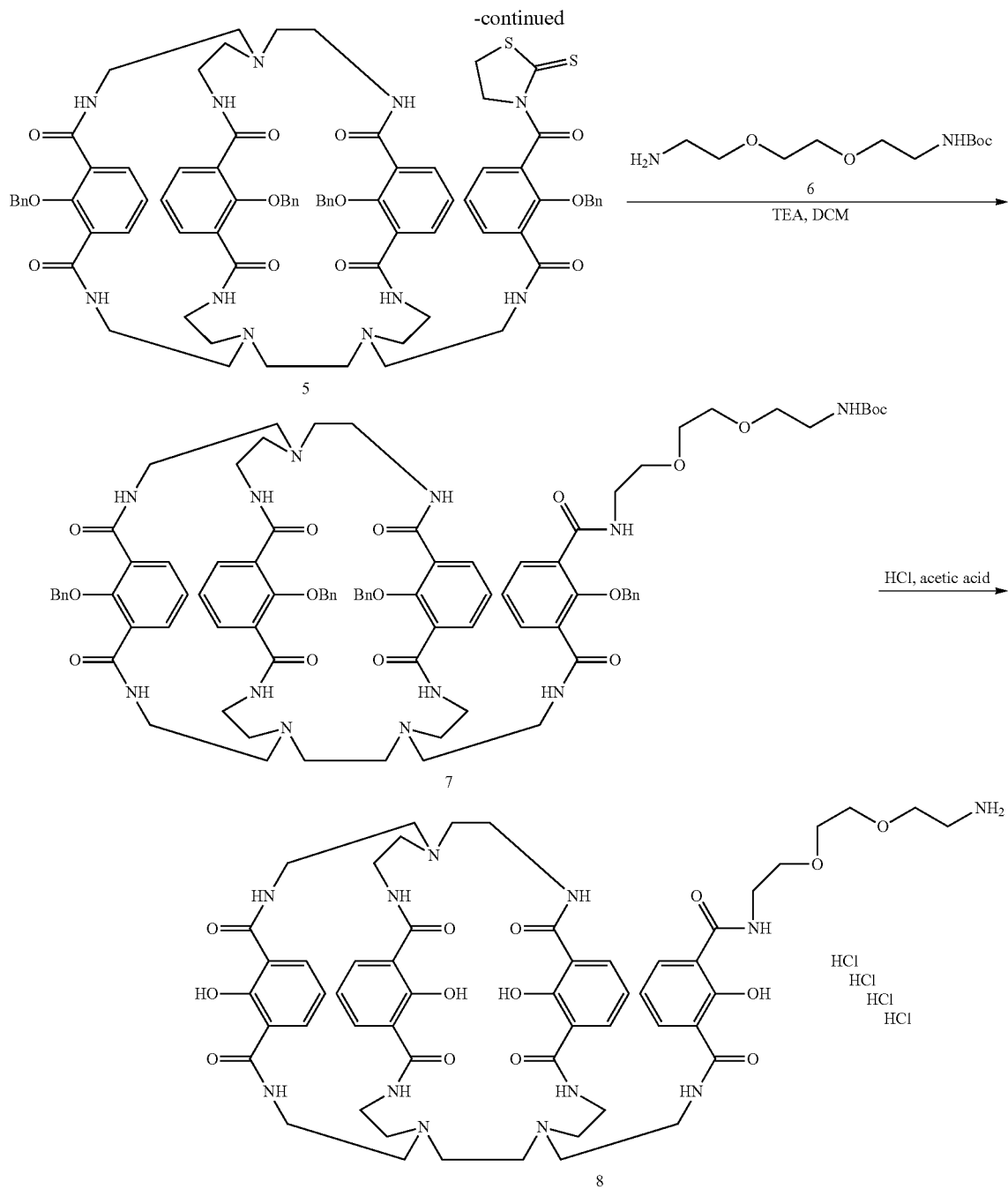

Preparation of an isophthalamide (IAM) bi-macrocyclic ligand began with 2-benzyloxy-1,3-phenylenebis((2-thioxothiazolidin-3-yl)methanone) 1, which was condensed with tetrakis-(2-aminoethyl) ethylene diamine 2 under pseudo-first order conditions to provide the activated tetraamide 3, which was reacted with tris-(2-aminoethyl)amine 4 under high dilution conditions to form the bi-macrocycle 5. The remaining activated amide in 5 was reacted with amine 6 to provide bi-macrocycle 7. Protective groups were removed using a solution of concentrated hydrochloric acid in acetic acid to provide bi-macrocycle 8.

2-Benzyloxy-1,3-phenylenebis((2-thioxothiazolidin-3-yl) methanone) 1 was synthesized as described (Samuel, A. P. S., et al., Inorg. Chem. 2008, 47, 7535-7544).

N,N',N'',N'''-[1,2-ethanediylbis(nitrilodi-2,1-ethanediyl)] tetrakis {2-benzyloxy-3-[(2-thioxo-3-thiazolidinyl)carbonyl]benzamide} 3. Tetrakis-(2-aminoethyl) ethylene diamine 2 (581 mg, 2.50 mmol) was dissolved in ca. 10% isopropyl alcohol in dichloromethane (48 mL) and triethylamine (1.74 mL, 12.5 mmol) and added using a syringe pump (NE1000) to a solution of 2-benzyloxy-1,3-phenylenebis((2-thioxothiazolidin-3-yl)methanone) 1 (23.7 g, 50 mmol) in dichloromethane (anhydrous, 100 mL) and triethylamine (1.74 mL, 12.5 mmol) over a period of 50 hrs at a rate of 1.00 mL/hr. After a further 24 hr, solvent was removed under reduced pressure, and the crude product was purified by silica gel chromatography using 0.1% triethylamine, 2-5% isopropyl alcohol in dichloromethane as eluents. Fractions containing product were combined, solvent was removed under reduced pressure, and the residue dried in vacuo to provide compound 3 (1.611 g, 39.0%). $^1$H NMR (300 MHz, CDCl$_3$): δ=8.02-7.99 (d of d, 4H, ArH), 7.46-7.44 (m, 8H, ArH), 7.30-7.20 (m, 20H, PhH), 4.96 (s, 8H, PhCH$_2$O), 4.39 (t, 8H, NCH$_2$CH$_2$S), 3.26 (m, 8H, CH$_2$NC=O), 3.02 (t, 8H, NCH$_2$CH$_2$S), 2.38 (m, 12H, CH$_2$N). $^{13}$C NMR (300 MHz, CDCl$_3$): δ=201, 167, 165, 154, 136, 134, 132, 130, 129, 128, 125, 59, 55, 53, 52, 38, 29. FTMS pESI: calculated for $C_{82}H_{81}N_{10}O_{12}S_8$ [MH]$^+$, 1653.3796, found, 1653.3855.

Benzyl-protected bi-macrocycle 5. A solution of tris-(2-aminoethyl)amine 4 (54 mg, 365 μmol) in isopropyl alcohol (50 mL) and triethylamine (255 μL) and a solution of N,N',N'',N'''-[1,2-ethanediylbis(nitrilodi-2,1-ethanediyl)]tetrakis[2-benzyloxy-3-[(2-thioxo-3-thiazolidinyl)carbonyl]benzamide 3 (213 mg, 528 μmol) in dichloromethane (50 mL) were added dropwise to a solution of dichloromethane (1.50 L) and triethylamine (255 μL), degassed three times with N$_2$, over a period of four days using two syringe pumps at a rate of 0.5 mL/hr. After an additional day of reaction, solvent was removed under reduced pressure, and the crude product was purified by silica gel chromatography using 0.1% triethylamine, 2-7.5% isopropyl alcohol in dichloromethane as eluents. Fractions containing product were combined, solvent was removed under reduced pressure, and the residue dried in vacuo to provide the protected bi-macrocycle 5 (167 mg, 31.7%). $^1$H NMR (300 MHz, CDCl$_3$): δ=7.94-6.74 (broad m, 32H, PhH, ArH), 5.00 (s, 2H, PhCH$_2$O), 4.80-4.75 (br s, 6H, PhCH$_2$O), 4.48 (t, 2H, NCH$_2$CH$_2$S), 3.50-3.32 (m, 14H, CH$_2$NC=O), 3.17 (t, 2H, NCH$_2$CH$_2$S), 2.64-2.26 (m, 18H, CH$_2$N). $^{13}$C NMR (600 MHz, CDCl$_3$): δ=201.6, 167.3, 167.0, 166.6, 166.3, 165.5, 164.7, 154.5, 153.3, 153.2, 136.0, 135.1, 134.1, 133.2, 132.7, 131.7, 130.3, 129.4, 129.2, 129.1, 128.8, 128.6, 128.4, 127.7, 127.5, 124.6, 124.4, 79.0, 78.4, 77.7, 72.5, 71.6, 71.2, 70.4, 70.1, 61.8, 55.7, 55.3, 55.0, 54.2, 52.9, 52.4, 51.9, 51.2, 50.2, 48.8, 39.1, 38.3, 37.8, 37.5, 31.6, 29.6, 28.7, 26.6, 19.2, 13.9. FTMS pESI: calculated for $C_{79}H_{84}N_{10}O_{12}S_2$ [M+H]$^+$, 1442.5737, found, 1442.5753.

Benzyl and tert-butyloxycarbonyl-protected bi-macrocycle 7. A solution of benzyl-protected bi-macrocycle 5 (154 mg, 108 μmol) in dry dichloromethane (5 mL) and triethylamine (74 μL) was treated with N-Boc-2,2'-(ethylenedioxy)diethylamine 6 (40 mg, 161 μmol) under N$_2$, and allowed to stir for 28 hr. Solvent was removed under reduced pressure, and the crude product was purified by silica gel chromatography using 0.1% triethylamine, 3.5-5% methanol in dichloromethane as eluents. Fractions containing product were combined, solvent was removed under reduced pressure, and the residue dried in vacuo to provide the protected bi-macrocycle 7 (148 mg, 87%). $^1$H NMR (300 MHz, MeOD): δ=7.8-6.9 (broad m, 32H, PhH, ArH), 5.5 (s, 2H, PhCH$_2$O), 3.6-3.1 (m, 26H, CH$_2$CH$_2$O, CH$_2$NC=O), 2.7-2.4 (m, 18H, CH$_2$N), 1.4 (s, 9H, CH$_3$). $^{13}$C NMR (300 MHz, MeOD): δ=154.4, 153.7, 136.5, 132.5, 132.0, 129.4, 129.0, 128.6, 124.7, 124.5, 79.2, 78.5, 78.1, 70.2, 69.2, 53.9, 50.0, 40.2, 39.8, 39.1, 38.3, 38.0, 27.8. FTMS pESI: calculated for $C_{87}H_{103}N_{12}O_{16}$ [M+H]$^+$, 1571.7610, found, 1571.7667.

Bi-macrocycle 8. Benzyl and tert-butyloxycarbonyl-protected bi-macrocycle 7 (89 mg, 57 μmol) was dissolved in 12N hydrochloric acid (1.5 mL) and glacial acetic acid (1.5 mL). The solution was stirred under inert atmosphere for 26 hr, whereupon HCl was removed with a stream of inert gas. Solvents were removed under reduced pressure and the residue was dried in vacuo. The residue was dissolved in methanol (2000 μL) and transferred to four O-ring microcentrifuge tubes. Ether (ca. 1.5 mL) was added, and the tubes were placed at 4° C. for 1 hr. The tubes were centrifuged at 12,000 rpm for 3 minutes, decanted, the pellets were washed with ether (ca. 1.5 mL) and allowed to air dry. The pellets were dried in vacuo to provide bi-macrocycle 8, tetrahydrochloride salt (58.6 mg, 82%). FTMS pESI: calculated for $C_{54}H_{71}N_{12}O_{14}$ [M+H]$^+$, 1111.5207, found, 1111.5234. Anal: Calculated for $C_{54}H_{84}N_{12}O_{19}Cl_4$, 48.13, 6.29, 12.48; found, 48.15, 6.22, 12.11.

Example 2

Synthesis of an Octa-Coordinating Bi-Macrocyclic Bifunctional Chelator (Scheme 2).

Scheme 2. Synthesis of bi-macrocyclic bifunctional chelator 13.

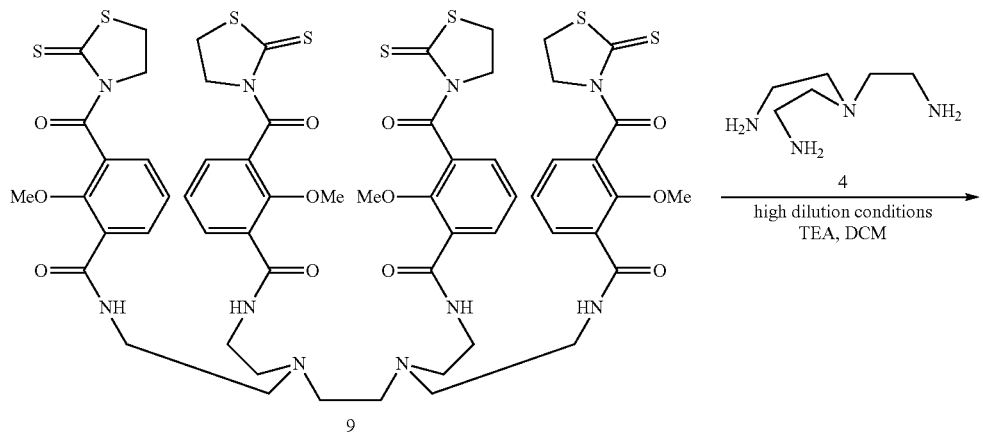

9

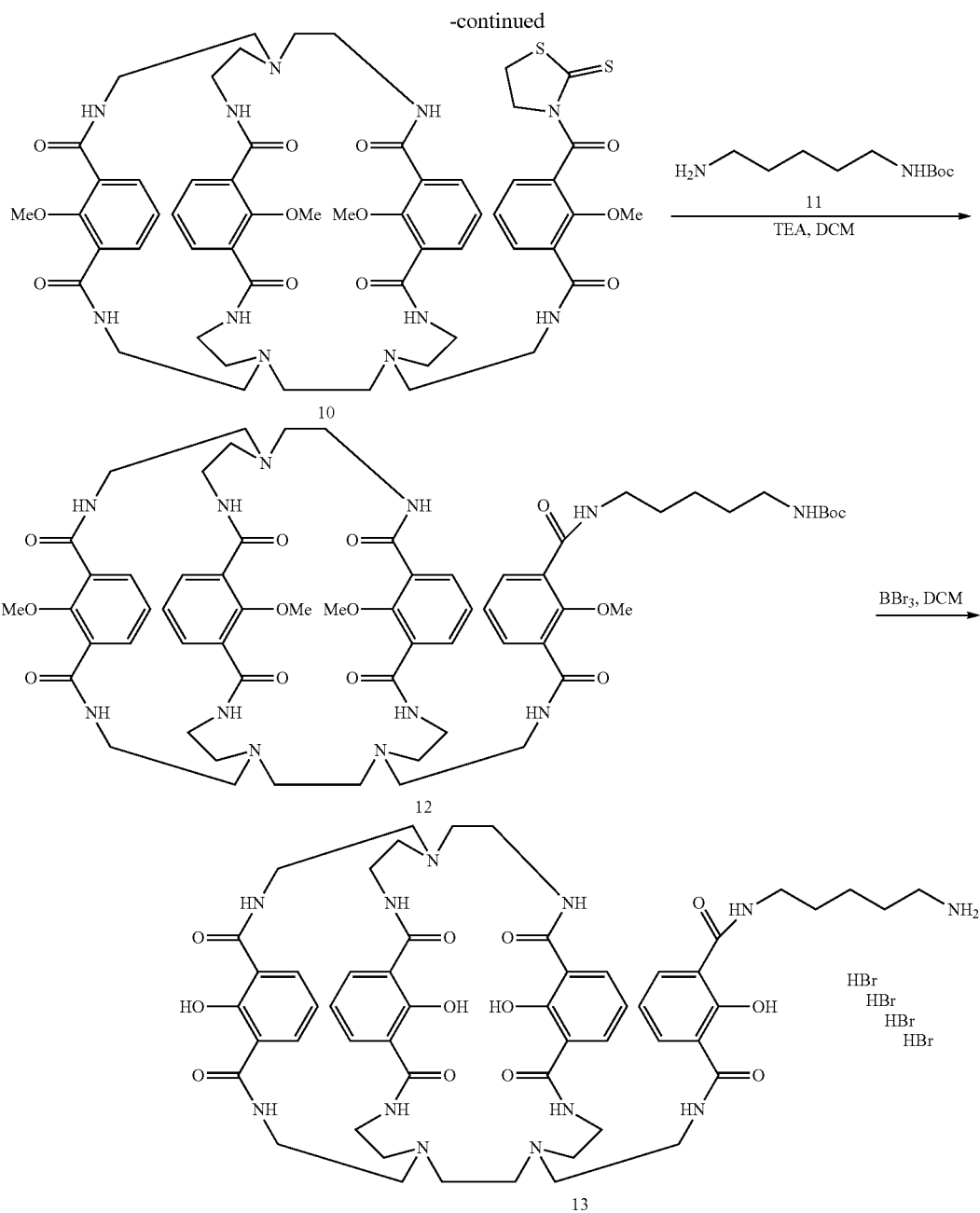

Preparation of an isophthalamide (IAM) bi-macrocyclic ligand began with the activated tetra-amide 9, which was reacted with tris-(2-aminoethyl)amine 4 under high dilution conditions to form the bi-macrocycle 10. The remaining activated amide in 10 was reacted with amine 11 to provide bi-macrocycle 12. Protective groups are removed using a solution of boron tribromide to provide bi-macrocycle 13.

N,N',N'',N'''-[1,2-ethanediylbis(nitrilodi-2,1-ethanediyl)] tetrakis[2-methoxy-3-[(2-thioxo-3-thiazolidinyl)carbonyl] benzamide 9 was synthesized as described (Patoud, S., et al., J. Am. Chem. Soc. 2003, 125, 13324-13325).

Methyl-protected bi-macrocycle 10. A solution of tris-(2-aminoethyl)amine 4 (25 mg, 173 μmol) in isopropyl alcohol (25 mL) and triethylamine (121 μL) and a solution of N,N',N'',N'''-[1,2-ethanediylbis(nitrilodi-2,1-ethanediyl)] tetrakis{2-methyloxy-3-[(2-thioxo-3-thiazolidinyl)carbonyl]benzamide} 9 (585 mg, 433 μmol) in dichloromethane (25 mL) were added dropwise to a solution of dichloromethane (866 mL) and triethylamine (121 μL), degassed three times with $N_2$, over a period of four days using two syringe pumps at a rate of 0.5 mL/hr. After an additional day of reaction, solvent was removed under reduced pressure, and the crude product was purified by silica gel chromatography using 0.1% triethylamine, 5-15% isopropyl alcohol in dichloromethane as eluents. Fractions containing product were combined, solvent was removed under reduced pressure, and the residue dried in vacuo to provide the protected bi-macrocycle 10 (102 mg, 51.8%). $^1$H NMR (300 MHz, $CDCl_3$): δ=7.9-6.9 (broad m, 12H, ArH), 4.61 (t, 2H, $NCH_2CH_2S$), 3.78 (s, 3H, $CH_3O$), 3.74 (s, 3H, $CH_3O$), 3.70

(s, 6H, CH₃O), 3.7-3.4 (m, 14H, CH₂NC=O), 2.88 (t, 2H, NCH₂CH₂S), 2.8-2.6 (m, 18H, CH₂N). FTMS pESI: calculated for $C_{55}H_{68}N_{10}O_{12}S_2$ [M+H]⁺, 1138.4485, found, 1138.4478.

Methyl and tert-butyloxycarbonyl-protected bi-macrocycle 12. A solution of methyl-protected bi-macrocycle 10 (90 mg, 79 μmol) in dry dichloromethane (5 mL) and triethylamine (55 μL) was treated with N-Boc-cadavarine 11 (24 mg, 120 μmol) under N₂, and allowed to stir for 2 hr. Solvent was removed under reduced pressure, and the crude product was purified by silica gel chromatography using 0.1% triethylamine, 2-5% methanol in dichloromethane as eluents. Fractions containing product were combined, solvent was removed under reduced pressure, and the residue dried in vacuo to provide the protected bi-macrocycle 12 (79 mg, 82%). ¹H NMR (300 MHz, MeOD): δ=7.7-7.0 (m, 12H, ArH), 3.80 (s, 3H, CH₃O), 3.75 (s, 3H, CH₃O), 3.67 (s, 6H, CH₃O), 3.6-3.4 (m, 18H, CH₂NC=O), 3.0-2.7 (m, 18H, CH₂N), 1.5-1.3 (m, 6H, CH₂), 1.40 (s, 9H, CH₃). ¹³C NMR (300 MHz, MeOD): δ=166.2, 155.8, 133.5, 132.4, 129.4, 127.7, 124.5, 124.2, 78.9, 62.9, 52.4, 38.0, 29.4, 29.0, 27.8, 24.1, 15.0, 8.2. FTMS pESI: calculated for $C_{62}H_{85}N_{12}O_{14}$ [M+H]⁺, 1221.6303, found, 1221.6330.

Bi-macrocycle 13. Methyl and tert-butyloxycarbonyl-protected bi-macrocycle 12 (79 mg, 65 μmol) is dissolved in dichloromethane (8 mL) in a Schlenk flask with a Teflon stopcock. Under a flow of nitrogen gas, the solution is cooled to −10° C. and then treated with boron tribromide (993 mg, 3.96 mmol). The solution is stirred under inert atmosphere for 5 days, whereupon boron tribromide and dichloromethane are removed under reduced pressure. The residue is dissolved in methanol (38 mL) and heated at reflux for six hours. Methanol is removed under reduced pressure, and the residue is dissolved in methanol (4 mL) and water 20 mL). The solution is boiled until the volume is reduced to ca. 4 mL, whereupon the solution is allowed to cool to ambient temperature. The resulting precipitate is collected by centrifugation and dried in vacuo to provide bi-macrocycle 13, tetrahydrobromide.

Example 3

Synthesis of an Octa-Coordinating Bi-Macrocyclic Bifunctional Chelator (Scheme 3).

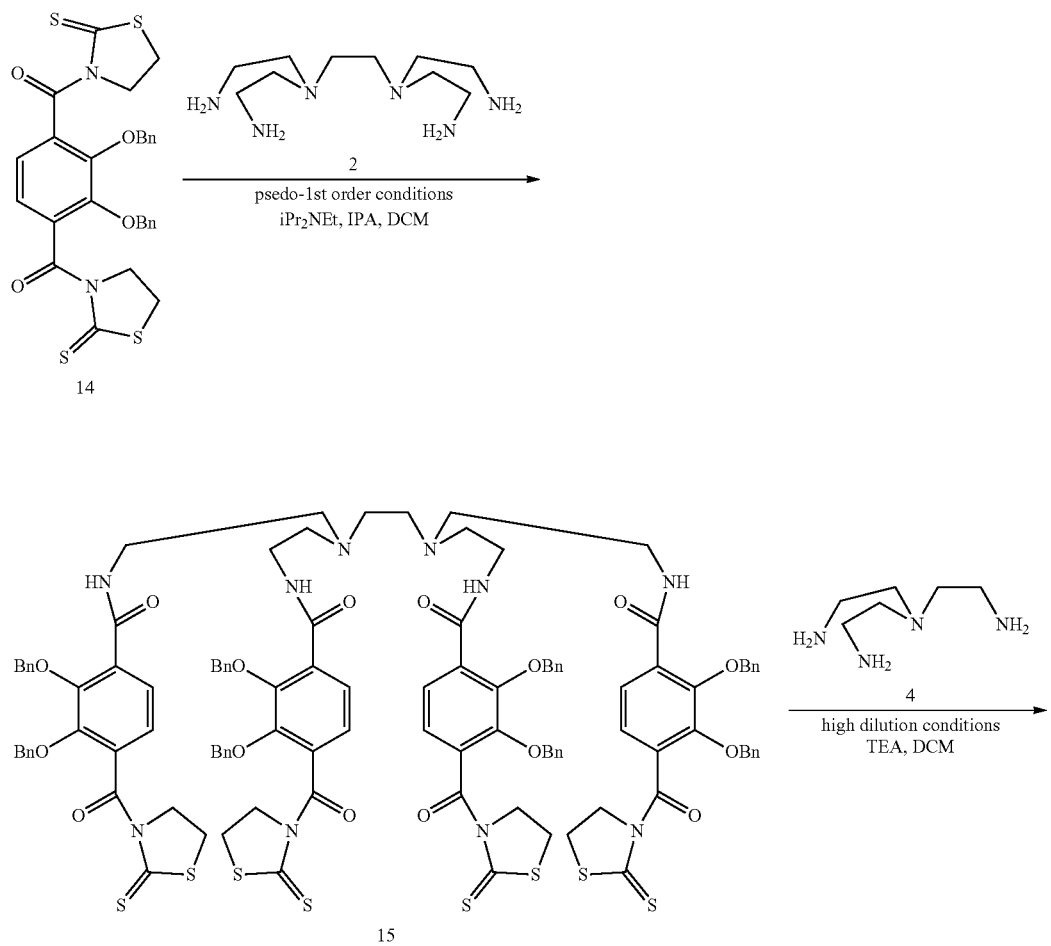

Scheme 3. Synthesis of bi-macrocyclic bifunctional chelator 18.

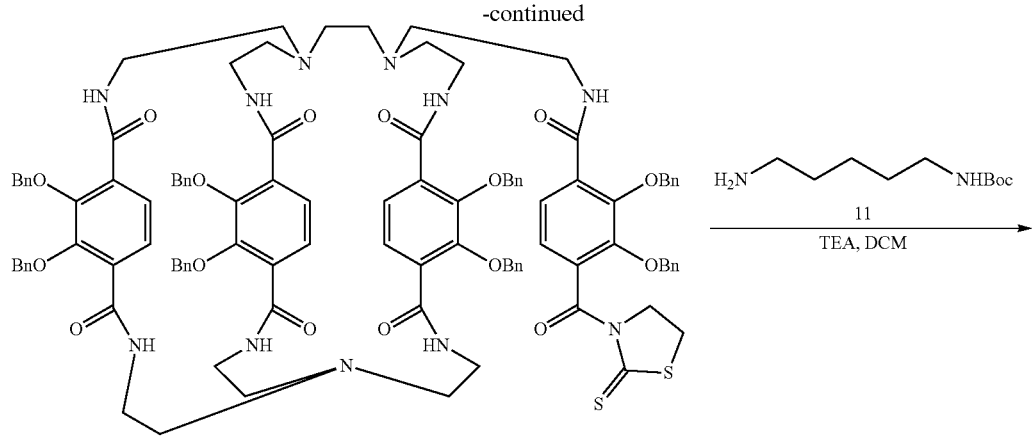

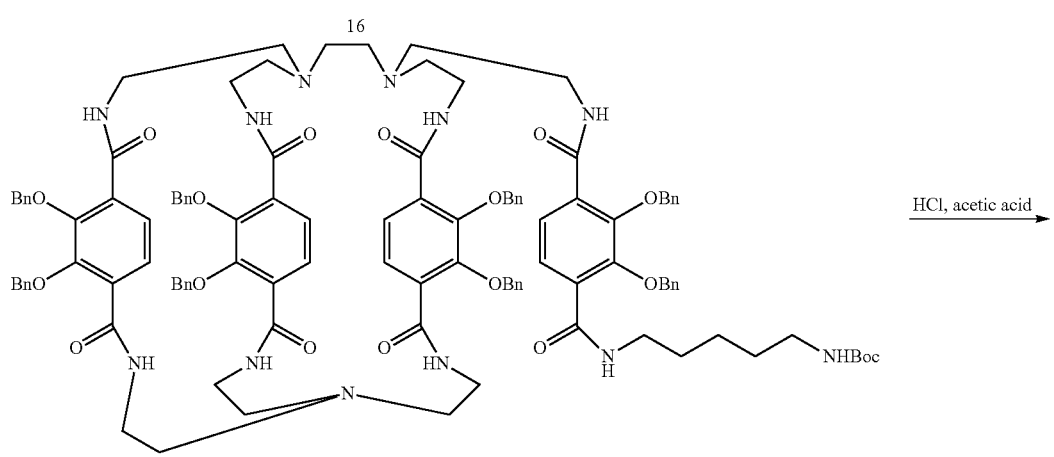

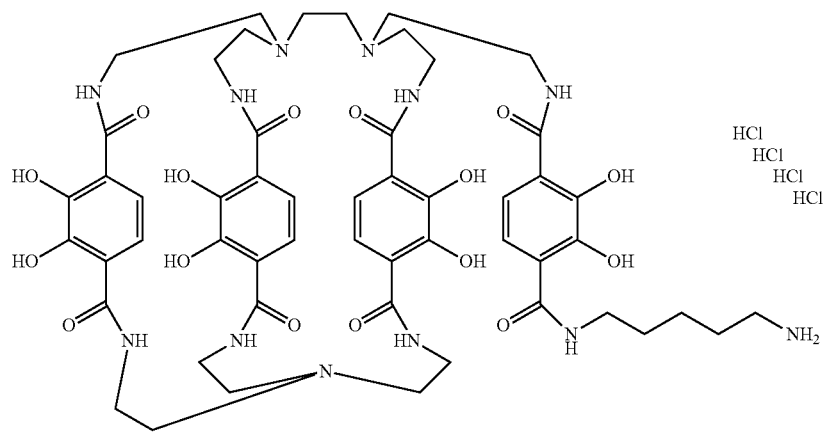

Preparation of a terephthalamide (TAM) bi-macrocyclic ligand began with 2,3-dibenzyloxy-bis(2-mercaptothiazolide)terephthalamide 14, which was condensed with tetrakis-(2-aminoethyl) ethylene diamine 2 under pseudo-first order conditions to provide the activated tetra-amide 15, which was reacted with tris-(2-aminoethyl)amine 4 under high dilution conditions to form the bi-macrocycle 16. The remaining activated amide in 16 was reacted with amine 11 to provide bi-macrocycle 17. Protective groups were removed using a solution of concentrated hydrochloric acid in acetic acid to provide bi-macrocycle 18.

2,3-Dibenzyloxy-bis(2-mercaptothiazolide)terephthalamide 14 was synthesized as described (Doble, D. M. J., et al., *Inorg. Chem.* 2003, 42, 4930-4937).

N,N',N'',N'''-[1,2-ethanediylbis(nitrilodi-2,1-ethanediyl)] tetrakis {2,3-benzyloxy-4-[(2-thioxo-3-thiazolidinyl)carbonyl]benzamide} 15. Tetrakis-(2-aminoethyl) ethylene diamine 2 (280 mg, 1.21 mmol) was dissolved in ca. 10% isopropyl alcohol in dichloromethane (48 mL) dichloromethane (anhydrous, 100 mL) and triethylamine (843 L, 6.05 mmol) over a period of 43 hrs at a rate of 1.50 mL/hr. After a further 24 hr, solvent was removed under reduced pressure, and the crude product was purified by silica gel chromatography using 0.1% triethylamine, 2-5% isopropyl alcohol in dichloromethane as eluents. Fractions containing product were combined, solvent was removed under reduced pressure, and the residue dried in vacuo to provide compound 15 (811 mg, 32.2%). $^1$H NMR (300 MHz, CDCl$_3$): δ=7.79 (t, 4H, NH), 7.73 (d, 4H, ArH), 7.35-7.27 (m, 40H, PhH), 7.16 (d, 4H, ArH), 5.08 (s, 16H, PhCH$_2$O), 4.35 (t, 8H, NCH$_2$CH$_2$S), 3.21 (m, 8H, CH$_2$NC=O), 2.91 (t, 8H, NCH$_2$CH$_2$S), 2.37 (m, 12H, CH$_2$N). $^{13}$C NMR (600 MHz, CDCl$_3$): δ=201.2, 166.8, 164.3, 150.0, 149.3, 137.0, 135.8, 133.2, 130.6, 128.8, 128.7, 128.6, 128.3, 127.9, 126.4, 124.4, 76.1, 55.5, 53.2, 37.7, 28.7. FTMS pESI: calculated for C$_{110}$H$_{106}$N$_{10}$O$_{16}$S$_8$ [M+2H]$^{2+}$, 1039.2772, found, 1039.2788.

Benzyl-protected bi-macrocycle 16. A solution of tris-(2-aminoethyl)amine 4 (23 mg, 159 μmol) in methanol (25 mL) and triethylamine (111 μL) and a solution of N,N',N'',N'''-[1,2-ethanediylbis(nitrilodi-2,1-ethanediyl)]tetrakis[2,3-benzyloxy-4-[(2-thioxo-3-thiazolidinyl)carbonyl]benzamide 15 (827 mg, 398 μmol) in dichloromethane (25 mL) were added dropwise to a solution of dichloromethane (1.00 L) and triethylamine (111 μL), degassed three times with N$_2$, over a period of three days using two syringe pumps at a rate of 0.5 mL/hr. After an additional two days of reaction, solvent was removed under reduced pressure, and the crude product was purified by silica gel chromatography using 0.1% triethylamine, 2-3.5% methanol in dichloromethane as eluents. Fractions containing product were combined, solvent was removed under reduced pressure, and the residue dried in vacuo to provide the protected bi-macrocycle 16 (153 mg, 51.4%). $^1$H NMR (600 MHz, CDCl$_3$): δ=7.99 (br s, 1H, NH), 7.83 (m, 2H, NH), 7.77 (br s, 1H, NH), 7.56 (m, 4H, ArH), 7.4-7.0 (broad m, 40H, PhH), 6.82-6.76 (m, 4H, ArH), 5.10-4.74 (m, 16H, PhCH$_2$O), 4.37 (t, 2H, NCH$_2$CH$_2$S), 3.35-3.10 (m, 14H, CH$_2$NC=O), 2.93 (t, 2H, NCH$_2$CH$_2$S), 2.53-2.32 (m, 18H, CH$_2$N). $^{13}$C NMR (600 MHz, CDCl$_3$): δ=201.4, 166.8, 166.6, 166.1, 165.7, 165.5, 164.4, 150.8, 150.4, 150.2, 150.1, 150.0, 149.4, 136.9, 136.8, 136.6, 136.5, 136.4, 135.9, 133.3, 132.9, 130.9, 130.7, 130.5, 128.9, 128.8, 128.6, 128.5, 128.4, 128.3, 128.2, 127.9, 126.5, 125.1, 124.9, 124.8, 124.4, 123.9, 76.6, 76.5, 76.1, 55.5, 54.1, 53.7, 52.9, 51.6, 45.8, 37.7, 37.5, 37.3, 29.7, 28.7. FTMS pESI: calculated for C$_{107}$H$_{108}$N$_{11}$O$_{16}$S$_2$ [M+H]$^+$, 1866.7411, found, 1866.7430.

Benzyl and tert-butyloxycarbonyl-protected bi-macrocycle 17. A solution of benzyl-protected bi-macrocycle 16 (90 mg, 48 μmol) in dry dichloromethane (5 mL) and triethylamine (33 μL) was treated with N-Boc-cadavarine 11 (15 mg, 72 μmol) under N$_2$, and allowed to stir for 23 hr. Solvent was removed under reduced pressure, and the crude product was purified by silica gel chromatography using 0.1% triethylamine, 3.5% methanol in dichloromethane as eluent. Fractions containing product were combined, solvent was removed under reduced pressure, and the residue dried in vacuo to provide the protected bi-macrocycle 17 (75 mg, 80%). $^1$H NMR (300 MHz, MeOD): δ=7.5-7.2 (broad m, 40H, PhH), 7.04 (d of d, 2H, ArH), 6.47 (d of d, 6H, ArH), 5.06-4.45 (m, 16H, PhCH$_2$O), 3.5-2.9 (m, 18H, CH$_2$NC=O), 2.8-2.3 (m, 18H, CH$_2$N), 1.41 (s, 9H, CH$_3$), 1.4-1.3 (m, 6H, CH$_2$). $^{13}$C NMR (600 MHz, MeOD): δ=167.3, 166.9, 166.7, 166.6, 166.3, 157.0, 150.9, 150.2, 150.1, 136.8, 136.7, 136.5, 133.7, 133.3, 132.4, 131.9, 131.8, 128.6, 128.4, 128.3, 128.2, 128.1, 128.0, 127.8, 125.0, 124.6, 124.5, 124.4, 98.5, 79.8, 78.4, 76.5, 76.2, 76.0, 54.4, 54.0, 52.8, 52.6, 51.6, 49.9, 46.5, 39.8, 39.5, 38.4, 37.7, 37.4, 37.0, 29.2, 28.6, 27.4, 23.9, 7.9. FTMS pESI: calculated for C$_{114}$H$_{125}$N$_{12}$O$_{18}$ [M+H]$^+$, 1949.9229, found, 1949.9270.

Bi-macrocycle 18. Benzyl and tert-butyloxycarbonyl-protected bi-macrocycle 17 (62 mg, 32 μmol) was dissolved in 12N hydrochloric acid (1.0 mL) and glacial acetic acid (1.0 mL). The solution was stirred under inert atmosphere for 27 hr, whereupon HCl was removed with a stream of inert gas. Solvents were removed under reduced pressure and the residue was dried in vacuo. The residue was dissolved in methanol (2000 μL) and transferred to three O-ring microcentrifuge tubes. Ether (ca. 1.5 mL) was added, and the tubes were placed at 4° C. for 1 hr. The tubes were centrifuged at 12,000 rpm for 3 minutes, decanted, the pellets were washed with ether (ca. 1.5 mL) and allowed to air dry. The pellets were dried in vacuo to provide bi-macrocycle 18, tetrahydrochloride salt (36.1 mg, 89%). FTMS pESI: calculated for C$_{53}$H$_{69}$N$_{12}$O$_{16}$ [M+H]$^+$, 1129.4949, found, 1129.4975.

Example 4

Synthesis of an Octa-Coordinating Bi-Macrocyclic Bifunctional Chelator (Scheme 4).

Scheme 4. Synthesis of bi-macrocyclic bifunctional chelator 20.

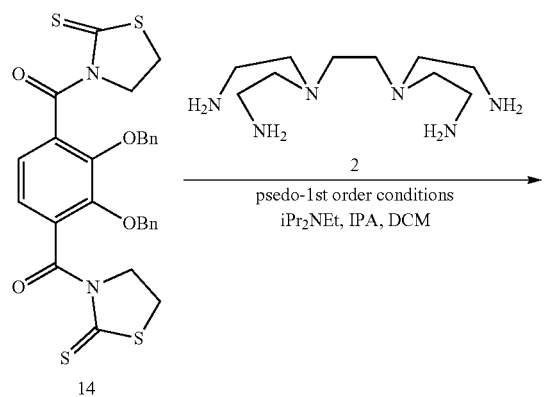

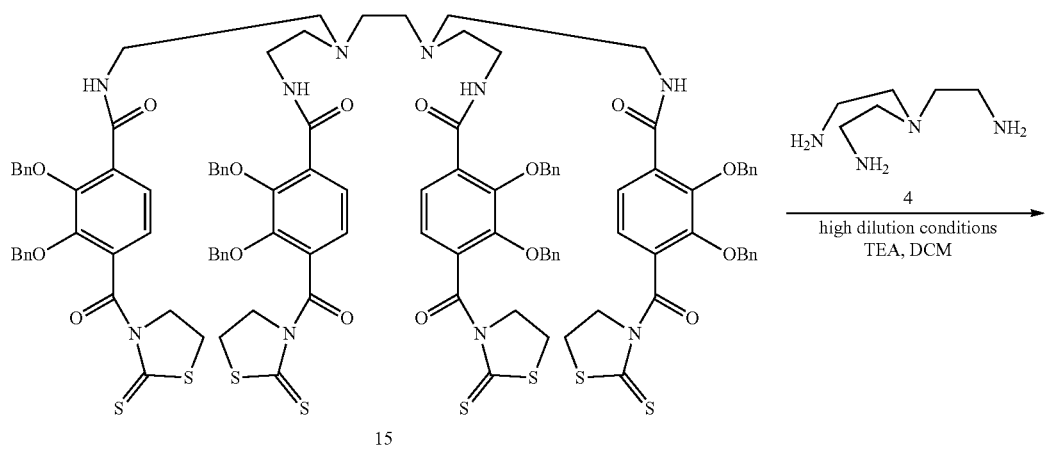
15
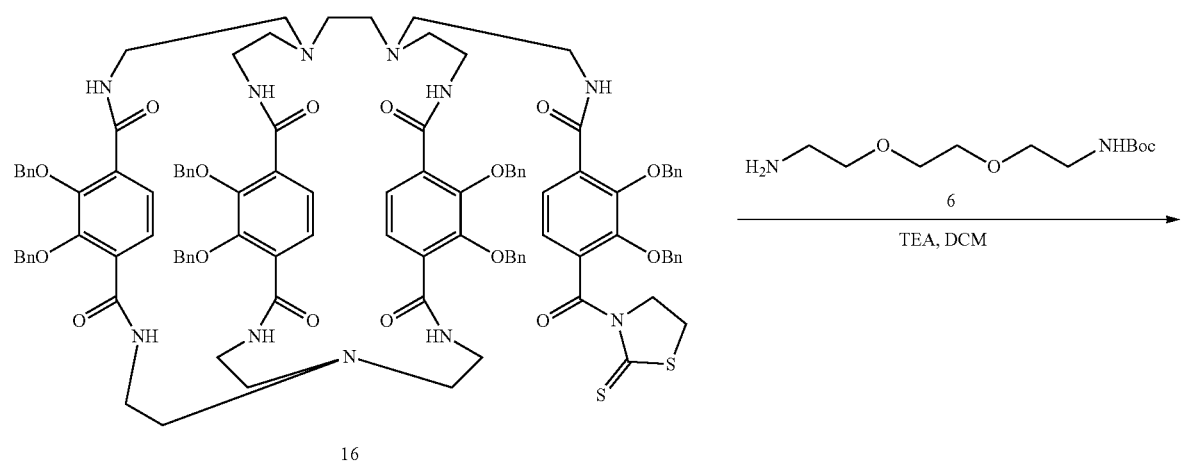
16
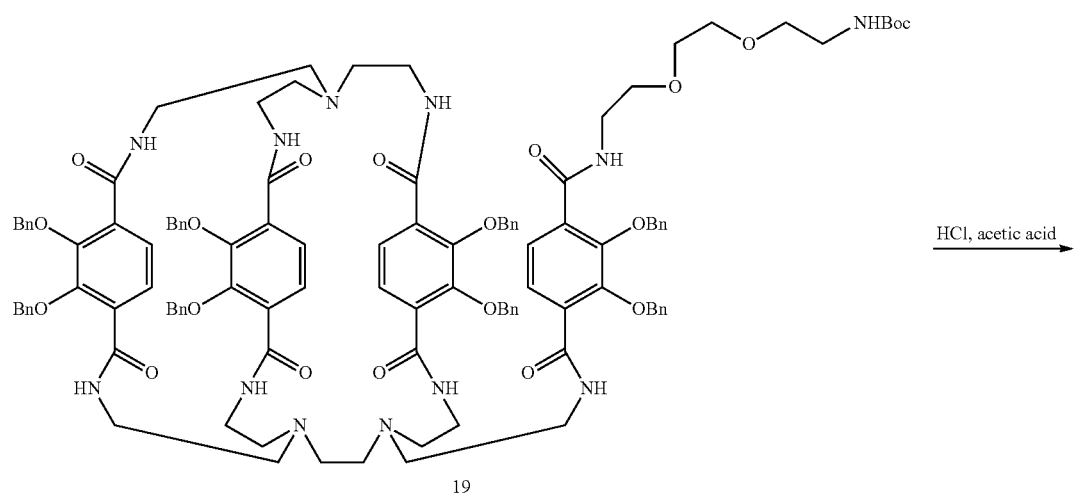
19

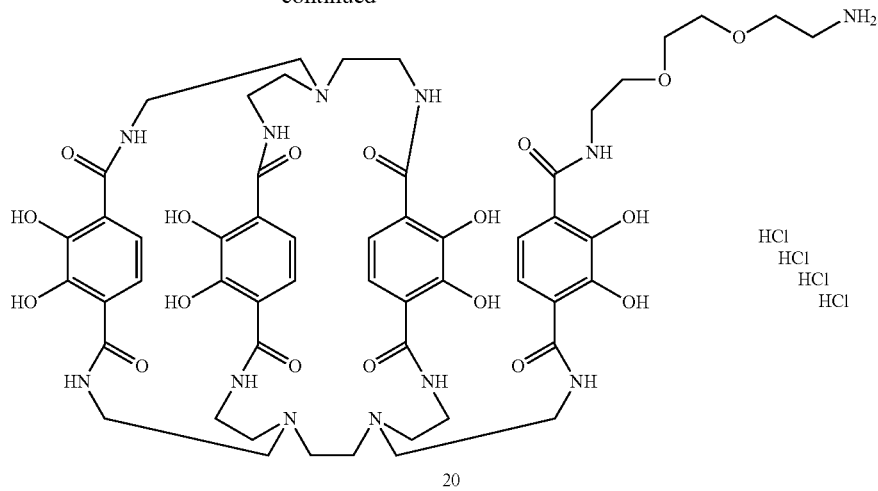

20

Benzyl and tert-butyloxycarbonyl-protected bi-macrocycle 19. A solution of benzyl-protected bi-macrocycle 16 (171 mg, 91.6 μmol) in dry dichloromethane (5 mL) and triethylamine (64 μL) was treated with N-Boc-2,2'-(ethylenedioxy)diethylamine 6 (34 mg, 137 mol) under $N_2$, and allowed to stir for 24 hr. Solvent was removed under reduced pressure, and the crude product was purified by silica gel chromatography using 0.1% triethylamine, 3.5-5% methanol in dichloromethane as eluent. Fractions containing product were combined, solvent was removed under reduced pressure, and the residue dried in vacuo to provide the protected bi-macrocycle 19 (145 mg, 80%). $^1$H NMR (300 MHz, MeOD): δ=8.5-7.2 (broad m, 40H, PhH), 7.05 (d of d, 2H, ArH), 6.50 (d of d, 6H, ArH), 5.04-4.42 (m, 16H, PhCH$_2$O), 3.5-2.9 (m, 26H, CH$_2$O, CH$_2$NC=O), 2.8-2.3 (m, 18H, CH$_2$N), 1.36 (s, 9H, CH$_3$). $^{13}$C NMR (600 MHz, MeOD): δ=167.3, 167.1, 166.9, 166.8, 166.6, 166.3, 166.2, 158.4, 157.1, 150.9, 150.2, 150.1, 136.7, 136.6, 136.3, 136.2, 133.6, 133.1, 132.6, 132.0, 131.7, 128.6, 128.4, 128.3, 128.2, 128.1, 127.9, 124.9, 124.4, 124.1, 122.9, 78.8, 76.5, 76.3, 76.0, 69.8, 69.7, 69.6, 68.8, 54.4, 53.9, 52.8, 51.5, 50.0, 46.5, 39.8, 39.4, 38.8, 38.7, 37.7, 37.1, 31.4, 27.4, 18.9, 8.0. FTMS pESI: calculated for $C_{115}H_{127}N_{12}O_{20}$ [M+H]$^+$, 1995.9284, found, 1995.9369.

Bi-macrocycle 20. Benzyl and tert-butyloxycarbonyl-protected bi-macrocycle 19 (94 mg, 47 μmol) was dissolved in 12N hydrochloric acid (1.5 mL) and glacial acetic acid (1.5 mL). The solution was stirred under inert atmosphere for 29 hr, whereupon HCl was removed with a stream of inert gas. Solvents were removed under reduced pressure and the residue was dried in vacuo. The residue was dissolved in dimethylformamide (350 μL) and methanol (2100 μL) and transferred to six O-ring microcentrifuge tubes. Ether (ca. 1.5 mL) was added, and the tubes were placed at 4° C. for 1 hr. The tubes were centrifuged at 12,000 rpm for 3 minutes, decanted, the pellets were washed with ether (ca. 2 mL) and allowed to air dry. The pellets were dried in vacuo to provide bi-macrocycle 20, tetrahydrochloride salt (61 mg, 98%). FTMS pESI: calculated for $C_{54}H_{72}N_{12}O_{18}$ [M+H]$^+$, 1175.5009, found, 1175.5064. Anal: Calculated for $C_{54}H_{82}N_{12}O_{22}Cl_4$, 46.54, 5.94, 12.07; found, 46.34, 6.01, 11.89.

Example 5

Synthesis of an Octa-Coordinating Bi-Macrocyclic Bifunctional Chelator (Scheme 5).

Scheme 5. Synthesis of bi-macrocyclic bifunctional chelator 25.

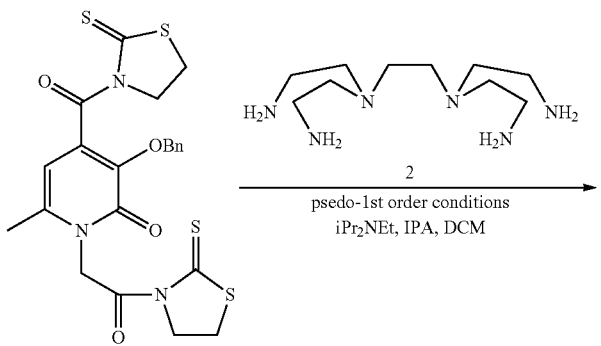

21

-continued
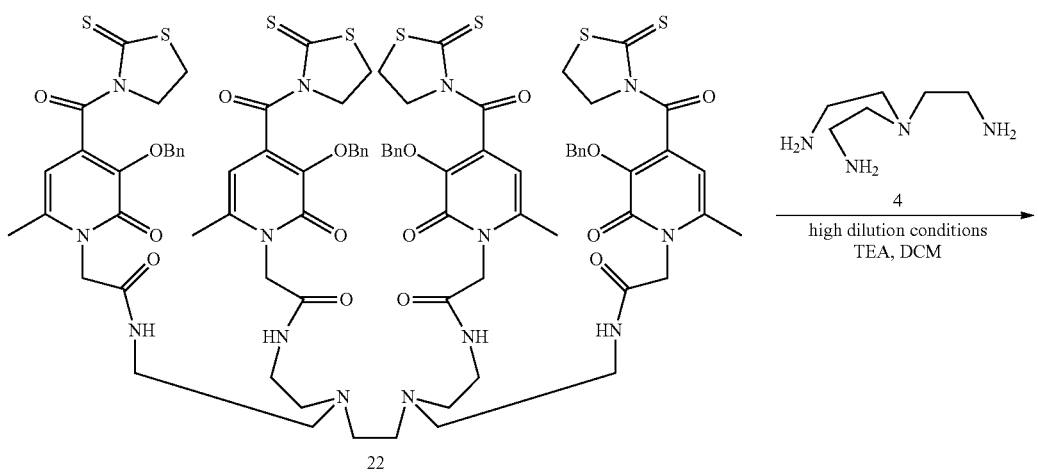
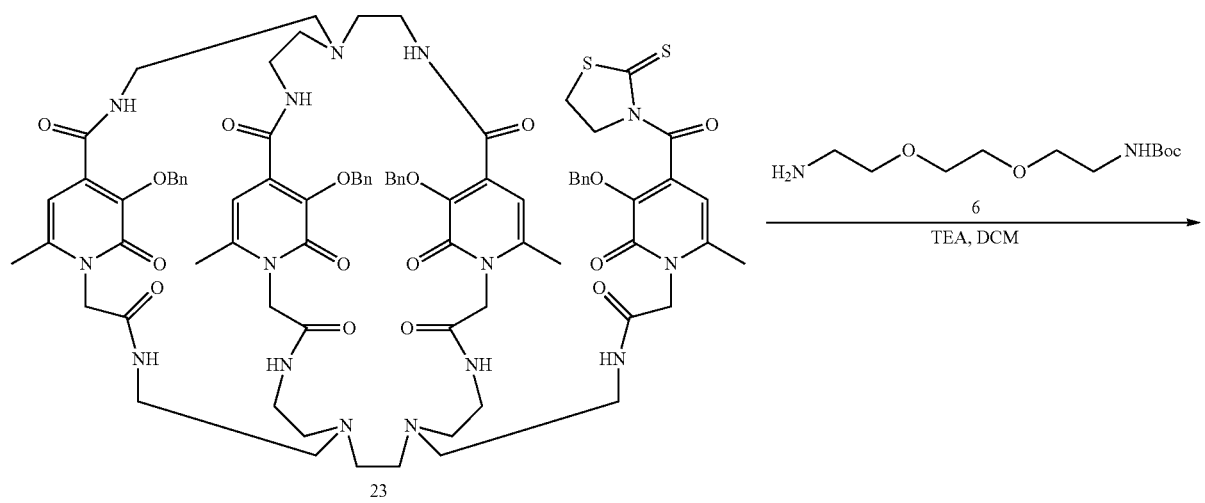
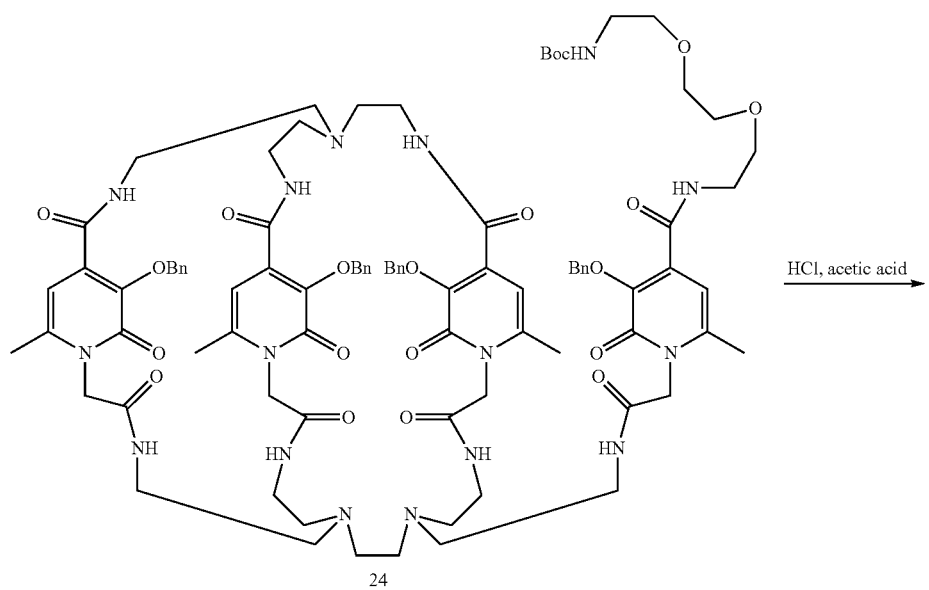

-continued

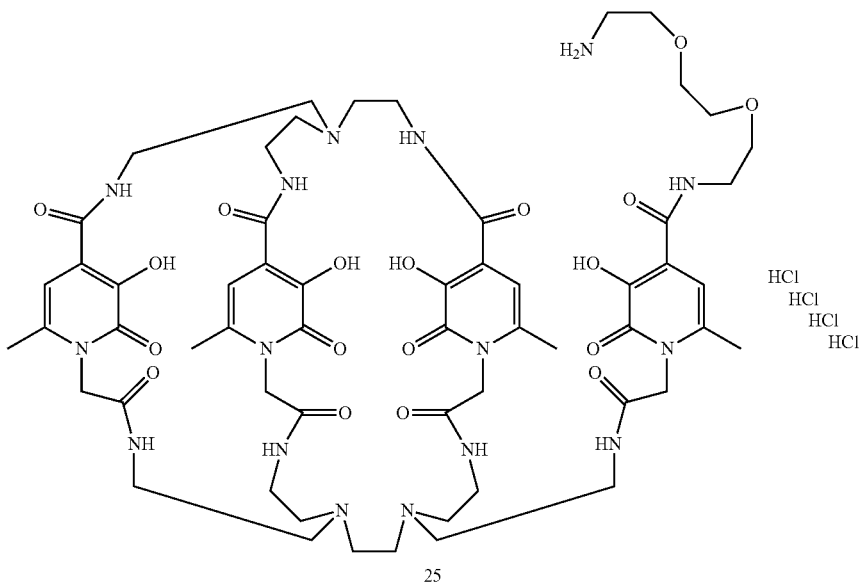

25

Preparation of a 3-hydroxy-2-oxo-pyridine (3,2-HOPO) bi-macrocyclic ligand began with 3-benzyloxy-1-carbonyl (2-mercaptothiazolide)methyl-6-methyl-2-oxo-1,2-dihydro-pyridine-4-carbonyl(2-mercaptothiazolide) 21, which was condensed with tetrakis-(2-aminoethyl) ethylene diamine 2 under pseudo-first order conditions to provide the activated tetra-amide 22, which was reacted with tris-(2-aminoethyl) amine 4 under high dilution conditions to form the bi-macrocycle 23. The remaining activated amide in 23 was reacted with amine 6 to provide bi-macrocycle 24. Protective groups were removed using a solution of concentrated hydrochloric acid in acetic acid to provide bi-macrocycle 25.

3-Benzyloxy-1-carbonyl(2-mercaptothiazolide)methyl-6-methyl-2-oxo-1,2-dihydropyridine-4-carbonyl(2-mercaptothiazolide) 21 was synthesized as described (PCT/US13/70356).

N,N',N'',N'''-[1,2-ethanediylbis(nitrilodi-2,1-ethanediyl)] tetrakis[3-benzyloxy-1-carbamidomethyl-6-methyl-2-oxo-1,2-dihydropyridine-4-carbonyl(2-mercaptothiazolide)] 22. Tetrakis-(2-aminoethyl) ethylene diamine 2 (257 mg, 1.10 mmol) was dissolved in ca. 10% isopropyl alcohol in anhydrous dichloromethane (40 mL) and diisopropylethylamine (958 µL, 5.50 mmol) and added using a syringe pump (NE1000) to a solution of 3-benzyloxy-1-carbonyl(2-mercaptothiazolide)methyl-6-methyl-2-oxo-1,2-dihydropyridine-4-carbonyl(2-mercaptothiazolide) 21 (2.87 g, 5.52 mmol) in dichloromethane (anhydrous, 50 mL) over a period of 45 hrs at a rate of 1.00 mL/hr. After a further 24 hr, solvent was removed under reduced pressure, and the crude product was purified by silica gel chromatography using 0.1% triethylamine, 5-7.5% isopropyl alcohol in dichloromethane as eluents. Fractions containing product were combined, solvent was removed under reduced pressure, and the residue dried in vacuo to provide compound 22 (637 mg, 31.6%). $^1$H NMR (600 MHz, CDCl$_3$): δ=7.38-7.26 (m, 20H, PhH), 5.97 (s, 4H, ArH), 5.16 (s, 8H, PhCH$_2$O), 4.74 (s, 8H, CH$_2$C=O), 4.42 (t, 8H, NCH$_2$CH$_2$S), 3.3-3.1 (m, 8H, CH$_2$NC=O), 2.90 (t, 8H, NCH$_2$CH$_2$S), 2.6-2.4 (m, 12H, CH$_2$N), 2.28 (s, 12H, CH$_3$). $^{13}$C NMR (600 MHz, CDCl$_3$): δ=200.8, 167.1, 165.8, 159.7, 142.0, 141.2, 137.5, 133.5, 128.4, 128.1, 128.0, 104.1, 73.8, 55.1, 53.9, 51.3, 48.1, 45.8, 33.6, 29.1, 20.5, 8.8. FTMS pESI: calculated for $C_{86}H_{93}N_{14}O_{16}S_8$ [MH]$^+$, 1834.4688, found, 1834.4684.

Benzyl-protected bi-macrocycle 23. A solution of tris-(2-aminoethyl)amine 4 (23.1 mg, 158 µmol) in isopropyl alcohol (30 mL) and triethylamine (110 µL) and a solution of N,N',N'',N'''-[1,2-ethanediylbis(nitrilodi-2,1-ethanediyl)] tetrakis[3-benzyloxy-1-carbamidomethyl-6-methyl-2-oxo-1,2-dihydropyridine-4-carbonyl(2-mercaptothiazolide)] 22 (579 mg, 316 µmol) in anhydrous dichloromethane (30 mL) were added dropwise to a solution of anhydrous dichloromethane (600 mL) and triethylamine (110 µL), degassed three times with N$_2$, over a period of 2.5 days using two syringe pumps at a rate of 0.5 mL/hr. After an additional day of reaction, solvent was removed under reduced pressure, and the crude product was purified by silica gel chromatography using 0.1% triethylamine, 5-30% isopropyl alcohol in dichloromethane as eluents. Fractions containing product were combined, solvent was removed under reduced pressure, and the residue dried in vacuo to provide the protected bi-macrocycle 23 (257 mg) along with apparent triethylammonium salts. The crude product was used in the next step without further purification. FTMS pESI: calculated for $C_{83}H_{96}N_{15}O_{16}S_2$ [M+H]$^+$, 1622.6595, found, 1622.6641.

Benzyl and tert-butyloxycarbonyl-protected bi-macrocycle 24. A solution of crude benzyl-protected bi-macrocycle 23 (257 mg, 158 µmol) in dry dichloromethane (5 mL) and triethylamine (110 µL) was treated with N-Boc-2,2'-(ethylenedioxy)diethylamine 6 (39 mg, 158 mol) under N$_2$, and allowed to stir for 21 hr. Solvent was removed under reduced pressure, and the crude product was purified by silica gel chromatography using 0.1% triethylamine, 5-7.5% methanol in dichloromethane as eluents. Fractions containing product were combined, solvent was removed under reduced pressure, and the residue dried in vacuo to provide the protected bi-macrocycle 24 (70 mg, 25%). FTMS pESI: calculated for $C_{91}H_{115}N_{16}O_{20}$ [M+H]$^+$, 1751.8468, found, 1751.8493.

Bi-macrocycle 25. Benzyl and tert-butyloxycarbonyl-protected bi-macrocycle 24 (65 mg, 37 µmol) was dissolved in 12N hydrochloric acid (1.0 mL) and glacial acetic acid (1.0 mL). The solution was stirred under inert atmosphere for 24 hr, whereupon HCl was removed with a stream of inert gas. Solvents were removed under reduced pressure and the residue was dried in vacuo. The residue was dissolved in methanol (1800 μL) and transferred to four O-ring micro-centrifuge tubes. Ether (ca. 1.5 mL) was added, and the tubes were placed at 4° C. for 3 hr. The tubes were centrifuged at 12,000 rpm for 3 minutes, decanted, the pellets were washed with ether (ca. 1.5 mL) and allowed to air dry. The pellets were dried in vacuo to provide bi-macrocycle 25, tetrahydrochloride salt (37 mg, 69%). FTMS pESI: calculated for $C_{58}H_{83}N_{16}O_{18}$ [M+H]$^+$, 1291.6066, found, 1291.6080.

Example 6

Synthesis of a Hexa-Coordinating Mono-Macrocyclic Bifunctional Chelator (Scheme 6).

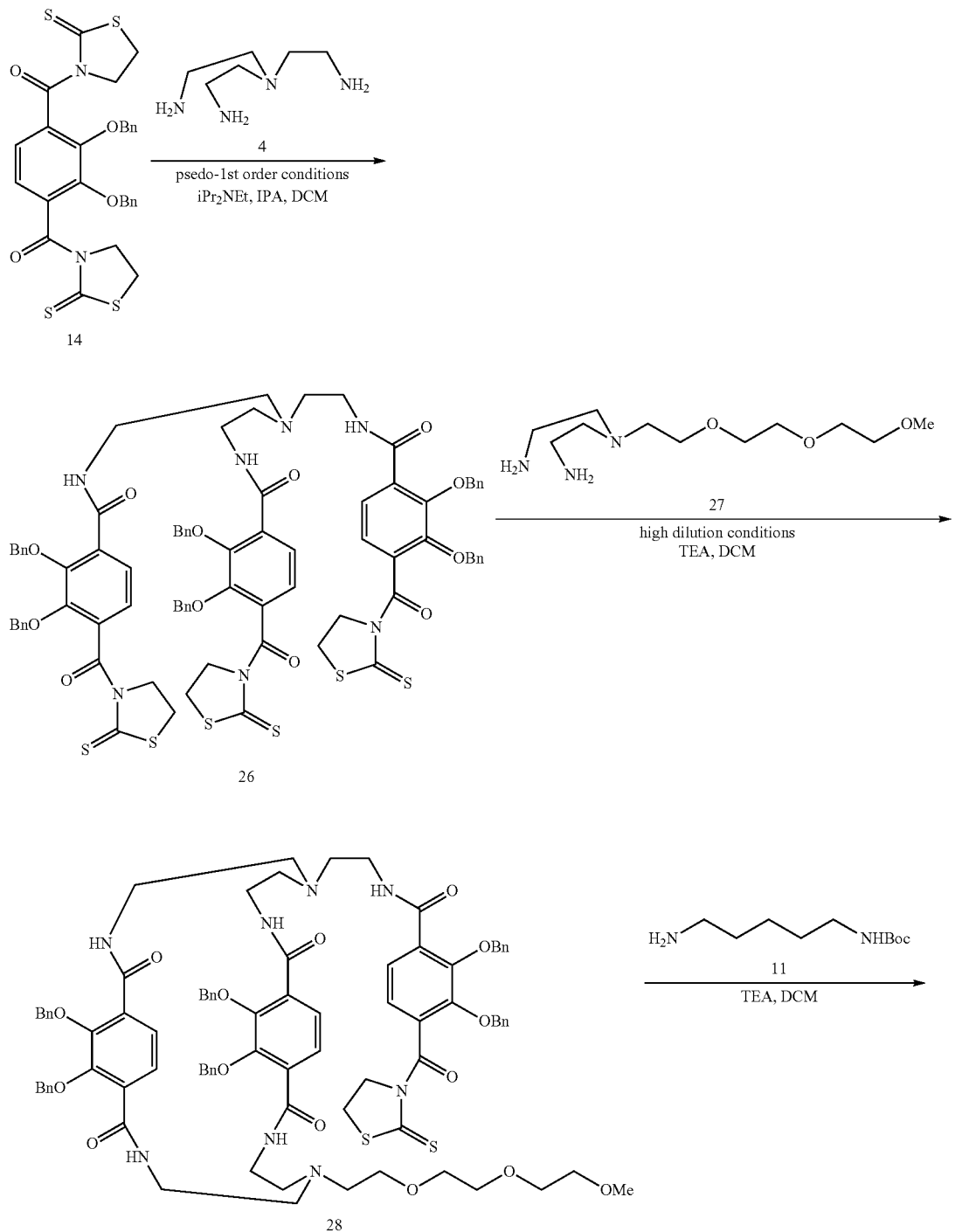

Scheme 6. Synthesis of mono-macrocyclic bifunctional chelator 30.

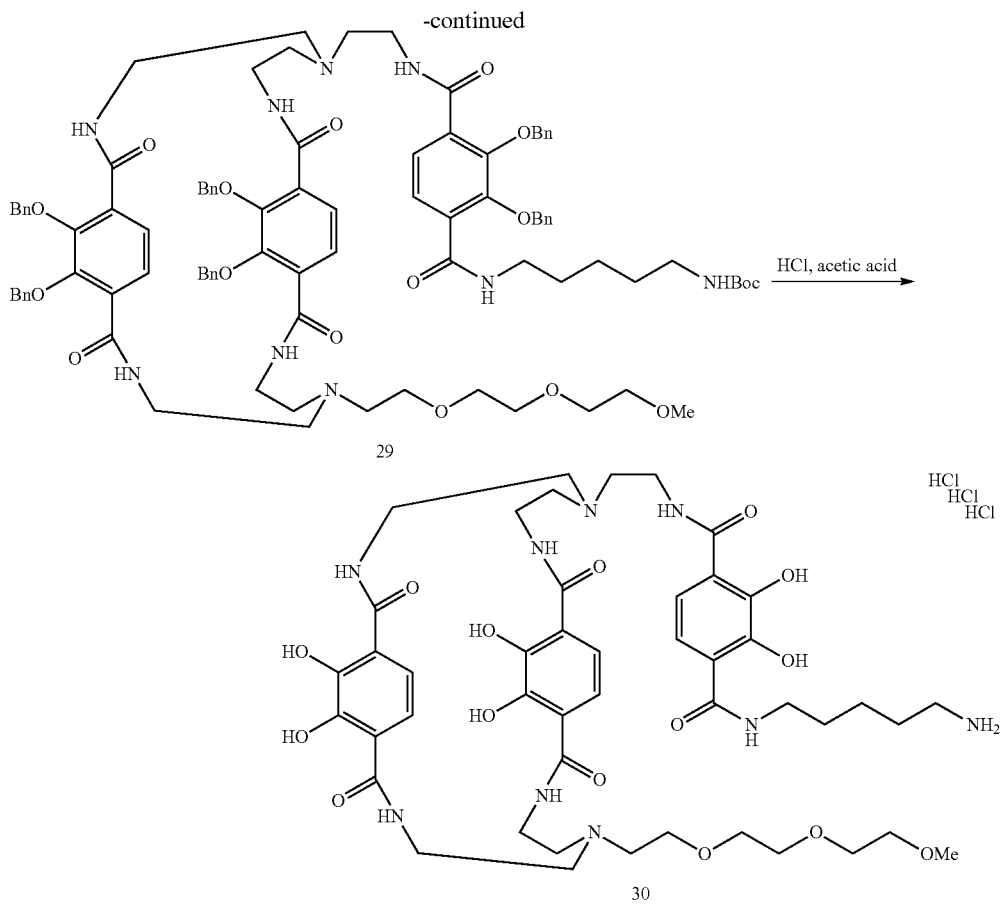

Preparation of a terephthalamide (TAM) bi-macrocyclic ligand began with 2,3-dibenzyloxy-bis(2-mercaptothiazolide)terephthalamide 14, which was condensed with tris-(2-aminoethyl)amine 4 under pseudo-first order conditions to provide the activated tri-amide 26, which was reacted with [2-[2-(2-methoxyethoxy)ethoxy]ethoxy] diethylenetriamine 27 under high dilution conditions to form the bi-macrocycle 28. The remaining activated amide in 28 was reacted with amine 11 to provide bi-macrocycle 29. Protective groups were removed using a solution of concentrated hydrochloric acid in acetic acid to provide bi-macrocycle 30.

[2-[2-(2-Methoxyethoxy)ethoxy]ethoxy] diethylenetriamine 27 was synthesized as described (PCT/US13/70356).

N,N',N''-tris{2-[2,3-benzyloxy-4-[(2-thioxo-3-thiazolidinyl)carbonyl]benzamidoethyl}amine 26. Tris-(2-aminoethyl)amine 4 (143 mg, 973 mol) was dissolved in isopropyl alcohol (40 mL) and triethylamine (678 µL, 4.86 mmol) and added using a syringe pump (NE1000) to a solution of 2,3-dibenzyloxy-bis(2-mercaptothiazolide)terephthalamide 14 (11.3 g, 19.5 mmol) in dichloromethane (anhydrous, 100 mL) and triethylamine (678 µL, 4.86 mmol) over a period of 41 hrs at a rate of 1.00 mL/hr. After a further two days, solvent was removed under reduced pressure, and the crude product was purified by silica gel chromatography using 0.1% triethylamine, 2-3.5% isopropyl alcohol in dichloromethane as eluents. Fractions containing product were combined, solvent was removed under reduced pressure, and the residue dried in vacuo to provide compound 26 (1.235 g, 82.9%). $^1$H NMR (300 MHz, CDCl$_3$): δ=7.75 (t, 3H, NH), 7.69 (d, 3H, ArH), 7.38-7.29 (m, 30H, PhH), 7.18 (d, 3H, ArH), 5.07 (s, 12H, PhCH$_2$O), 4.37 (t, 6H, NCH$_2$CH$_2$S), 3.17 (m, 6H, CH$_2$NC=O), 2.93 (t, 6H, NCH$_2$CH$_2$S), 2.34 (t, 6H, CH$_2$N). $^{13}$C NMR (600 MHz, CDCl$_3$): δ=202, 166.8, 164.4, 150.0, 149.3, 137.0, 135.8, 133.2, 130.5, 128.9, 128.8, 128.6, 128.3, 128.0, 126.4, 124.4, 76.1, 55.6, 52.9, 37.6, 28.7. FTMS pESI: calculated for C$_{81}$H$_{76}$N$_7$O$_{12}$S$_6$ [M+H]$^+$, 1530.3871, found, 1530.3927.

Benzyl-protected mono-macrocycle 28. A solution of [2-[2-(2-methoxyethoxy)ethoxy]ethoxy] diethylenetriamine 27 (73.2 mg, 294 µmol) in isopropyl alcohol (40 mL) and triethylamine (205 µL, 1.47 mmol) and a solution of N,N',N''-tris{2-[2,3-benzyloxy-4-[(2-thioxo-3-thiazolidinyl)carbonyl]benzamidoethyl}amine 26 (1.124 g, 734 µmol) in anhydrous dichloromethane (40 mL) were added dropwise to a solution of dichloromethane (1.20 L) and triethylamine (205 µL), degassed three times with N$_2$, over a period of three days using two syringe pumps at a rate of 0.5 mL/hr. After an additional two days of reaction, solvent was removed under reduced pressure, and the crude product was purified by silica gel chromatography using 0.1% triethylamine, 3.5-7.5% isopropyl alcohol in dichloromethane as eluents. Fractions containing product were combined, solvent was removed under reduced pressure, and the residue dried in vacuo to provide the protected mono-macrocycle 28 (215 mg, 47.4%). $^1$H NMR (400 MHz, CDCl$_3$): δ=7.76 (d, 1H, ArH), 7.76-7.69 (m, 3H, NH), 7.45-7.30 (broad m, 30H, PhH), 7.23 (d, 1H, ArH), 7.17 (d, 2H, ArH), 7.07 (d, 2H, ArH), 5.17 (s, 2H, PhCH$_2$O), 5.11 (s, 2H, PhCH$_2$O), 5.02 (s, 4H, PhCH$_2$O), 4.99 (s, 4H, PhCH$_2$O), 4.32 (t, 2H, NCH$_2$CH$_2$S), 3.57-3.42 (m, 20H, CH$_2$NC=O, CH$_2$CH$_2$O), 3.36 (s, 3H, OCH$_3$), 2.99 (t, 2H, NCH$_2$CH$_2$S), 2.68-2.30 (m, 12H, CH$_2$N). $^{13}$C NMR (400 MHz, CDCl$_3$): δ=201.1, 167.0, 165.9, 164.3, 150.4, 150.3, 150.1, 149.3, 137.1, 136.5, 135.8, 133.4, 132.1, 131.5, 130.2, 129.0, 128.9, 128.7, 128.6, 128.5, 128.3, 128.0, 126.6, 125.1, 125.0, 124.5, 76.1, 71.9, 70.5, 70.4, 70.2, 68.9, 59.0, 55.6, 52.6, 52.1, 51.8, 51.7, 37.2, 36.3, 28.7. FTMS pESI: calculated for C$_{86}$H$_{93}$N$_8$O$_{15}$S$_2$ [M+H]$^+$, 1541.6196, found, 1541.6259.

Benzyl and tert-butyloxycarbonyl-protected mono-macrocycle 29. A solution of benzyl-protected mono-macrocycle 28 (161 mg, 104 μmol) in dry dichloromethane (5 mL) and triethylamine (73 μL, 523 μmol) was treated with N-Boc-cadavarine 11 (21 mg, 104 μmol) under N$_2$, and allowed to stir for 22 hr. Solvent was removed under reduced pressure, and the crude product was purified by silica gel chromatography using 0.1% triethylamine, 3.5-5% methanol in dichloromethane as eluents. Fractions containing product were combined, solvent was removed under reduced pressure, and the residue dried in vacuo to provide the protected mono-macrocycle 29 (158 mg, 93.1%). $^1$H NMR (300 MHz, MeOD): δ=8.04 (m, 2H, ArH), 7.35-7.20 (broad m, 30H, PhH), 6.95 (d of d, 4H, ArH), 5.06-4.45 (m, 12H, PhCH$_2$O), 3.5-2.9 (m, 27H, CH$_2$NC=O, CH$_2$O, OMe), 2.8-2.3 (m, 12H, CH$_2$N), 1.41 (s, 9H, CH$_3$), 1.4-1.2 (m, 6H, CH$_2$). $^{13}$C NMR (300 MHz, MeOD): δ=167.1, 150.7, 150.5, 150.4, 136.6, 132.8, 132.2, 128.9, 128.6, 128.4, 124.9, 124.7, 124.3, 78.9, 76.6, 76.3, 71.7, 70.2, 70.1, 68.9, 58.1, 52.5, 52.1, 51.7, 40.1, 37.3, 29.5, 28.9, 27.8, 24.2. FTMS pESI: calculated for C$_{93}$H$_{109}$N$_9$O$_{17}$K [M+K]$^+$, 1662.7573, found, 1662.7655.

Mono-macrocycle 30. Benzyl and tert-butyloxycarbonyl-protected mono-macrocycle 29 (94 mg, 58 μmol) was dissolved in 12N hydrochloric acid (1.5 mL) and glacial acetic acid (1.5 mL). The solution was stirred under inert atmosphere for 23 hr, whereupon HCl was removed with a stream of inert gas. Solvents were removed under reduced pressure and the residue was dried in vacuo. The residue was dissolved in methanol (1500 μL) and dimethylformamide (100 μL) and transferred to four O-ring microcentrifuge tubes. Ether (ca. 1.5 mL) was added, and the tubes were placed at 4° C. for 24 hr. The tubes were centrifuged at 12,000 rpm for 3 minutes, decanted, the pellets were washed with ether (ca. 1.5 mL) and allowed to air dry. The pellets were dried in vacuo to provide mono-macrocycle 30, trihydrochloride salt (59 mg, 93%). FTMS pESI: calculated for C$_{46}$H$_{66}$N$_9$O$_{15}$ [M+H]$^+$, 984.4673, found, 984.4702.

Example 7

Synthesis of Bi-Macrocyclic Chelator Metal Cation Complexes (Scheme 7).

Scheme 7. Synthesis of bi-macrocyclic chelator metal cation complexes (formation of the thorium(IV) complexes is shown; only four bonds to the metal cation are shown for clarity).

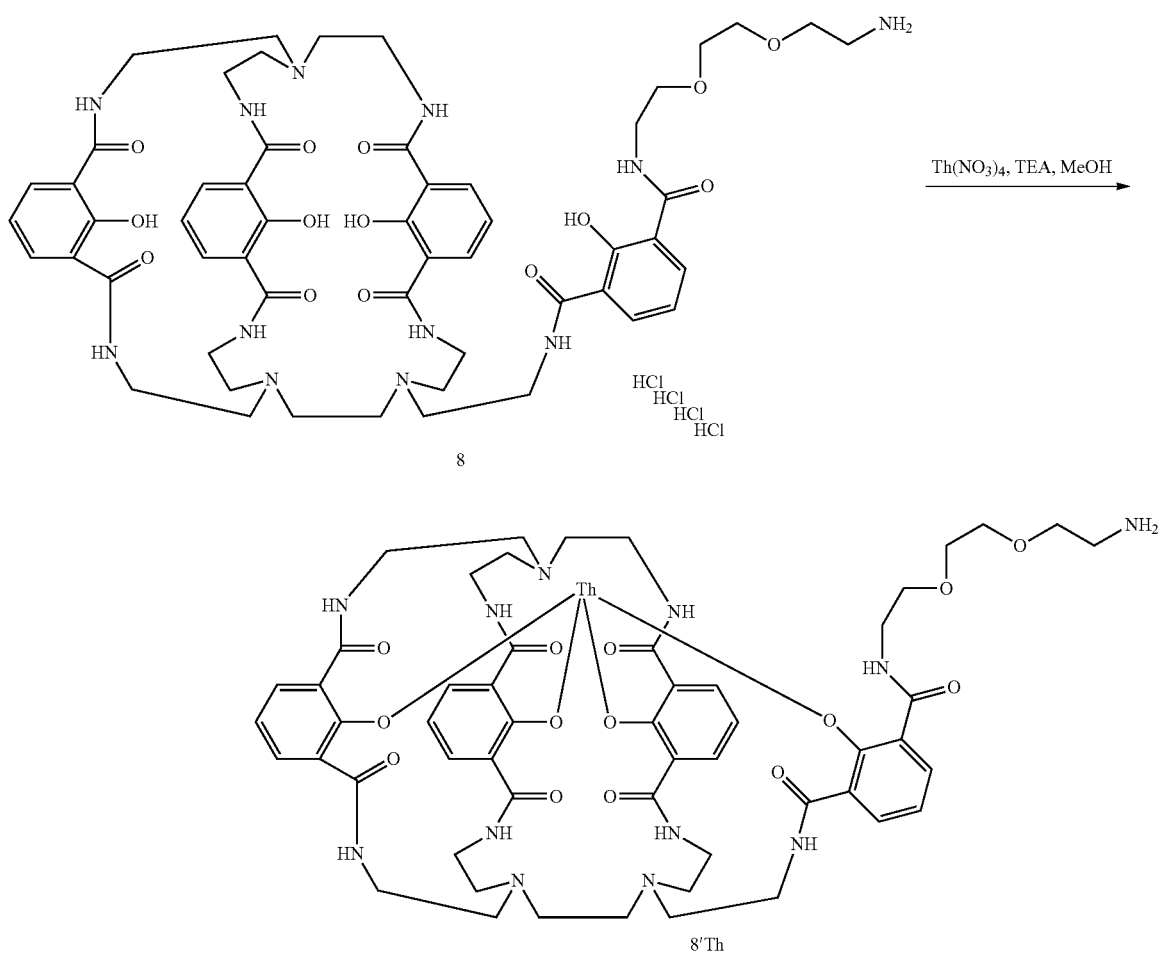

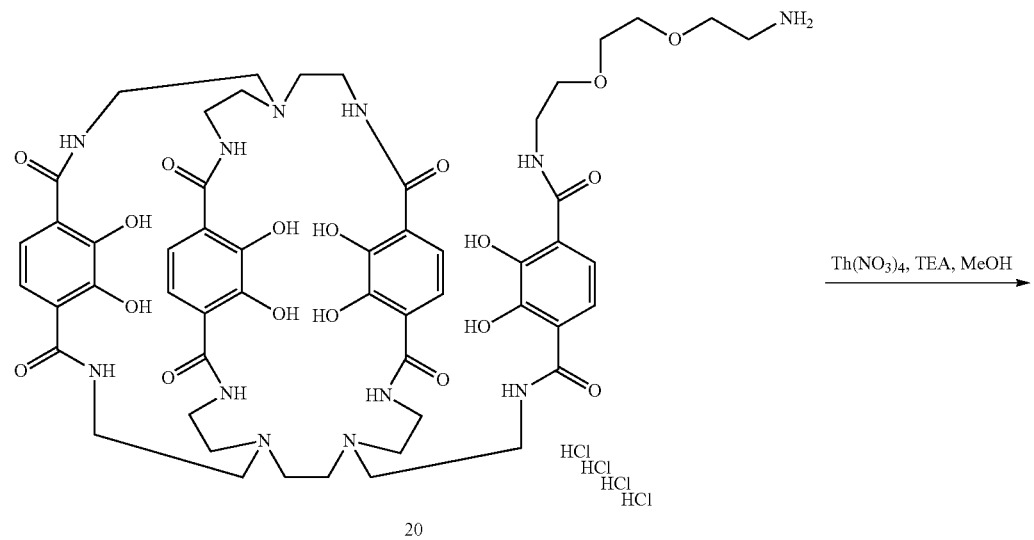
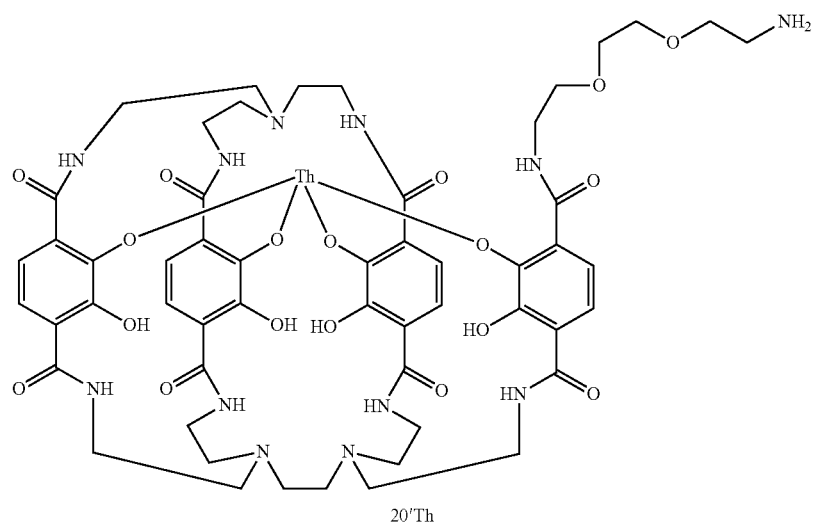
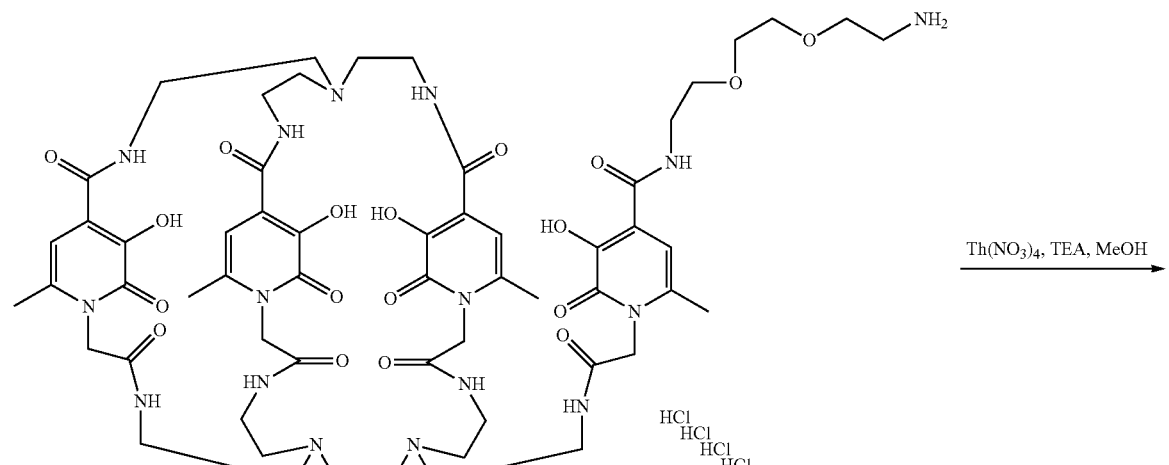

-continued

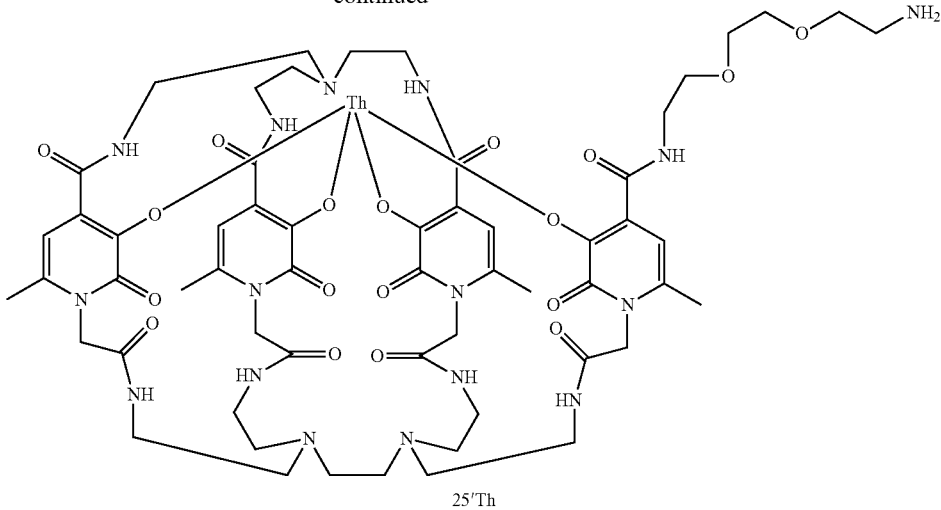

25'Th

Metal cation complexes of bi-macrocyclic chelators may be prepared readily, for example, by treatment with the metal cation as a solution in methanol in the presence of a tertiary amine as described below. Stock solutions of the tetrahydrochloride salts of chelators 8, 20, and 25 were prepared at a concentration of 20 mM in methanol (methanol and dimethylformamide for 20). Triethylamine (ca. 20 molar equivalents) was added to each stock solution to free the base. Stock solutions of metal cation salts were prepared at a concentration of 10 mM in methanol (5 mM for thorium nitrate and zirconium acetylacetonate). Chelator 8, 20, or 25 (20 μL) was added to 5 mM metal cation salt solution in 100 μL methanol (ca. 1.25 molar equivalent) at ambient temperature in a 2 mL microcentrifuge tube. A precipitate formed immediately. After gently mixing for 5 minutes, isopropyl alcohol (ca. 1.8 mL) was added, and the samples were stored at ambient temperature for 10 minutes. The samples were centrifuged for 3 minutes at 12,000 rpm, whereupon the supernatants were decanted and the pellets washed with diethyl ether (1 mL per tube). The samples were centrifuged, the supernatants were decanted, and the pellets were allowed to air dry. Chelators treated with zirconium acetylacetonate were mixed for 24 hrs prior to addition of isopropyl alcohol and washing as described above. Samples were analyzed in methanol or 10% DMSO in methanol by mass spectrometry, with results reported below. The europium(III) and terbium(III) complexes of chelator 8 were noted to be luminescent when viewed using a long wavelength (365 nm) UV lamp. Absorption and emission spectra for these species were obtained. Metal cation salts tested include europium(III) chloride hexahydrate (99.99%), terbium chloride hexahydrate (99.9%), thorium nitrate hydrate (99.8%), zirconium acetylacetonate, lutetium chloride hydrate (99.99+%), yttrium chloride hydrate (99.99%), and dysprosium chloride hydrate (99.99%). Results:

20•Dy: FTMS +pESI: calculated for $C_{54}H_{68}N_{12}O_{18}Dy$ $[M]^+$, 1336.4061, found, 1336.4092.
8•Dy: FTMS +pESI: calculated for $C_{54}H_{68}N_{12}O_{14}Dy$ $[M]^+$, 1272.4264, found, 1272.4274.
25•Dy: FTMS +pESI: calculated for $C_{58}H_{80}N_{16}O_{18}Dy$ $[M]^+$, 1452.5123, found, 1452.5128.
20•Eu: FTMS −pESI: calculated for $C_{54}H_{65}N_{12}O_{18}Eu$ $[M]^2$, 660.1875, found, 660.1877.
8•Eu: FTMS pESI: calculated for $C_{54}H_{68}N_{12}O_{14}Eu$ $[M]^+$, 1259.4171, found, 1259.4149.
25•Eu: FTMS pESI: calculated for $C_{58}H_{80}N_{16}O_{18}Eu$ $[M]^+$, 1439.5030, found, 1439.5040.
20•Lu: FTMS −pESI: calculated for $C_{54}H_{65}N_{12}O_{18}Lu$ $[M]^2$, 672.1979, found, 672.1973.
8•Lu: FTMS +pESI: calculated for $C_{54}H_{68}N_{12}O_{14}Lu$ $[M]^+$, 1283.4380, found, 1283.4376.
25•Lu: FTMS +pESI: calculated for $C_{58}H_{80}N_{16}O_{18}Lu$ $[M]^+$, 1463.5239, found, 1463.5237.
20•Tb: FTMS +pESI: calculated for $C_{54}H_{68}N_{12}O_{18}Tb$ $[M]^+$, 1331.4023, found, 1331.4041.
8•Tb: FTMS +pESI: calculated for $C_{54}H_{68}N_{12}O_{14}Tb$ $[M]^+$, 1267.4226, found, 1267.4202.
25•Tb: FTMS +pESI: calculated for $C_{58}H_{80}N_{16}O_{18}Tb$ $[M]^+$, 1447.5085, found, 1447.5092.
20•Th: FTMS +pESI: calculated for $C_{54}H_{67}N_{12}O_{18}Th$ $[M]^+$, 1403.5071, found, 1403.5126.
8•Th: FTMS +pESI: calculated for $C_{54}H_{67}N_{12}O_{14}Th$ $[M]^+$, 1339.5275, found, 1339.5317.
25•Th: FTMS +pESI: calculated for $C_{58}H_{79}N_{16}O_{18}Th$ $[M]^+$, 1519.6133, found, 1519.6139.
20•Y: FTMS +pESI: calculated for $C_{54}H_{68}N_{12}O_{18}Y$ $[M]^+$, 1261.3828, found, 1261.3854.
8•Y: FTMS +pESI: calculated for $C_{54}H_{68}N_{12}O_{14}Y$ $[M]^+$, 1197.4031, found, 1197.4025.
25•Y: FTMS +pESI: calculated for $C_{58}H_{80}N_{16}O_{18}Y$ $[M]^+$, 1377.4890, found, 1377.4882.
20•Zr: FTMS −pESI: calculated for $C_{54}H_{64}N_{12}O_{18}Zr$ $[M]^{2-}$, 629.1760, found, 629.1756.
8•Zr: FTMS +pESI: calculated for $C_{54}H_{67}N_{12}O_{14}Zr$ $[M]^+$, 1197.3941, found, 1197.3953.
25•Zr: FTMS +pESI: calculated for $C_{58}H_{79}N_{16}O_{18}Zr$ $[M]^+$, 1377.4800, found, 1377.4805.

Figure 1B:
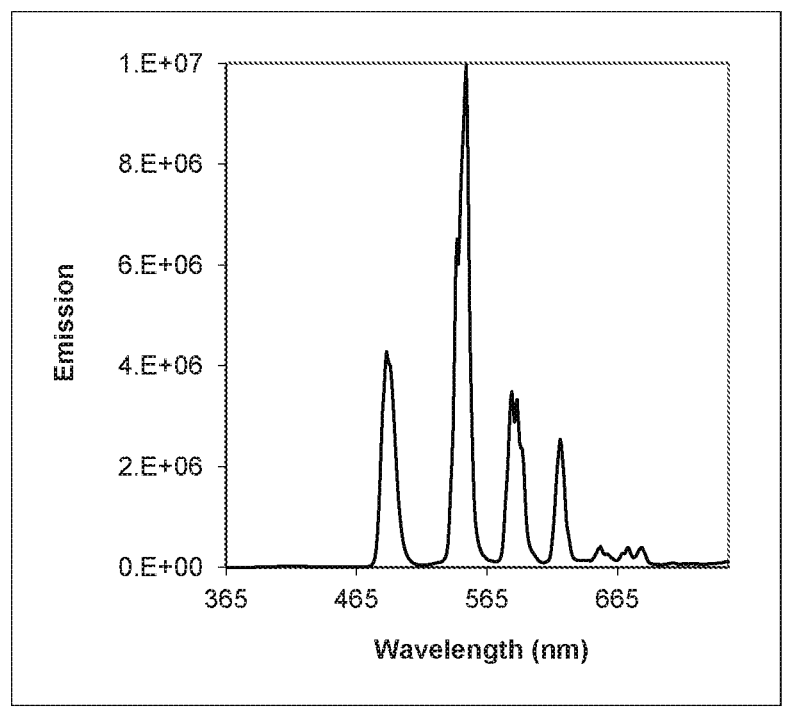
FIG. 1B shows an emission spectrum of bi-macrocyclic chelator 8 with terbium(III).

FIG. 1 shows emission spectra of bi-macrocyclic chelator 8 with europium(III) (FIG. 1A) and with terbium(III) (FIG. 1B).

Example 8

Synthesis of a Bi-Macrocyclic Isothiocyanate Derivative (Scheme 8).

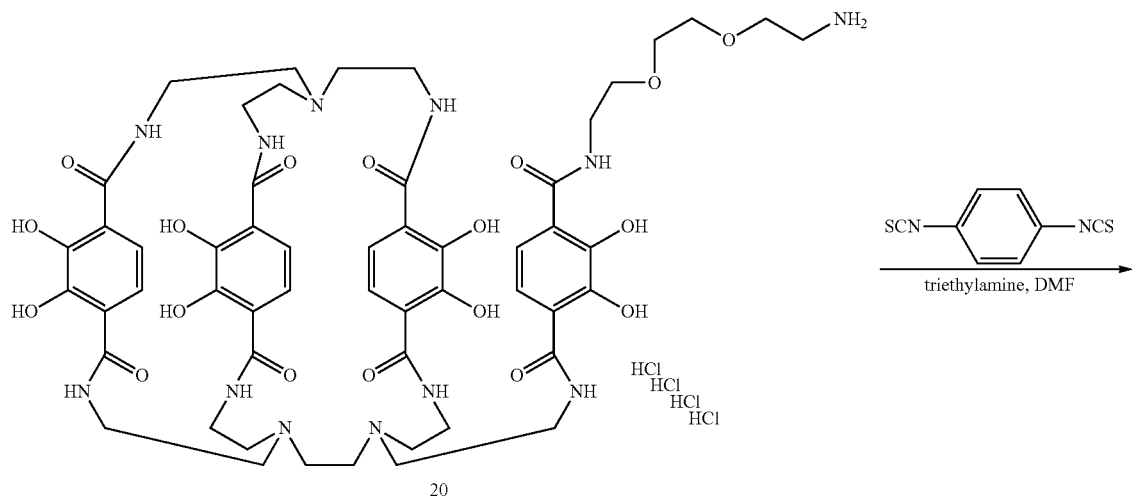

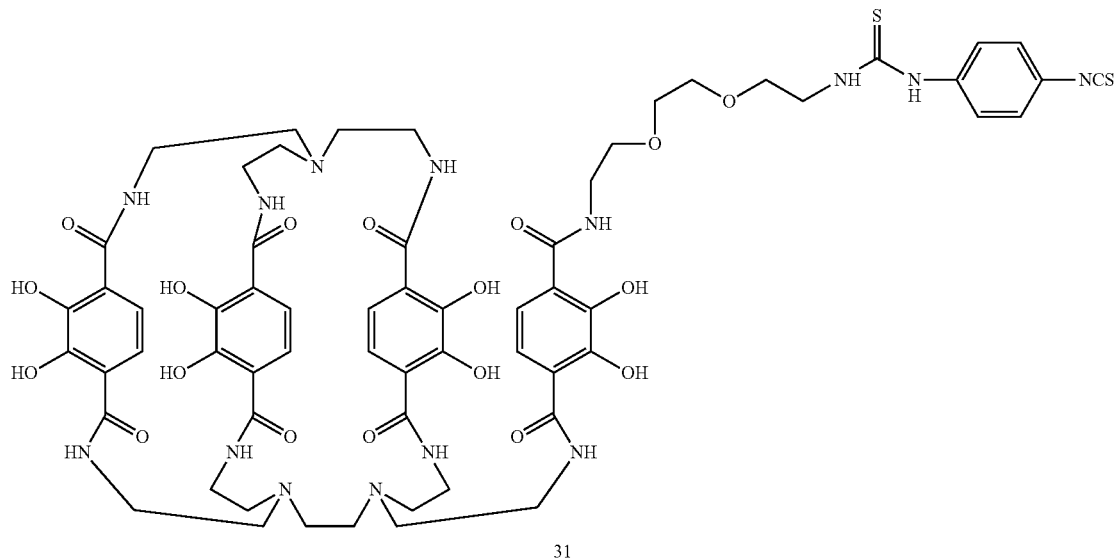

Bi-macrocycle, 4-isothiocyanatophenylthiourea derivative 31. To bi-macrocycle 20 (10.4 mg, 7.86 µmol), dissolved in dimethylformamide (200 µL) and triethylamine (21.9 µL) in an O-ring type microcentrifuge tube, was added a solution of 1,4-phenyldiisothiocyanate (18.8 mg, 98 µmol) in dimethylformamide (200 µL). The resulting solution was mixed at 1200 rpm under inert atmosphere for 1 hour. Half the solution was added to a second microtube and ether (ca. 1.5 mL per tube) was added to both tubes. The resulting suspensions were stored at 4° C. overnight. The tubes were centrifuged at 12,000 rpm for 3 minutes, decanted, the pellets were washed with ether (ca. 1.5 mL) and allowed to air dry. The pellets were dissolved in dimethylformamide (40 µL/tube) and then methanol (300 µL per tube), then precipitated and washed with ether as described above. The pellets were dried in vacuo to provide bi-macrocycle, 4-isothiocyanatophenylthiourea derivative 31 (10.51 mg, 97.8%). FTMS pESI: calculated for $C_{62}H_{75}N_{14}O_{18}S_2$ $[M+H]^+$, 1367.4820, found, 1367.4807.

Example 9
Synthesis of an Octa-Coordinating Bi-Macrocyclic Bifunctional Chelator (Scheme 9).
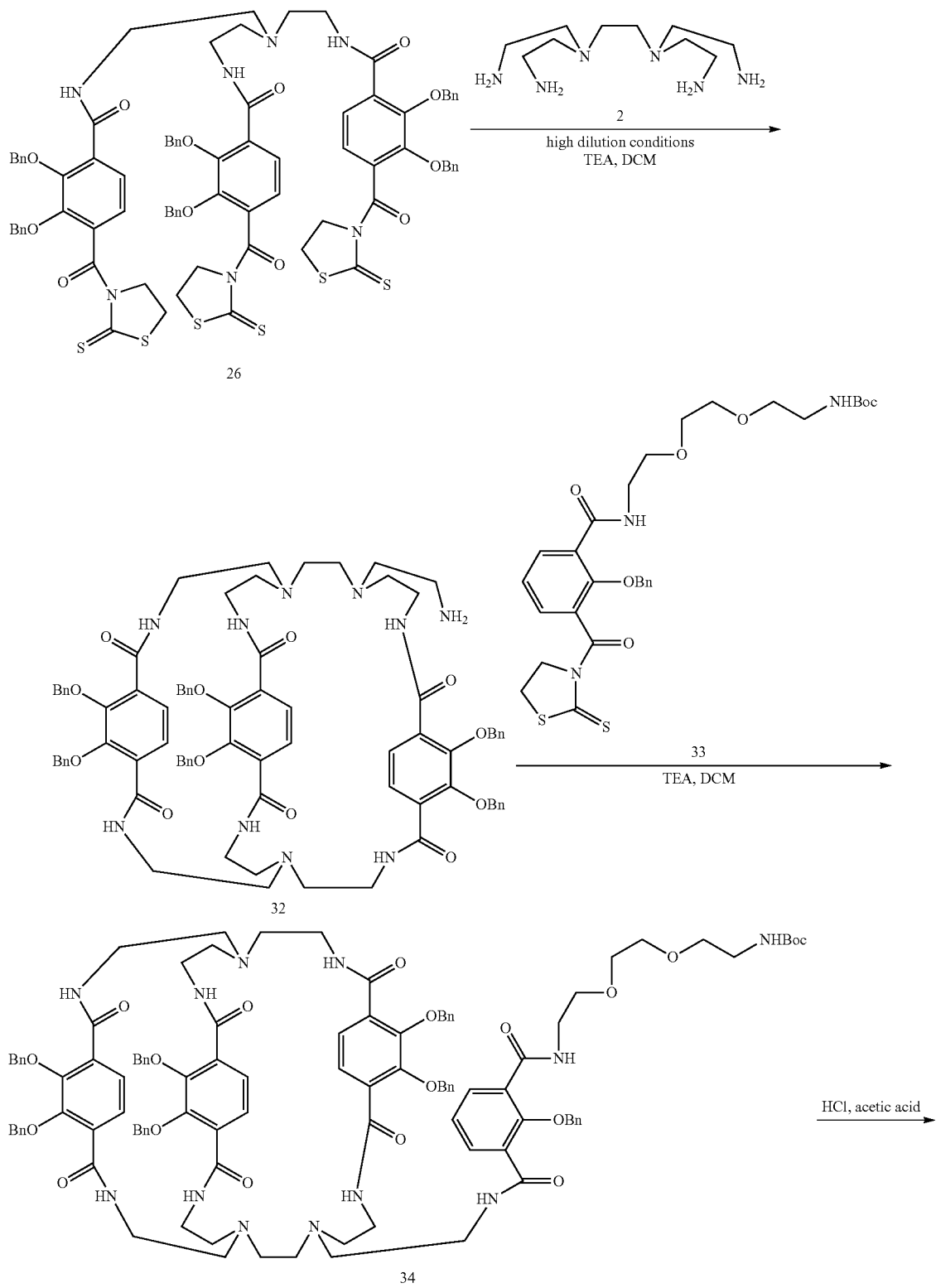

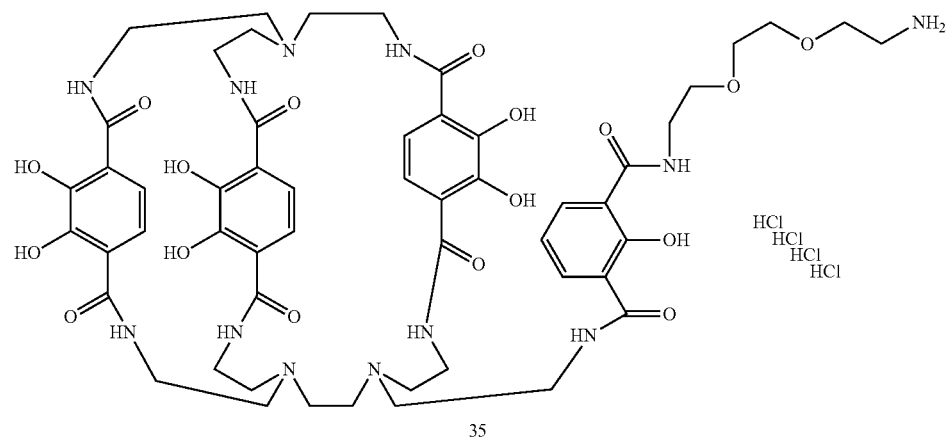 [SMILES: NCCOCCOCCNC(=O)c1cccc(C(=O)NCCN2CCNC(=O)c3ccc(c(O)c3O)C(=O)NCCN3CCNC(=O)c4ccc(c(O)c4O)C(=O)NCCN(CCNC(=O)c4ccc(c(O)c4O)C(=O)NCC3)CC2)c1O ; Cl ; Cl ; Cl ; Cl]

35

Preparation of a terephthalamide (TAM)/isophthalamide (IAM) bi-macrocyclic ligand begins with N,N',N''-tris{2-[2,3-benzyloxy-4-[(2-thioxo-3-thiazolidinyl)carbonyl]benzamidoethyl}amine 26, which is condensed with tetrakis-(2-aminoethyl) ethylene diamine 2 under high dilution conditions to form the bi-macrocycle 32. The remaining amine in 28 is reacted with activated amide 33 (prepared from 2-benzyloxy-1,3-phenylenebis((2-thioxothiazolidin-3-yl)methanone) 1 and N-Boc-2,2'-(ethylenedioxy)diethylamine 6), to provide bi-macrocycle 34. Protective groups are removed using a solution of concentrated hydrochloric acid in acetic acid to provide bi-macrocycle 35.

Example 10

Synthesis of an Octa-Coordinating Bi-Macrocyclic Bifunctional Chelator (Scheme 10).

Scheme 10. Synthesis of bi-macrocyclic bifunctional chelator 40.

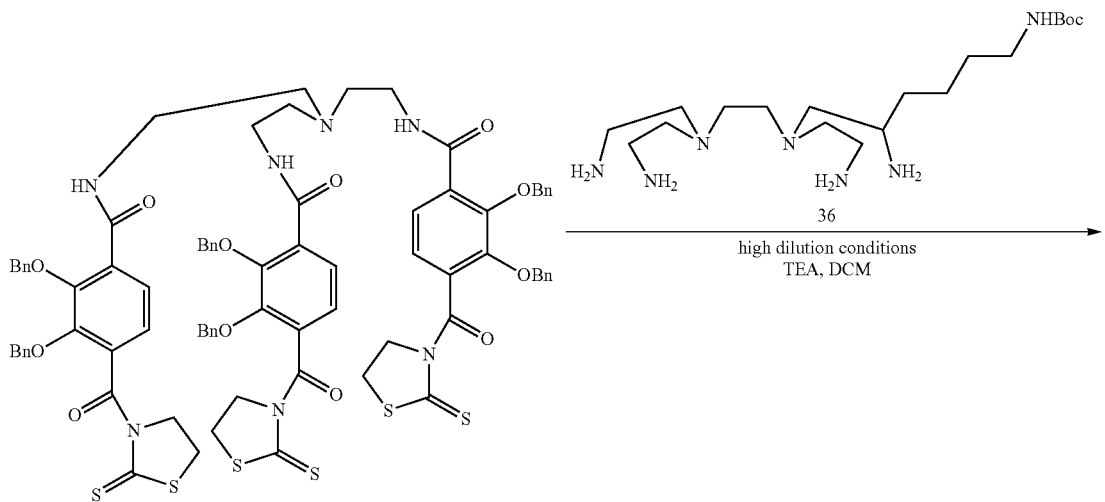

-continued
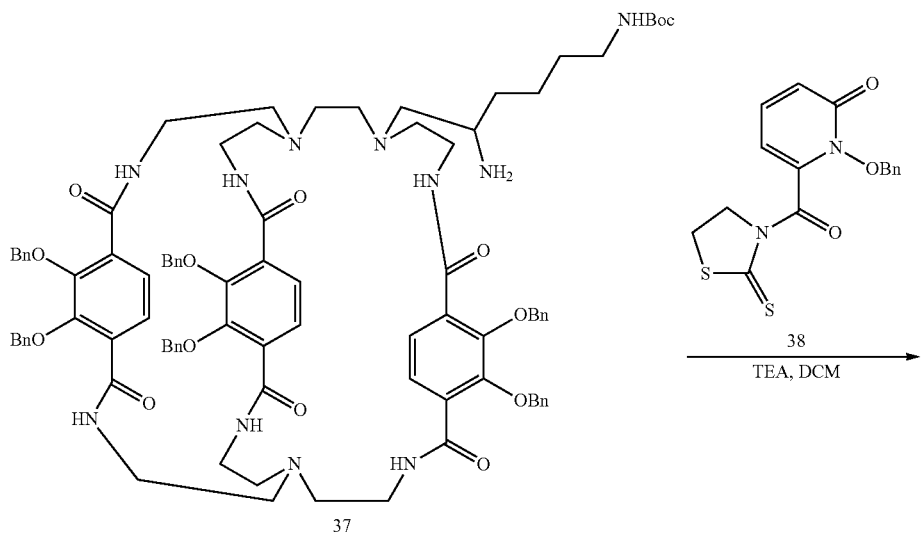
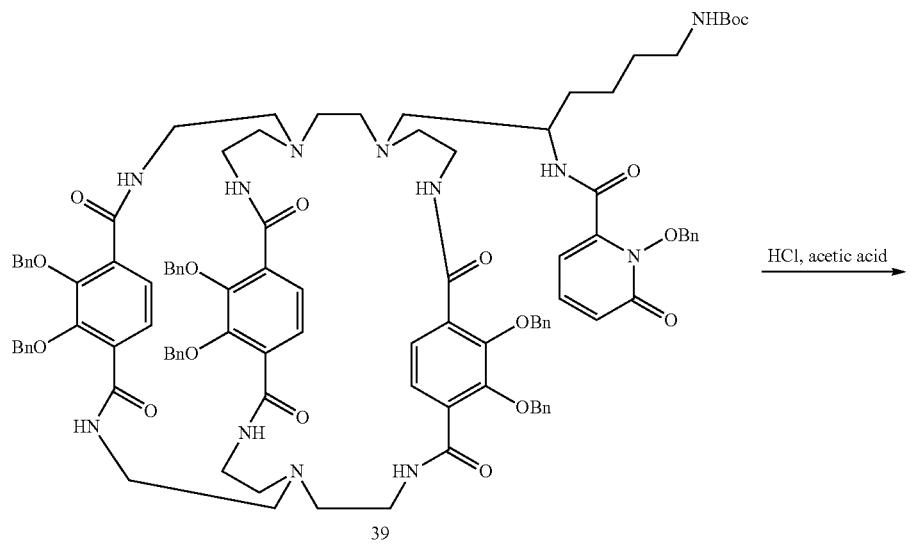
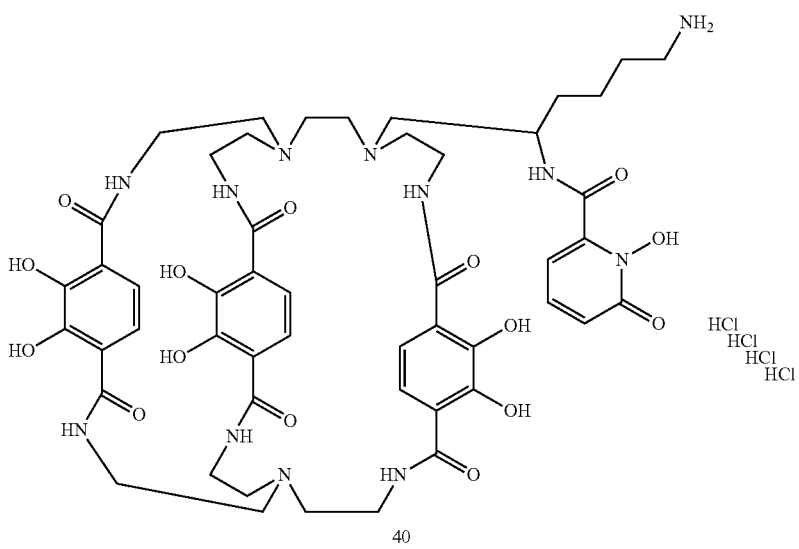 [SMILES: NCCCCC(CN1CCNC(=O)c2ccc(c(O)c2O)C(=O)NCCN2CCNC(=O)c3ccc(c(O)c3O)C(=O)NCCN(CCNC(=O)c3ccc(c(O)c3O)C(=O)NCC2)CC1)NC(=O)c1cccc(=O)n1O ; Cl ; Cl ; Cl ; Cl]

Preparation of a terephthalamide (TAM)/1-hydroxy-2-pyridinone (1,2-HOPO) bi-macrocyclic ligand begins with N,N',N''-tris {2-[2,3-benzyloxy-4-[(2-thioxo-3-thiazolidinyl)carbonyl]benzamidoethyl} amine 26, which is condensed with (S)-tert-butyl-5-amino-6-((2-aminoethyl)(2-(bis(2-aminoethyl)amino)ethyl)amino)hexylcarbamate 36 (Moore E G, Xu J, Jocher C J, Corneillie T M, Raymond K N. Inorg. Chem. 2010; 49(21):9928-9939) under high dilution conditions to form the bi-macrocycle 37. The remaining amine in 37 is reacted with activated amide 38 (Xu J, et al., Inorg. Chem., 2004, 43, 5492-5494) to provide bi-macrocycle 39. Protective groups are removed using a solution of concentrated hydrochloric acid in acetic acid to provide bi-macrocycle 40.

Example 11

Synthesis of an Octa-Coordinating Bi-Macrocyclic Bifunctional Chelator (Scheme 11).

Scheme 11. Synthesis of bi-macrocyclic bifunctional chelator 48.

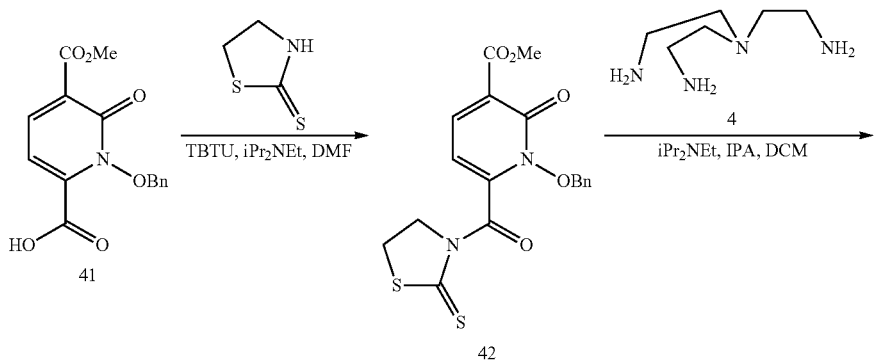

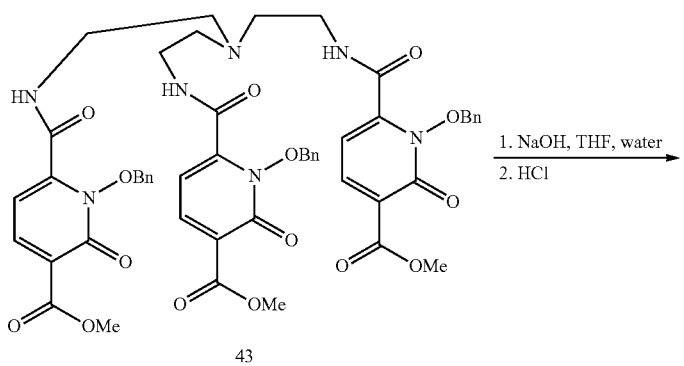

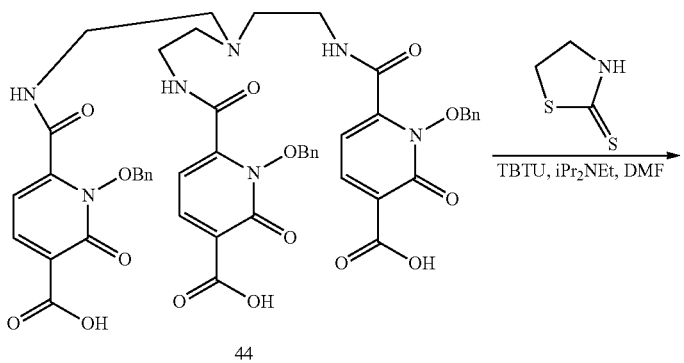

-continued
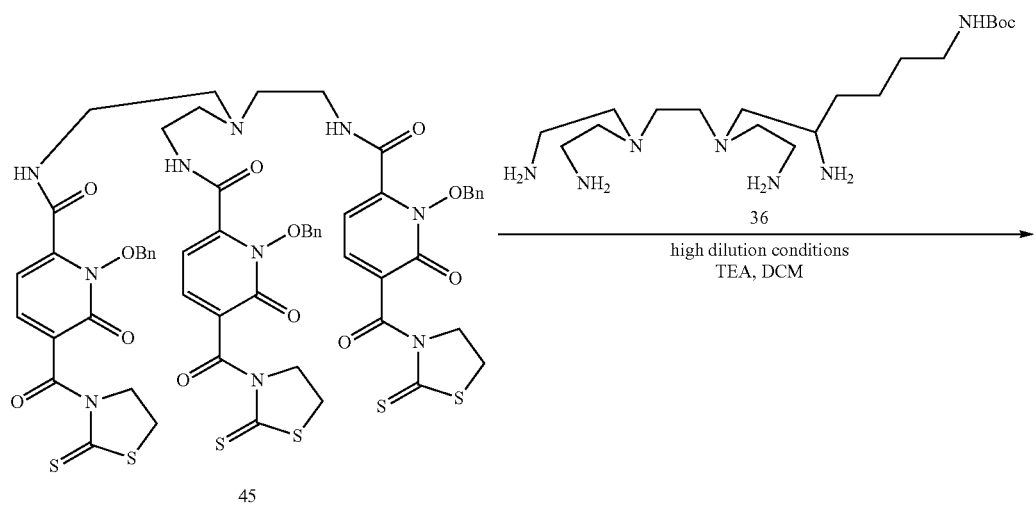
45
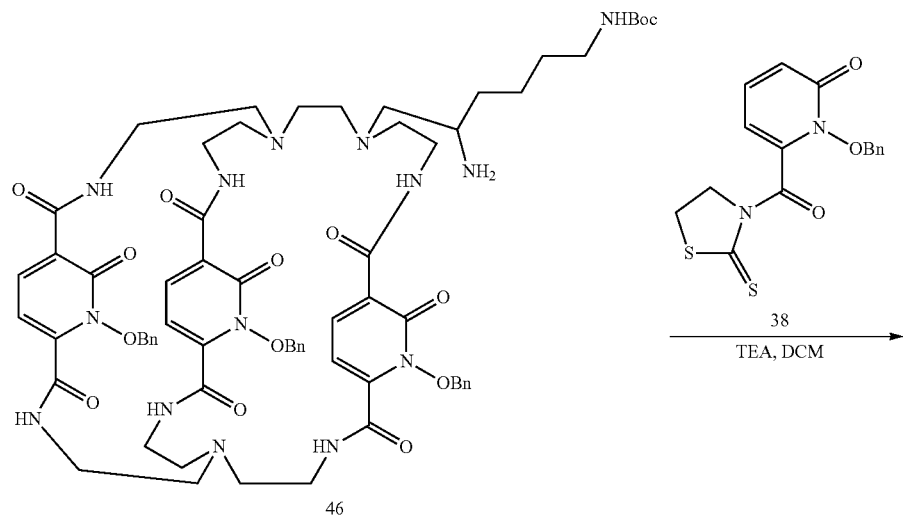
46
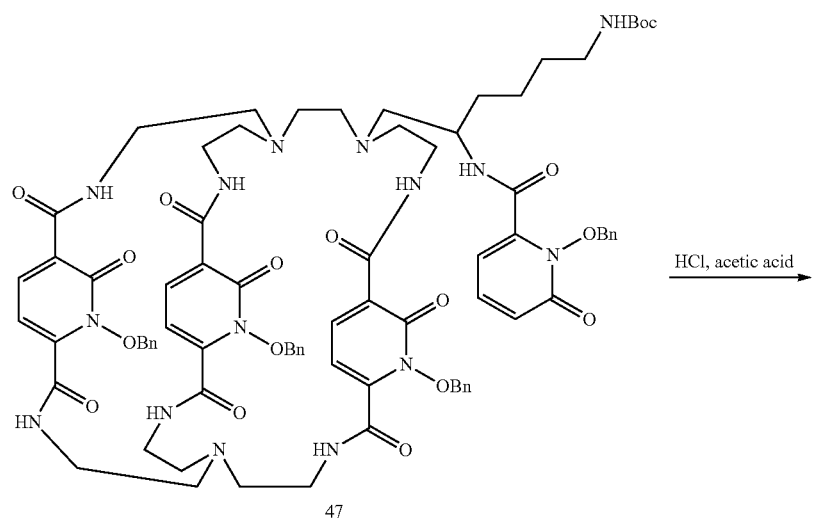
47

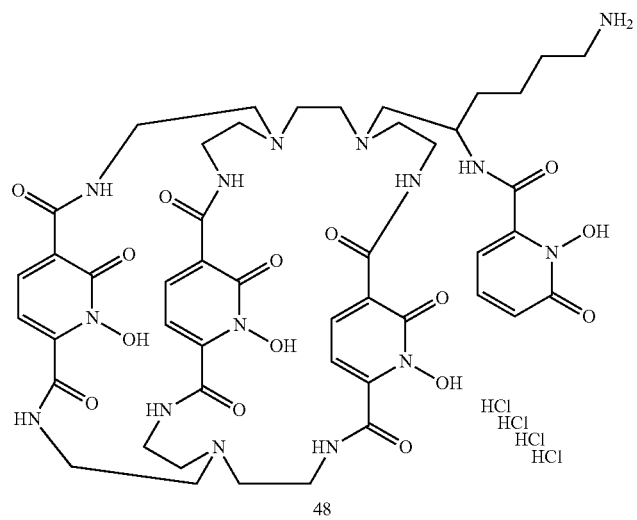

48

Preparation of a 1-hydroxy-2-pyridinone (1,2-HOPO) bi-macrocyclic ligand begins with 1-(benzyloxy)-6-(methoxy-carbonyl)-2-oxo-1,2-dihydropyridine-3-carboxylic acid 41 (PCT/US2013/070356), which is reacted with O-(benzotri-azol-1-yl)-N,N,N',N'-tetramethyluronium tetrafluoroborate (TBTU) in the presence of 2-mercaptothiazole to provide thiazolide 42. This product is condensed with tris-(2-amino-ethyl)amine 4 to form triester 43, which is saponified using sodium hydroxide and treated with hydrochloric acid to form triacid 44. Triacid 44 is reacted with TBTU in the presence of 2-mercaptothiazole to provide N,N',N''-tris {6-[1-benzyloxy-2-oxo-3-[(2-thioxo-3-thiazolidinyl)carbonyl] pyridineamidoethyl}amine 45. Tris-thiazolide 45 is con-densed with (S)-tert-butyl-5-amino-6-((2-aminoethyl)(2-(bis(2-aminoethyl)amino)ethyl)amino)hexylcarbamate 36 under high dilution conditions to form the bi-macrocycle 46. The remaining amine in 46 is reacted with activated amide 38 to provide bi-macrocycle 47. Protective groups are removed using a solution of concentrated hydrochloric acid in acetic acid to provide bi-macrocycle 48.

Example 12

Synthesis of Mono-Macrocyclic Chelator Metal Cation Complexes (Scheme 12).

Scheme 12. Synthesis of mono-macrocyclic chelator metal cation complexes (formation of the thorium(IV) complex is shown; only five bonds to the metal cation are shown for clarity).

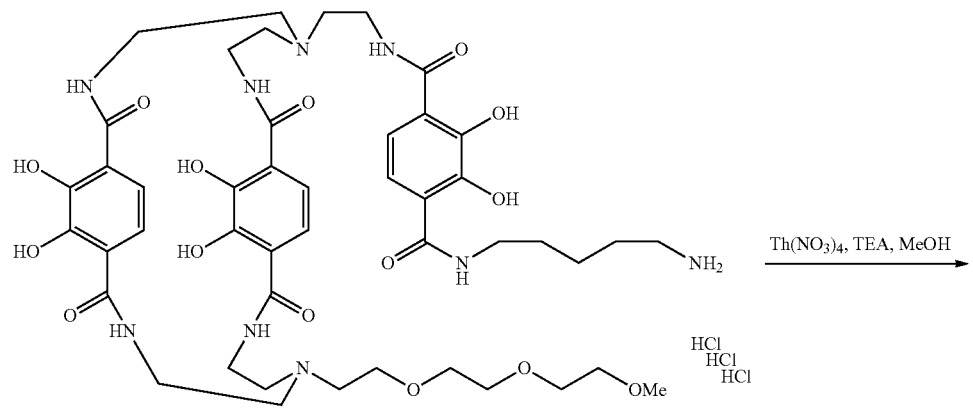

30

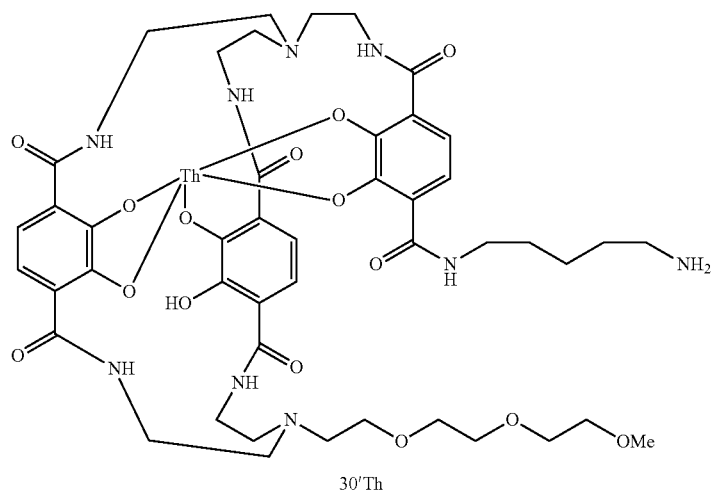

30'Th

Metal cation complexes of mono-macrocyclic chelators may be prepared readily, for example, by treatment with the metal cation as a solution in methanol in the presence of a tertiary amine as described above. Samples were analyzed in methanol or 10% DMSO in methanol by mass spectrometry, with results reported below. Results:

30•Dy: FTMS –pESI: calculated for $C_{46}H_{61}N_9O_{15}Dy$ [M], 1143.3584, found, 1143.3593.
30•Eu: FTMS +pESI: calculated for $C_{46}H_{62}N_9O_{15}EuNa$ [M+Na]$^+$, 1154.3456, found, 1154.3467.
30•Lu: FTMS –pESI: calculated for $C_{46}H_{61}N_9O_{15}Lu$ [M], 1154.3700, found, 1154.3689.
30•Tb: FTMS –pESI: calculated for $C_{46}H_{61}N_9O_{15}Tb$ [M], 1138.3546, found, 1138.3534.
30•Th: FTMS –pESI: calculated for $C_{46}H_{60}N_9O_{15}Th$ [M], 1210.4595, found, 1210.4587.
30•Y: FTMS –pESI: calculated for $C_{46}H_{61}N_9O_{15}Y$ [M], 1068.3351, found, 1068.3330.
30•Zr: FTMS +pESI: calculated for $C_{46}H_{62}N_9O_{15}Zr$ [M]$^+$, 1070.3407, found, 1070.3409.

Example 13

Synthesis of a Bi-Macrocyclic Isothiocyanate Derivative (Scheme 13).

Scheme 13. Synthesis of a bi-macrocyclic isothiocyanate derivative.

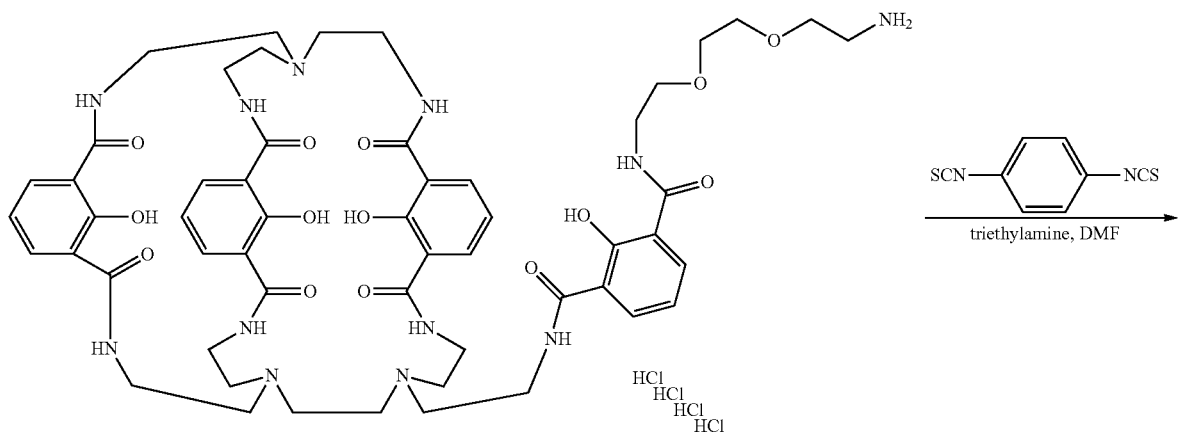

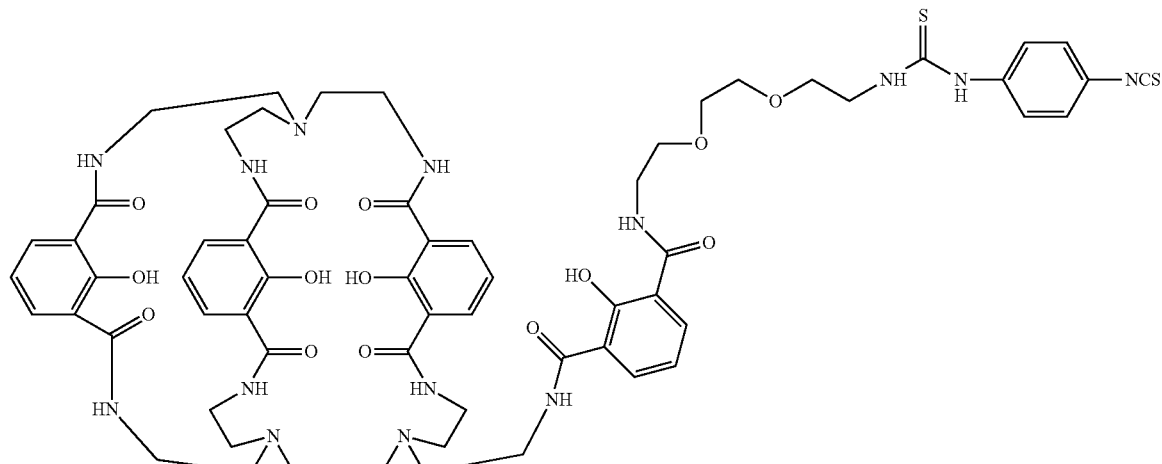

49

Bi-macrocycle, 4-isothiocyanatophenylthiourea derivative 49. To bi-macrocycle 8 (14.5 mg, 11.6 mol), dissolved in dimethylformamide (250 μL) and triethylamine (32 μL) in an O-ring type microcentrifuge tube, was added a solution of 1,4-phenyldiisothiocyanate (24.4 mg, 127 μmol) in dimethylformamide (250 μL). The resulting solution was mixed at 1200 rpm under inert atmosphere for 80 minutes. One third of the solution was added to each of two additional microtubes and ether (ca. 1.5 mL per tube) was added to all three tubes. The resulting suspensions were stored at 4° C. overnight. The tubes were centrifuged at 12,000 rpm for 3 minutes, decanted, the pellets were washed with ether (ca. 1.5 mL) and allowed to air dry. The pellets were dissolved in dimethylformamide (40 μL/tube) and then methanol (300 μL per tube), then precipitated and washed with ether as described above. The pellets were dried in vacuo to provide bi-macrocycle, 4-isothiocyanatophenylthiourea derivative 49 (11.31 mg, 75.1%). FTMS pESI: calculated for $C_{62}H_{73}N_{14}O_{14}S_2$ [M−H], 1301.4878, found, 1301.4873.

Example 14

Synthesis of a Bi-Macrocyclic Luminescent Sensor (Scheme 14).

Scheme 14. Synthesis of a bi-macrocyclic luminescent sensor. The remainder group "R" may be a peptide ligand.

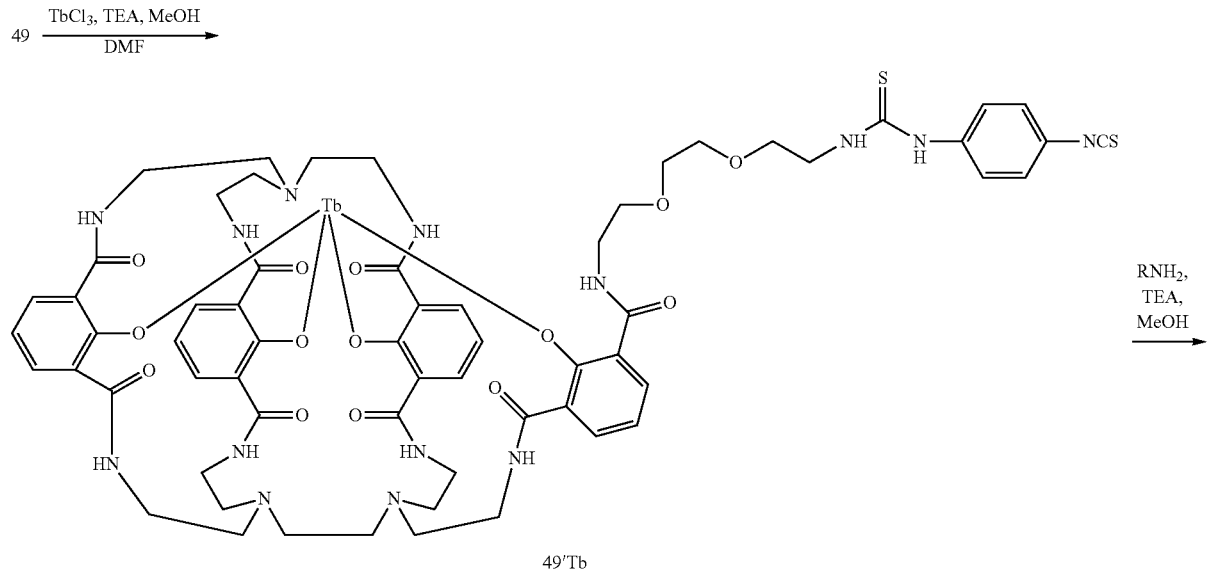

49'Tb

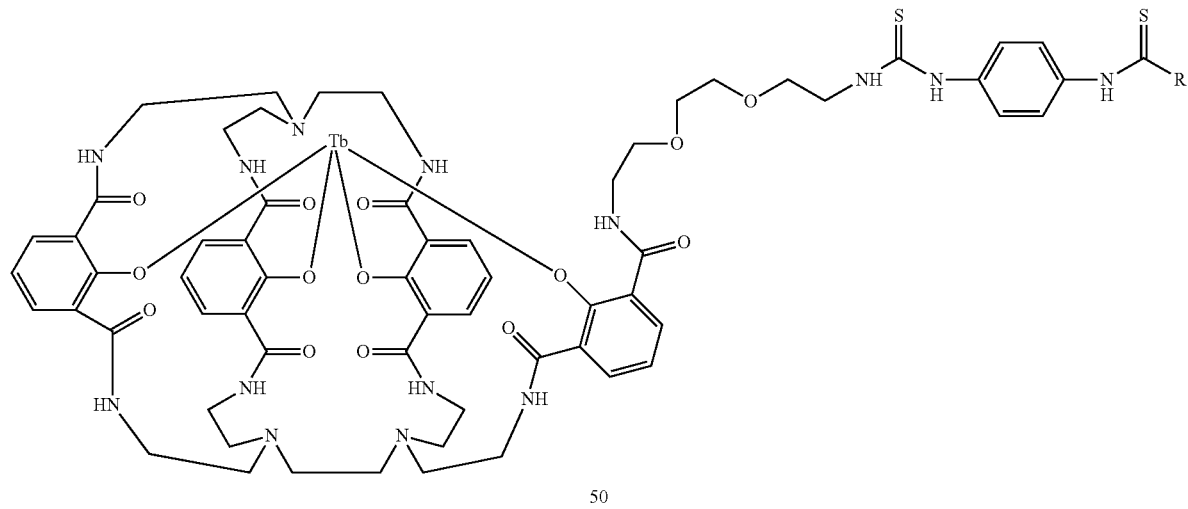

50

Preparation of a bi-macrocyclic luminescent sensor begins with bi-macrocycle, 4-isothiocyanatophenylthiourea derivative 49, which is treated with triethylamine and terbium chloride in dimethylformamide and methanol to form the terbium complex 49•Tb. This compound is reacted with an amine-containing compound to form the terbium chelator conjugate 50. The remainder group "R" may be a peptide ligand, for example, that binds to a receptor with relatively high affinity. Upon binding to the receptor, for example, the coordination sphere surrounding the terbium cation becomes unsaturated by the ligand, as the fourth isophthalamide group is no longer able to coordinate to the metal cation. As a result, the terbium atom is exposed to water, resulting in a loss of terbium luminescence. It will be apparent to one skilled in the art that conjugates such as 50 may be designed to bind to a variety of targets, such that the presence or absence of that target may be quantified in a useful way, such as, for example, for diagnosing the presence of a disease condition.

Example 15

Synthesis of Bi-Macrocyclic Protein Conjugates (Scheme 15).

Scheme 15. Synthesis of a bi-macrocylic chelator-protein conjugate. The remainder group "R" may be a protein such as streptavidin or an IgG.

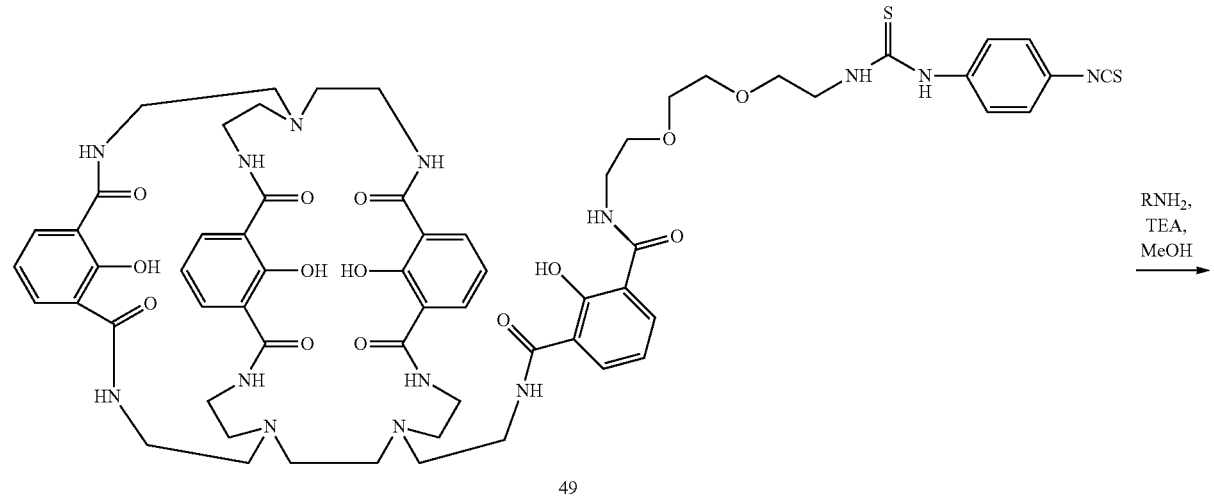

49

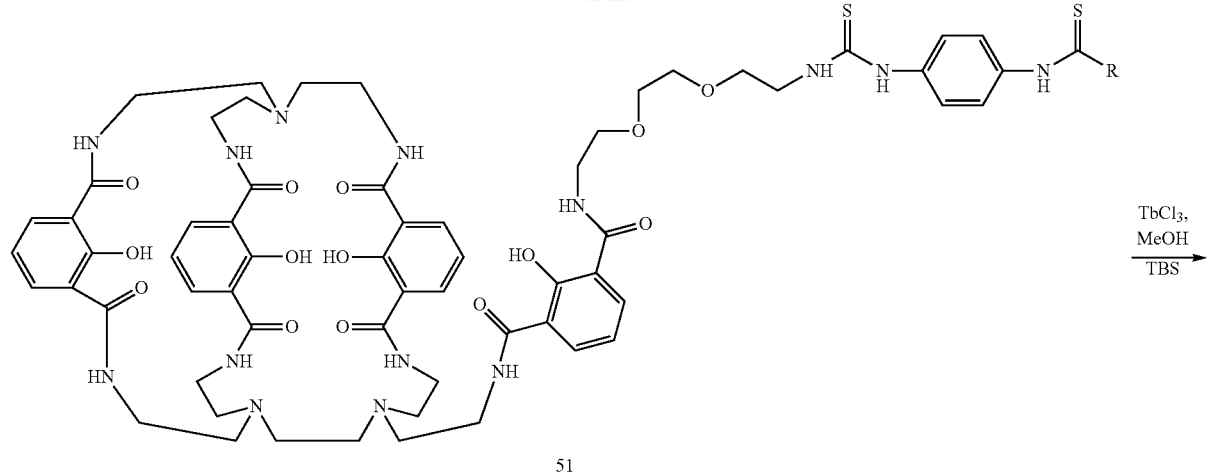

51

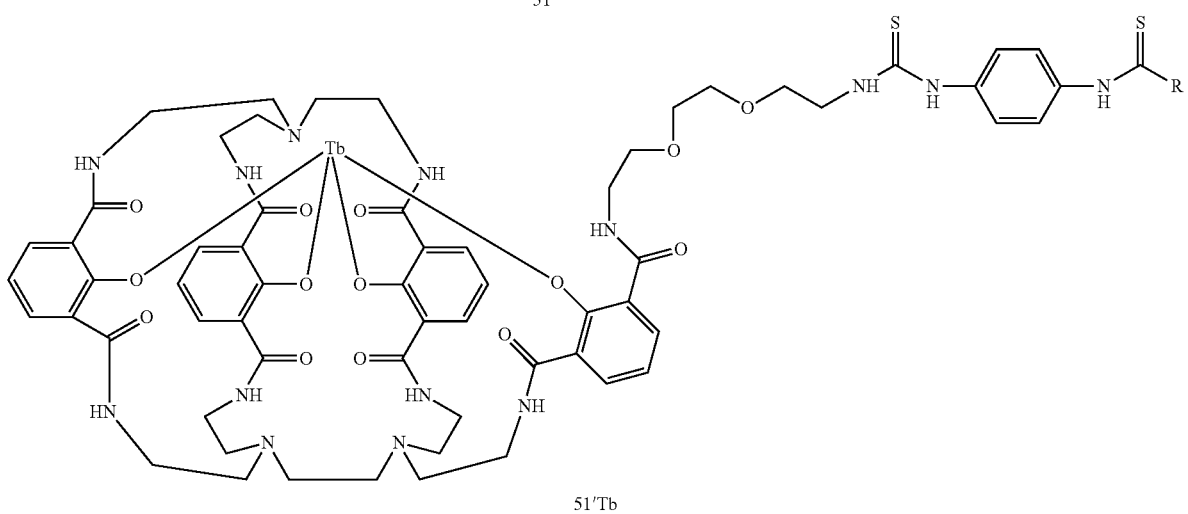

51·Tb

To a solution of streptavidin (Prozyme SA-10, 31.5 M, 1 mL per tube) in 100 mM sodium bicarbonate buffer, pH 9, in each of two O-ring type microcentrifuge tubes was added a solution of bi-macrocycle, 4-isothiocyanatophenylthiourea derivative 49 (1.5 mg, 1.2 μmol dissolved in 230 μL dimethylformamide for 5 mM final, 37.8 μL per tube for 6 molar equivalents). The resulting solutions were mixed at 800 rpm for five hours. The contents of each microtube were applied to a 10 mL Penefsky size exclusion column containing Sephadex G50 Fine equilibrated in 50 mM Tris, pH 7.6, 150 mM NaCl. The tubes were centrifuged at ca. 700 rpm for 3 minutes and the eluents collected. Additional buffer (0.5 mL per tube) was applied to each column and the combined eluents containing 51 (R=streptavidin) were mixed. The concentration of protein was measured by UV-vis spectrometry using extinction coefficients for streptavidin at 280 nm of 3.2 mL/mg, and 3,300 and 24,800 $M^{-1}$ $cm^{-1}$ for the chelator at 280 nm and 348 nm, respectively. The resulting solution was found to be 1.29 mg/mL in ca. 3 mL buffer. The degree of labeling was calculated to be 1.75 chelators per protein, using a molecular weight of 55,000 g/mol for streptavidin. A solution of IgG antibody (13.3 M, 2 mL, Thermo-Fisher 31154) was conjugated with bi-macrocycle, 4-isothiocyanatophenylthiourea derivative 49 using the same procedure, to yield a solution of 1.35 mg/mL of antibody conjugate 51 (R=IgG) in ca. 3 mL of buffer, assuming an extinction coefficient of 1.4 mL/mg at 280 nm. The degree of labeling was calculated to be 1.61 using a molecular weight of 150,000 g/mol for the IgG antibody. Diluted solutions of each conjugate were observed to fluoresce green when viewed using a long wave UV lamp, upon addition of a methanolic solution of terbium chloride, demonstrating formation of the terbium(III) conjugates 51·Tb.

Example 16

Synthesis of an Octa-Coordinating Bi-Macrocyclic Bifunctional Chelator (Schemes 16 and 17).

Scheme 16. Synthesis of tris(2-aminoethyl)amine derivative 61.

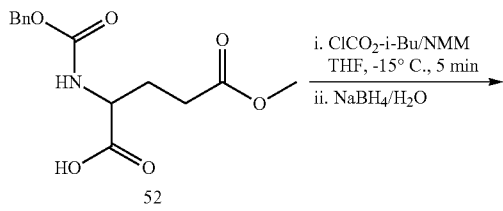

52

101

-continued

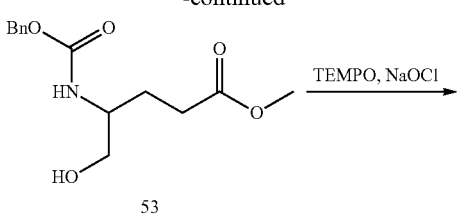

53

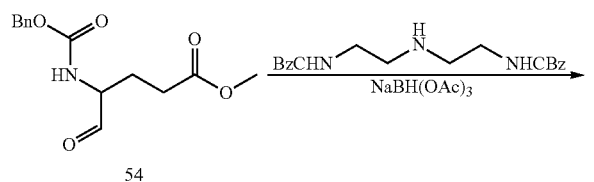

54

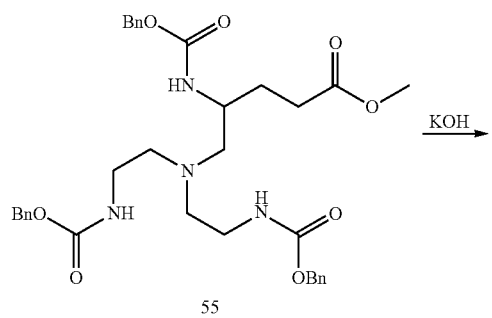

55

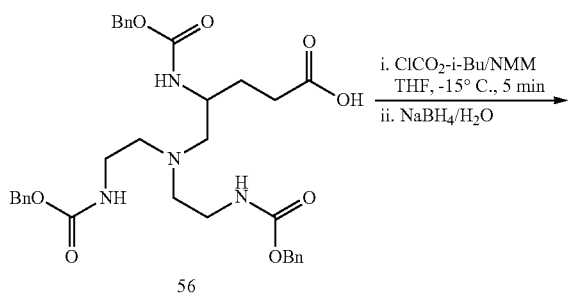

56

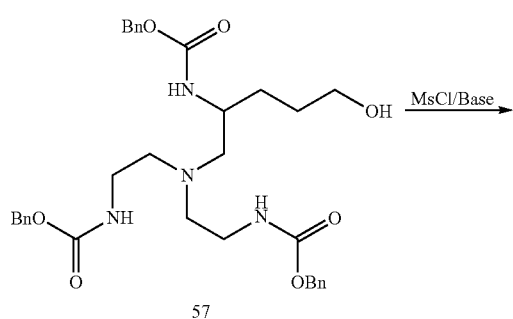

57

102

-continued

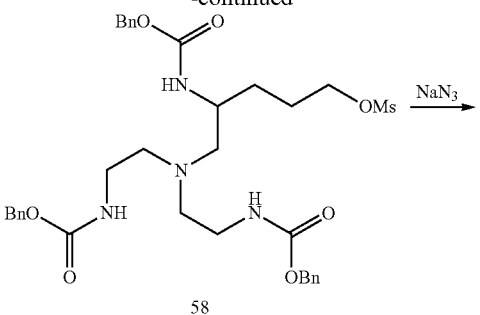

58

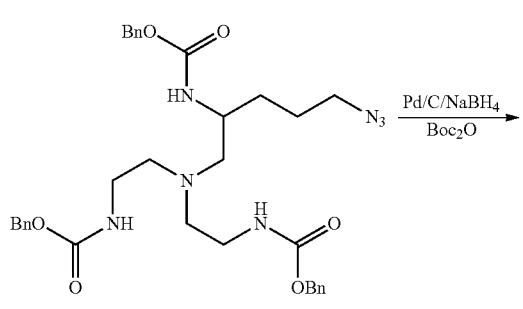

59

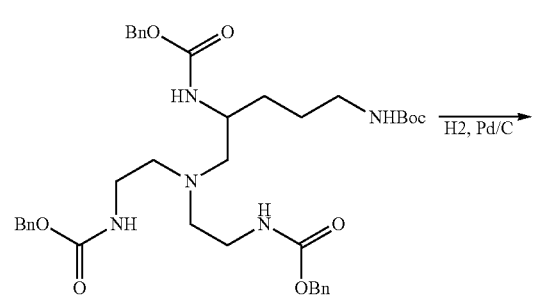

60

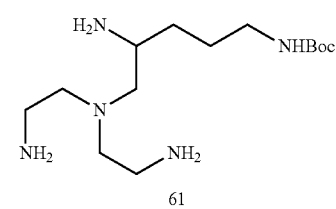

61

Preparation of tris(2-aminoethyl)amine derivative 61 begins with protected glutamic acid derivative 52, which is reduced to alcohol 53. Alcohol 53 is oxidized to aldehyde 54, which is condensed with N,N"-di-benzyloxycarbonyl protected diethylenetriamine to form ester 55. Hydrolysis of ester 55 using base provides carboxylic acid 56, which is reduced to alcohol 57 and then reacted with methanesulfonyl chloride to form sulfonic ester 58. Reaction of sulfonic ester 58 with sodium azide forms azide 59. Reduction of azide 59 using sodium borohydride with a palladium on carbon catalyst forms an intermediate amine that reacts with di-tert-butylpyrocarbonate to produce the fully protected amine 60. Selective removal of benzyloxycarbonyl groups by hydrogenation provides tris(2-aminoethyl)amine derivative 61.

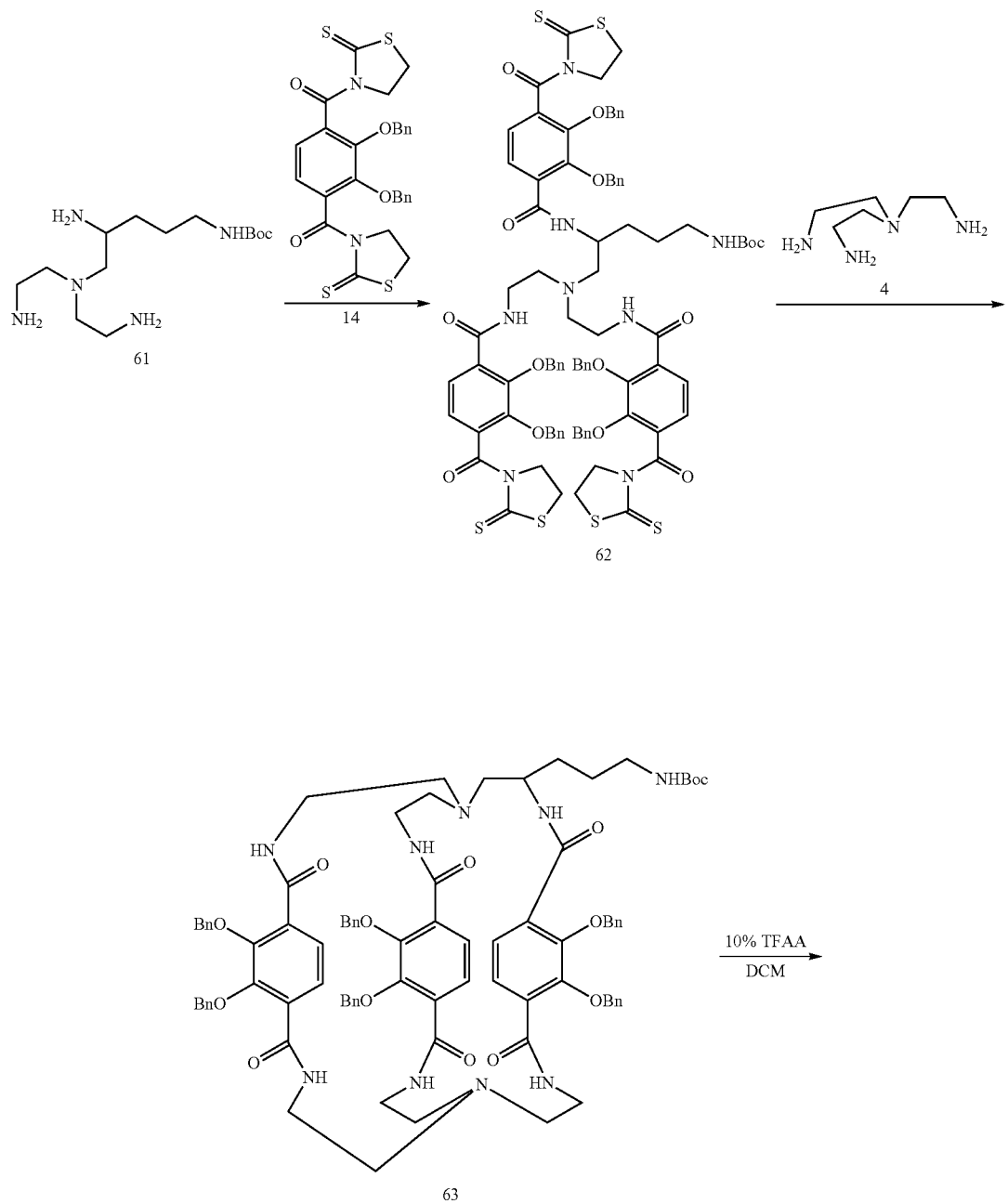

-continued
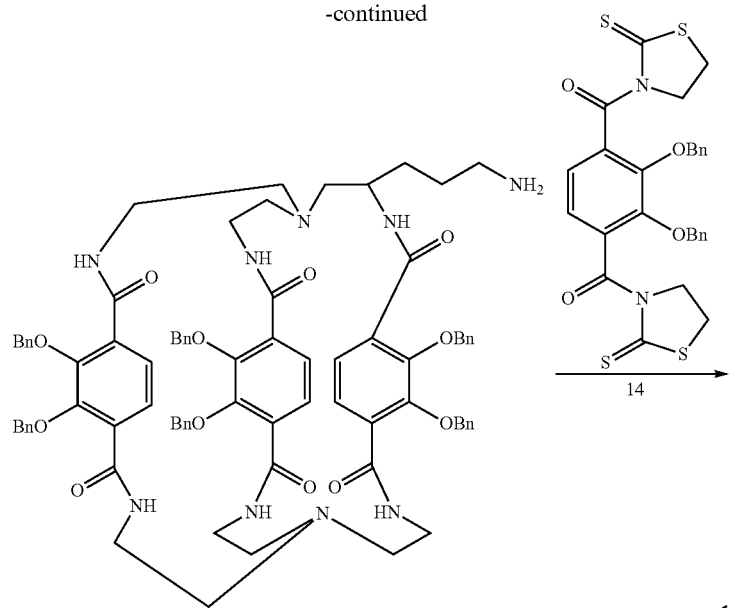
64
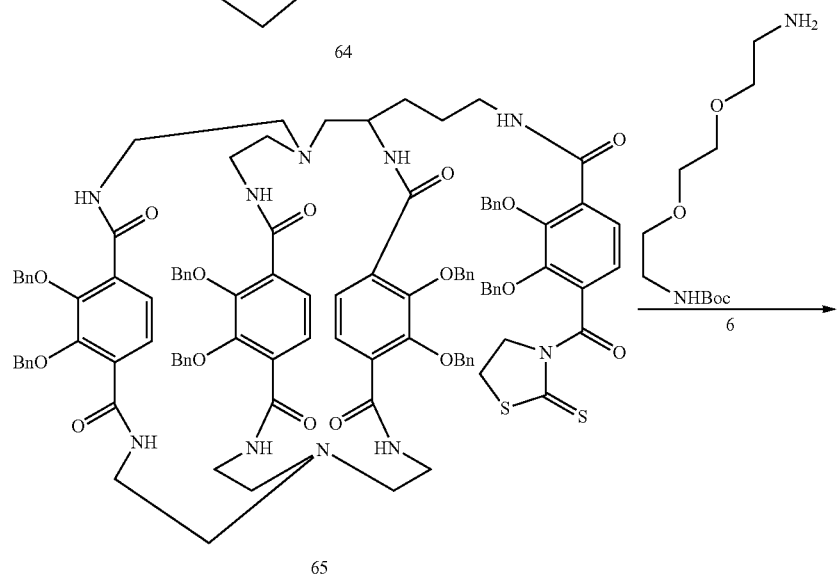
65
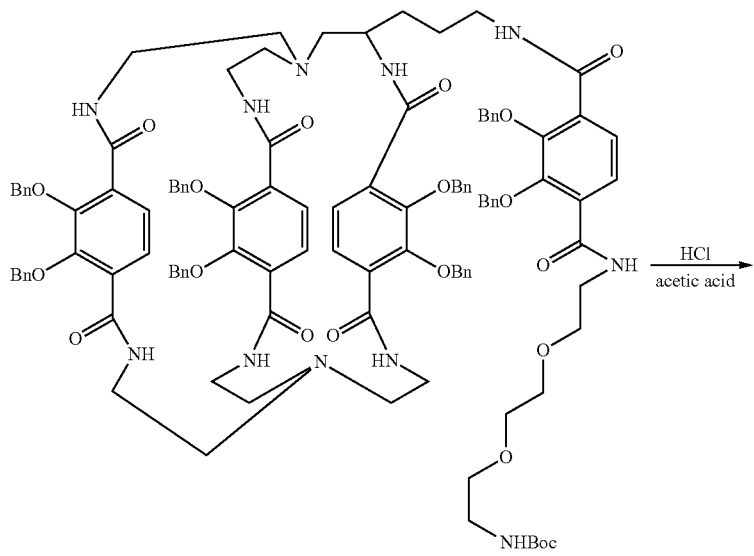
66

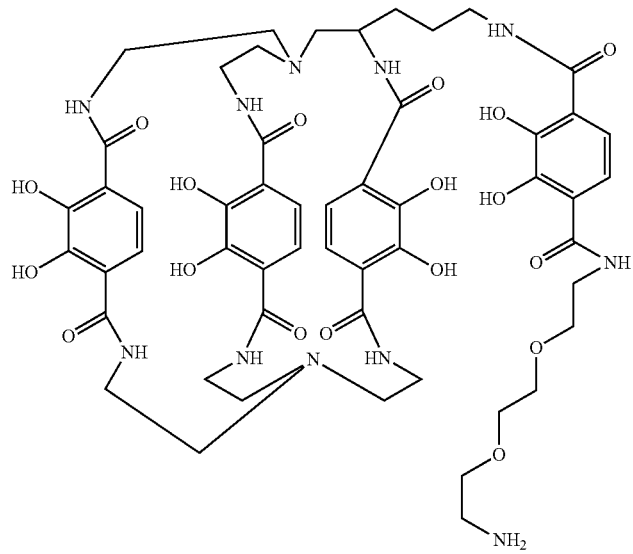

67

Preparation of a terephthalamide (TAM) bi-macrocyclic ligand begins with 2,3-dibenzyloxy-bis(2-mercaptothiazolide)terephthalamide 14, which is condensed with tris-(2-aminoethyl)amine derivative 61 under pseudo-first order conditions to provide the activated tri-amide 62, which is reacted with tris-(2-aminoethyl)amine 4 under high dilution conditions to form the bi-macrocycle 63. The tert-butyloxycarbonyl group is selectively removed using 10% trifluoroacetic acid in dichloromethane to provide the amine 64, which can be reacted with terephthalamide 14 to produce bi-macrocycle 65. The remaining active amide in 65 is reacted with amine 6, and protective groups are removed using a solution of concentrated hydrochloric acid in acetic acid to provide bi-macrocycle 67.

Example 17

Synthesis of a Bi-Macrocyclic Luminescent Sensor (Scheme 18).

Scheme 18. Synthesis of a bi-macrocyclic luminescent sensor. The remainder groups "R" may be any standard amino acid side-chain.

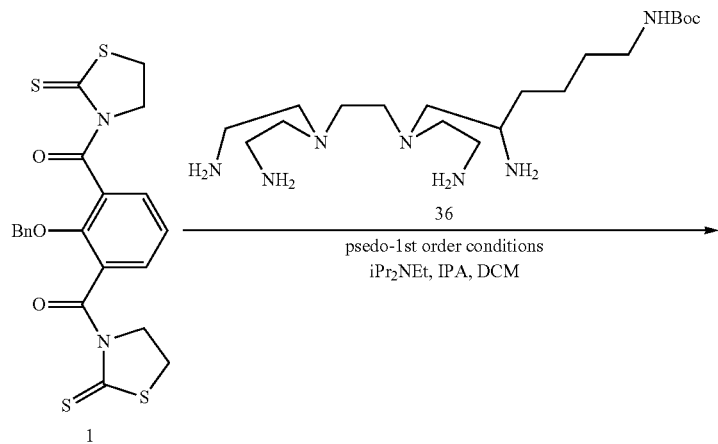

-continued
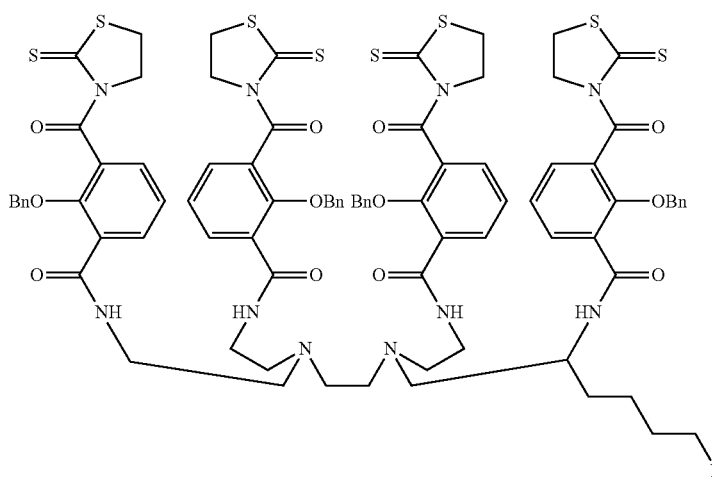
68
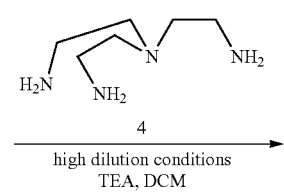
high dilution conditions
TEA, DCM
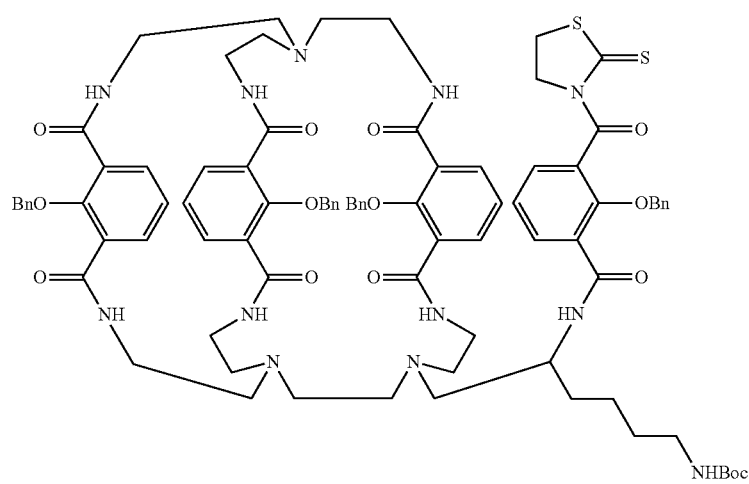
69
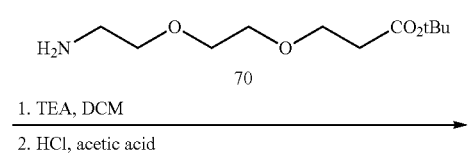
1. TEA, DCM
2. HCl, acetic acid
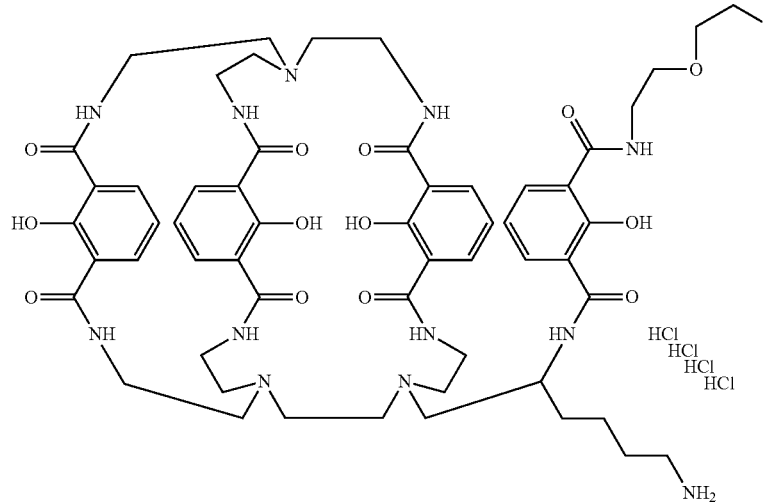
71
Peptide synthesis
high dilution conditions -continued
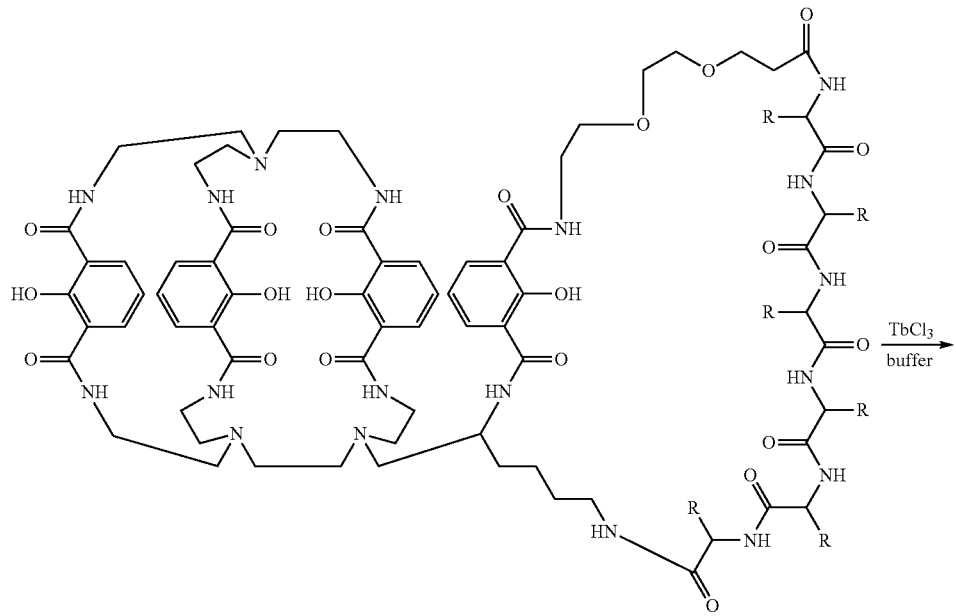
72
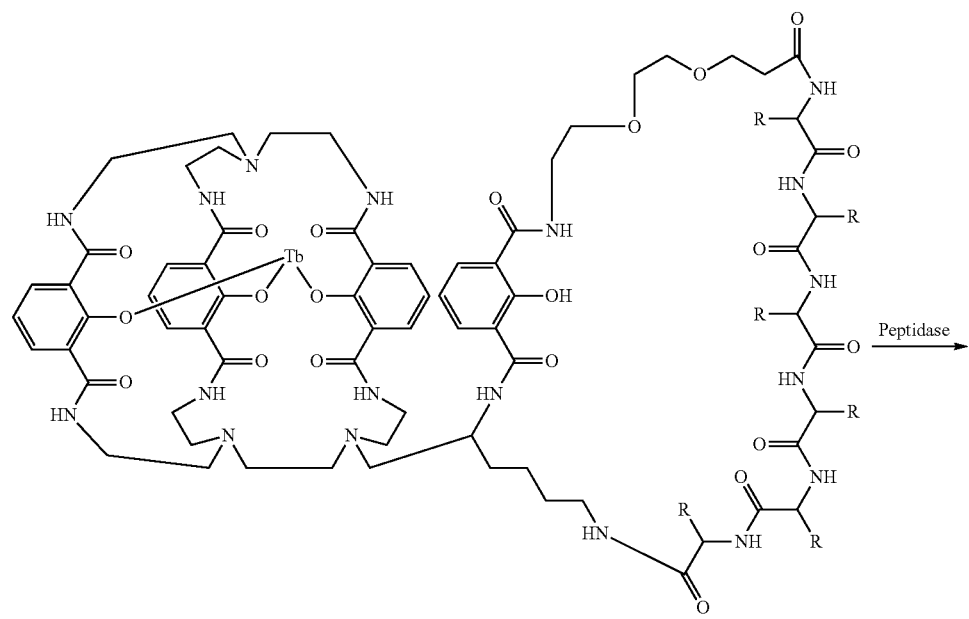
73

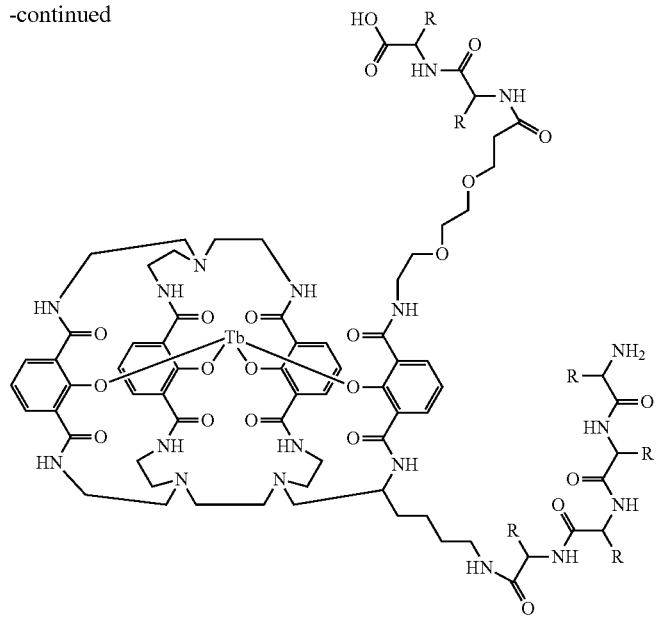

74

Preparation of an isophthalamide (IAM) bi-macrocyclic luminescent sensor begins with 2-benzyloxy-1,3-phenylenebis((2-thioxothiazolidin-3-yl)methanone) 1, which is condensed with (S)-tert-butyl-5-amino-6-((2-aminoethyl)(2-(bis(2-aminoethyl)amino)ethyl)amino)hexylcarbamate 36 under pseudo-first order conditions to provide the activated tetra-amide 68, which is reacted with tris-(2-aminoethyl)amine 4 under high dilution conditions to form the bi-macrocycle 69. The remaining activated amide in 69 is reacted with amine 70 to provide a bi-macrocyclic intermediate from which groups are removed using a solution of concentrated hydrochloric acid in acetic acid to provide bi-macrocycle 71. Conjugation of 71 with a short (e.g., six residues) peptide using standard techniques followed by cyclization under high dilution conditions using an appropriate (e.g., TBTU) condensation reagent provides tri-macrocycle 72. Treatment of 72 with terbium chloride in buffer (e.g., TRIS buffered saline) at neutral pH leads to formation of the corresponding terbium complex 73. Due to the conformational restriction of the peptide containing macrocyclic ring, the isophthalamide moiety also present in this ring is unable to coordinate terbium. The terbium atom in complex 73 as a consequence displays a short lifetime due to coordination by water and is poorly luminescent. Cleavage of the peptide moiety present in complex 73 breaks this macrocyclic ring, allowing the isophthalamide moiety sufficient conformational mobility to coordinate to the terbium atom in the bi-macrocyclic cleavage product 74. Bi-macrocycle 74 is therefore highly luminescent. The terbium complex 73 may therefore find use as a reagent for luminescent detection of enzymatic activities that cleave the peptide containing ring. One skilled in the art would be able to modify the synthesis of terbium complexes such as 73 to contain many different peptide sequences in order to assay various enzymatic activities of interest.

Example 18

Synthesis of an Octa-Coordinating Bi-Macrocyclic Bifunctional Chelator (Scheme 19).

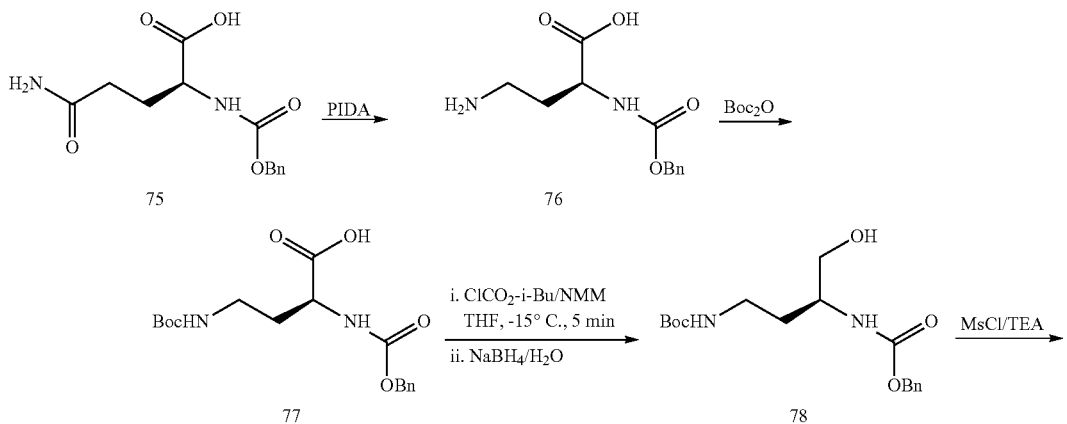

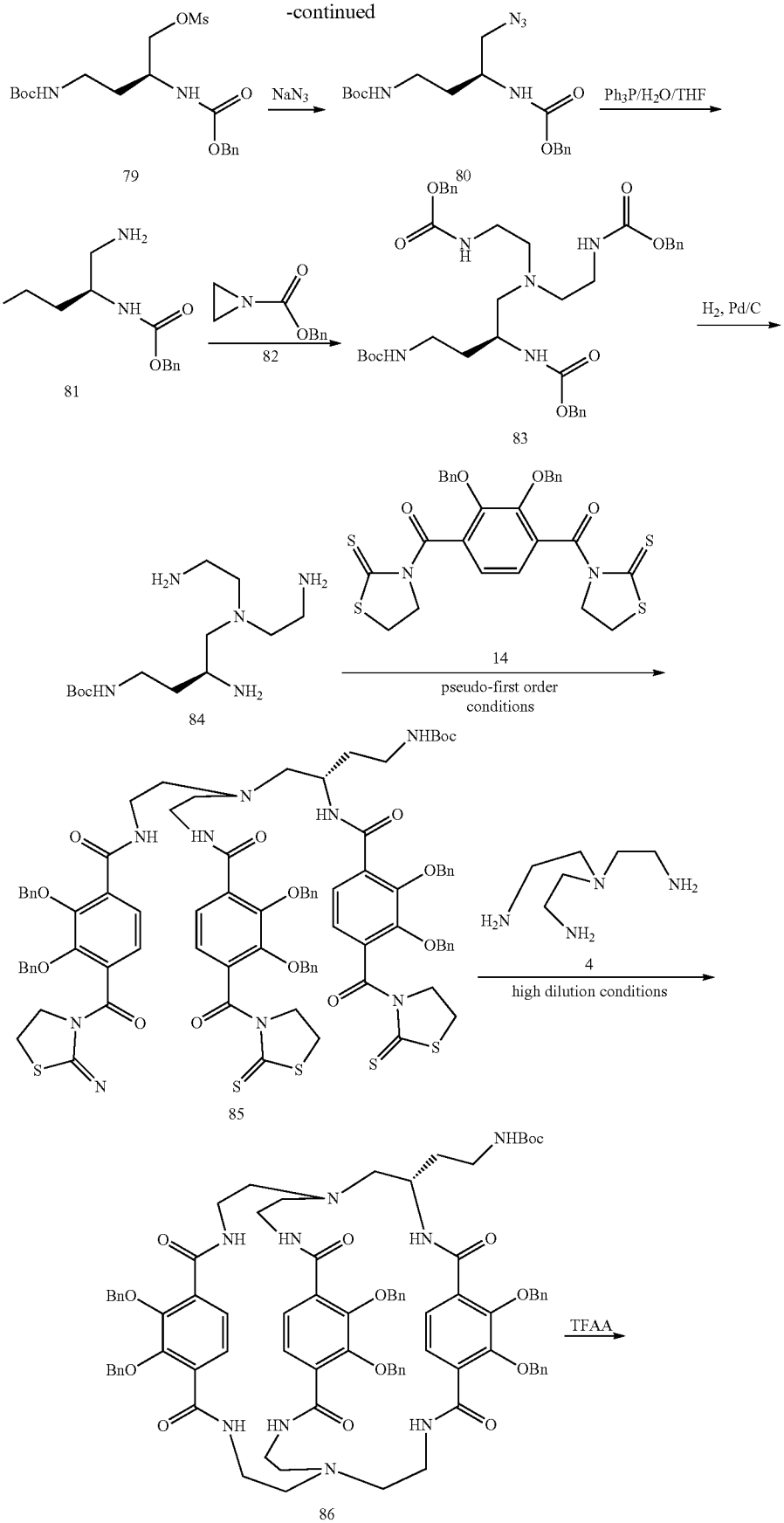

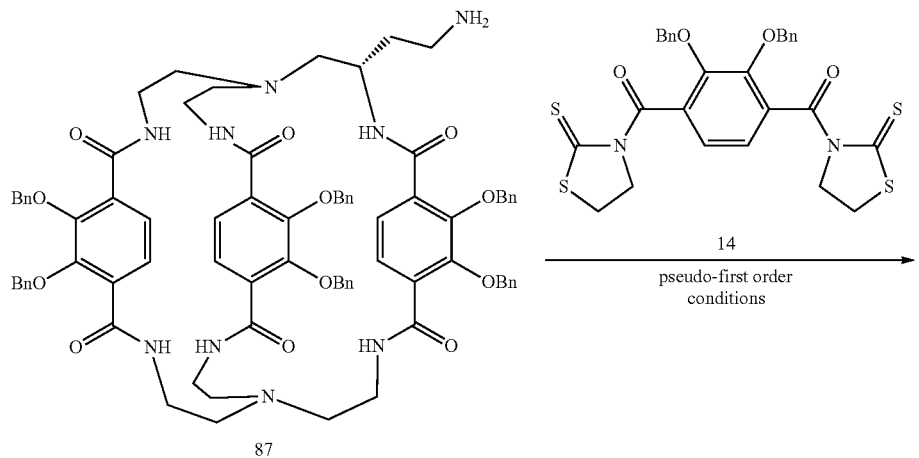
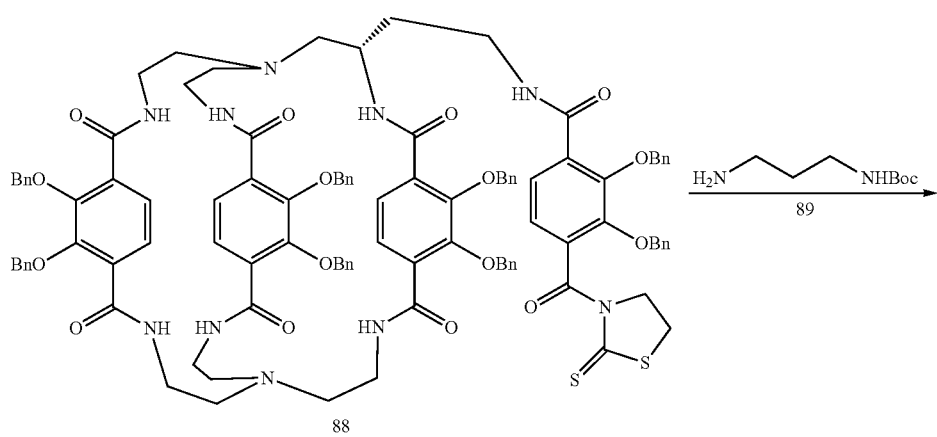
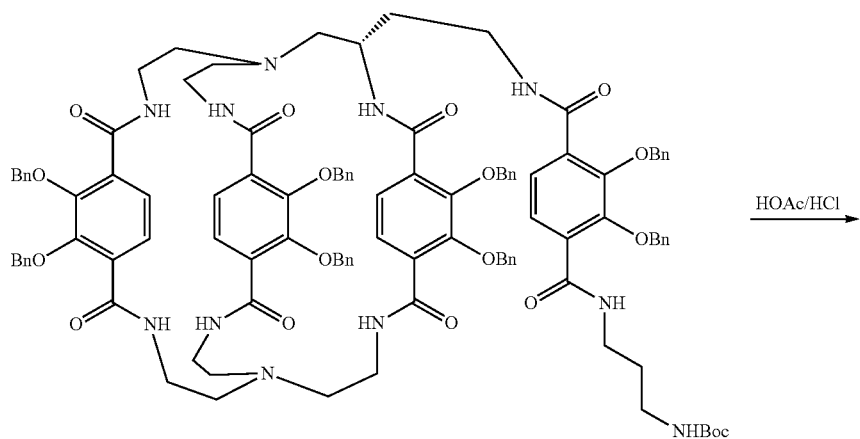

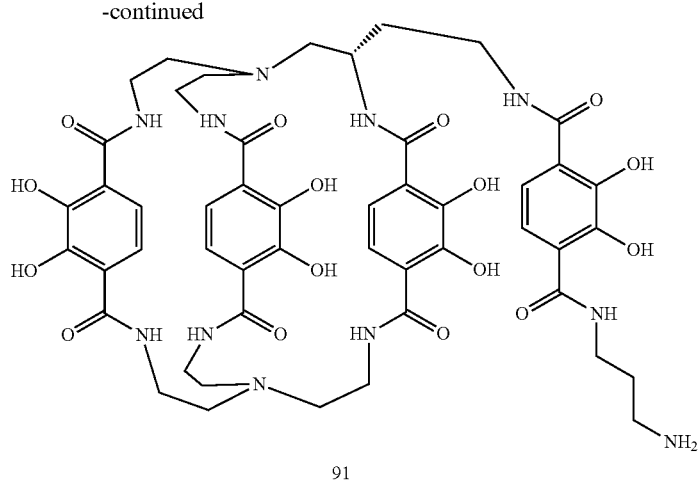

91

Preparation of a terephthalamide (TAM) bi-macrocyclic ligand begins with glutamine derivative 75, which is reacted with phenyliodonium diacetate (PIDA) to form aminoacid 76. Reaction with di-tert-butylpyrocarbonate provides the carboxylic acid 77. Acid 77 is reacted with isobutyryl chloroformate in the presence of N-methylmorpholine (NMM) and the mixed anhydride intermediate is reduced using sodium borohydride to provide alcohol 78. Alcohol 78 is reacted with methanesulfonyl chloride to form sulfonic ester 79. Reaction of sulfonic ester 79 with sodium azide forms azide 80. Reduction of azide 80 using triphenylphosphine forms amine 81 that is reacted with aziridine 82 to produce the fully protected amine 83. Selective removal of benzyloxycarbonyl groups by hydrogenation provides tris (2-aminoethyl)amine derivative 84. 2,3-Dibenzyloxy-bis(2-mercaptothiazolide)terephthalamide 14 is condensed with tris-(2-aminoethyl)amine derivative 84 under pseudo-first order conditions to provide the activated tri-amide 85, which is reacted with tris-(2-aminoethyl)amine 4 under high dilution conditions to form the bi-macrocycle 86. The tert-butyloxycarbonyl group is selectively removed using 10% trifluoroacetic acid in dichloromethane to provide the amine 87, which can be reacted with terephthalamide 14 to produce bi-macrocycle 88. The remaining active amide in 88 is reacted with amine 89 to form bi-macrocycle 90. Protective groups are removed from bi-macrocycle 90 using a solution of concentrated hydrochloric acid in acetic acid to provide bi-macrocycle 91.

Example 19

Synthesis of an Octa-Coordinating Bi-Macrocyclic Bifunctional Chelator (Schemes 20 and 21).

Scheme 20. Synthesis of tris(2-aminoethyl)amine derivative 100.

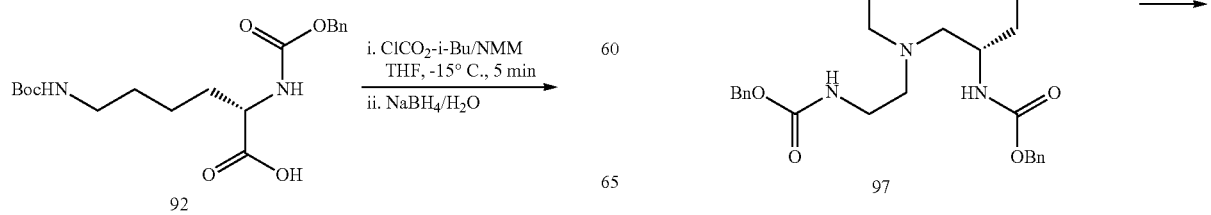

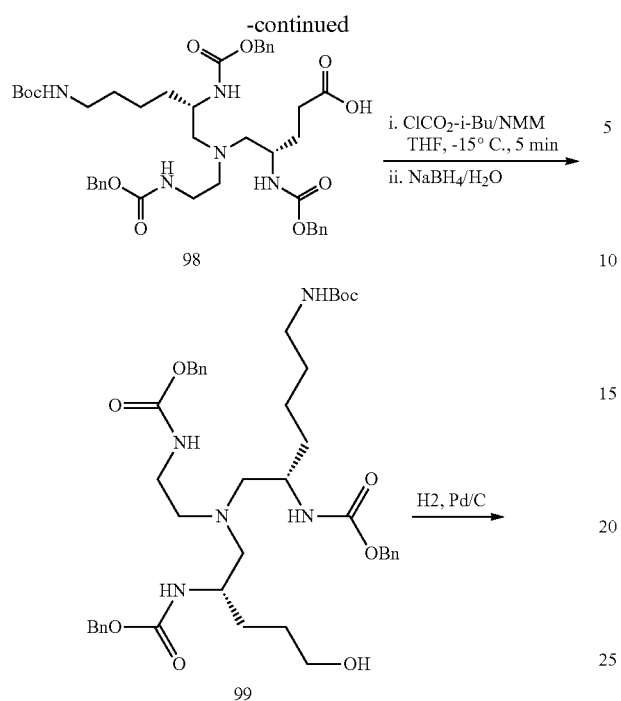

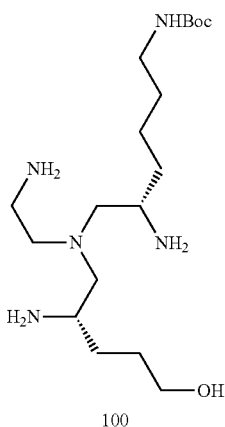

Preparation of tris(2-aminoethyl)amine derivative 100 begins with protected lysine derivative 92, which is reduced to alcohol 93. Alcohol 93 is oxidized to aldehyde 94, which is condensed with N-benzyloxycarbonyl protected ethylenediamine 95 to form amine 96. Condensation of amine 96 with aldehyde 54 produces ester 97. Hydrolysis of ester 97 using base provides carboxylic acid 98, which is reduced to alcohol 99. Selective removal of benzyloxycarbonyl groups by hydrogenation provides tris(2-aminoethyl)amine derivative 100.

Scheme 21. Synthesis of bi-macrocyclic chelator 109.

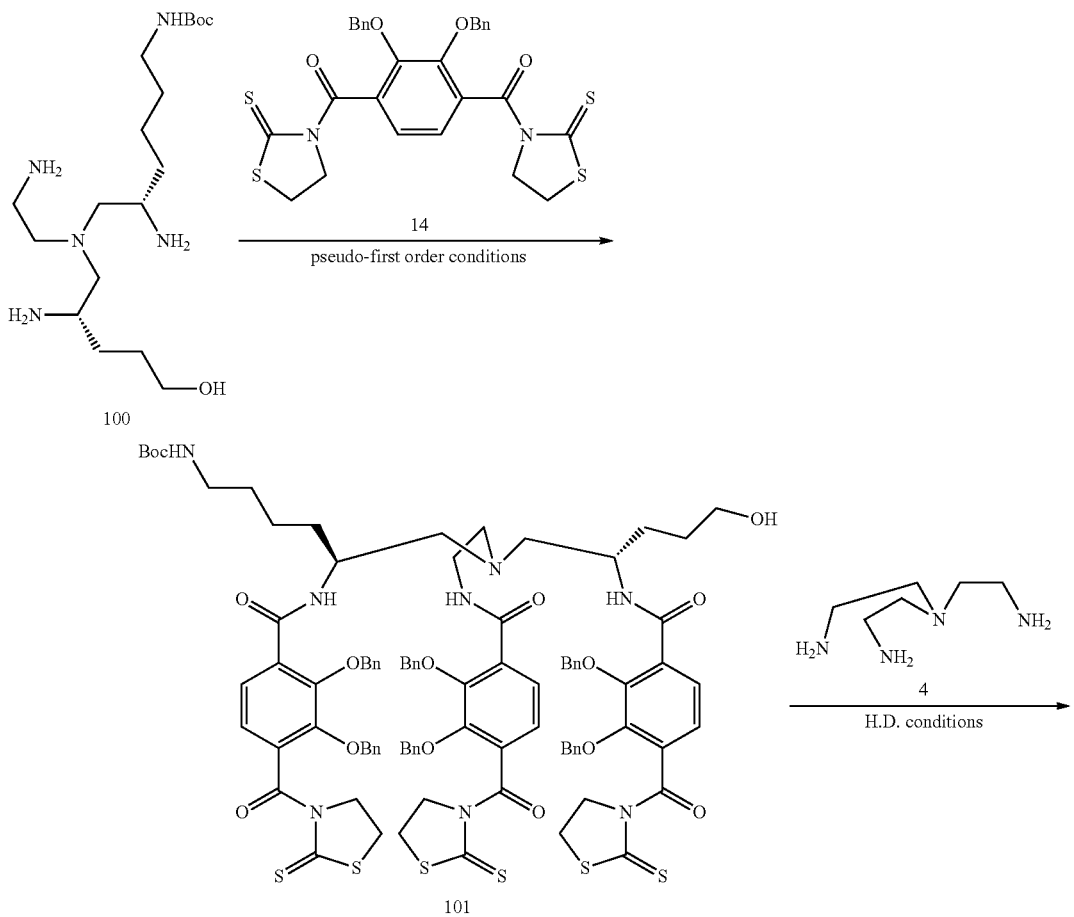

-continued
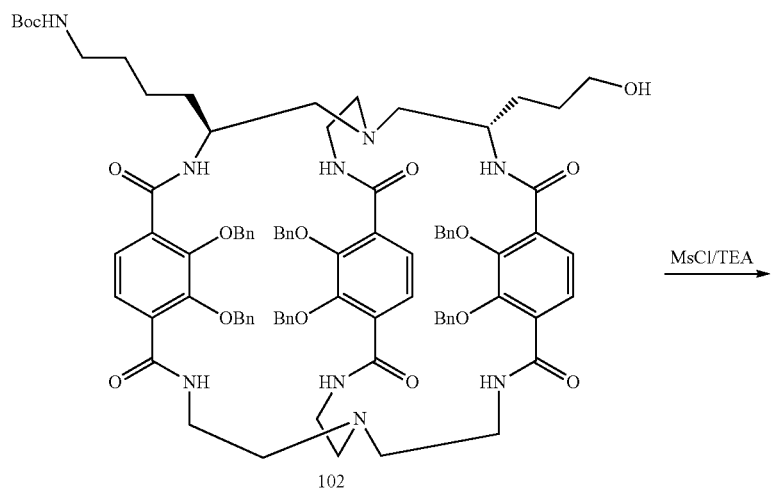
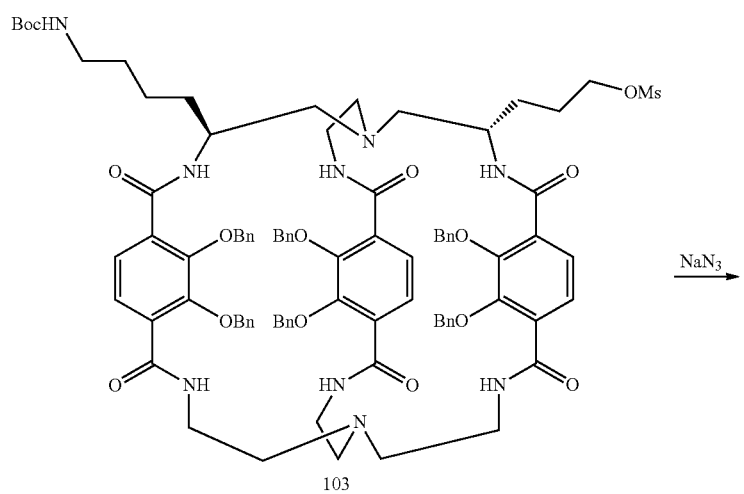
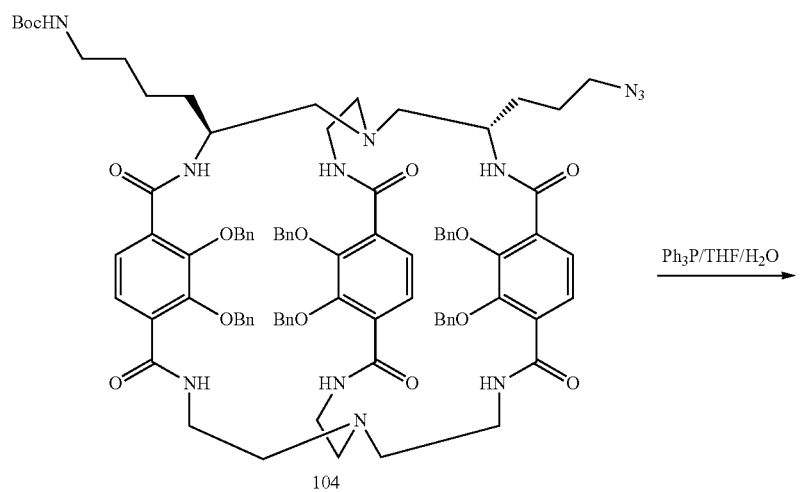

125 126
-continued
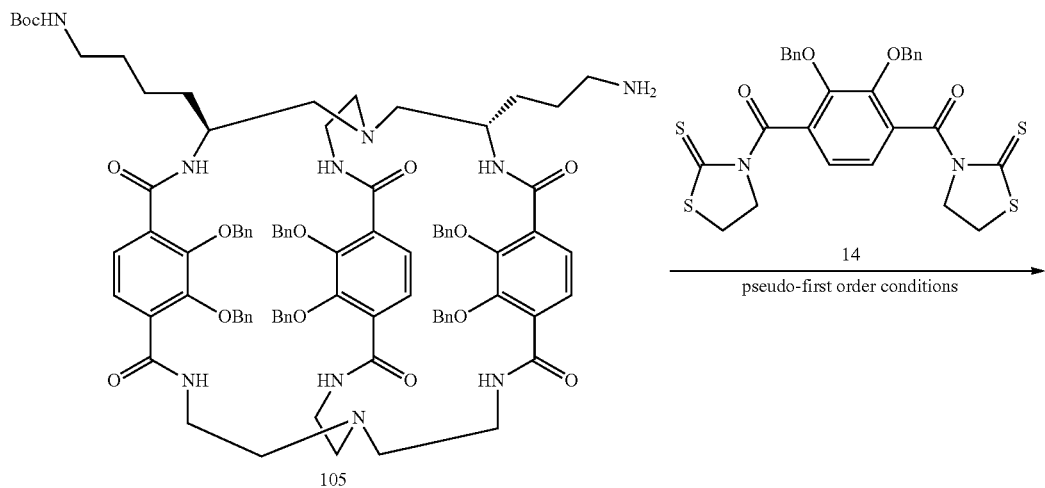
105
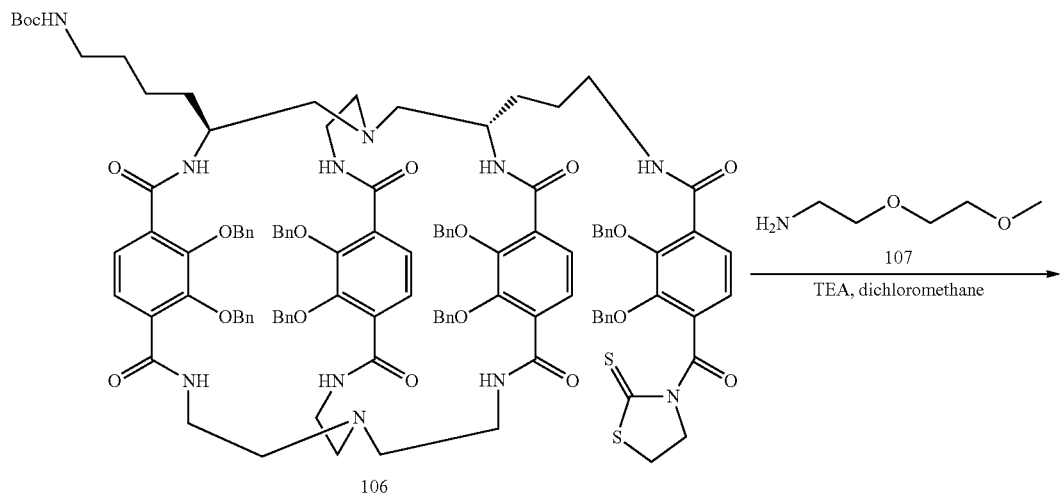
106
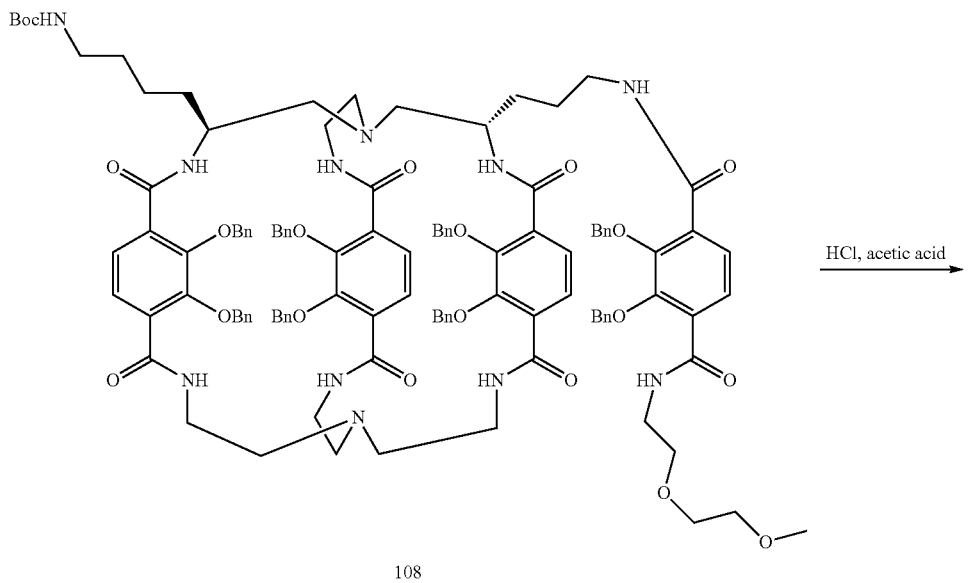
108

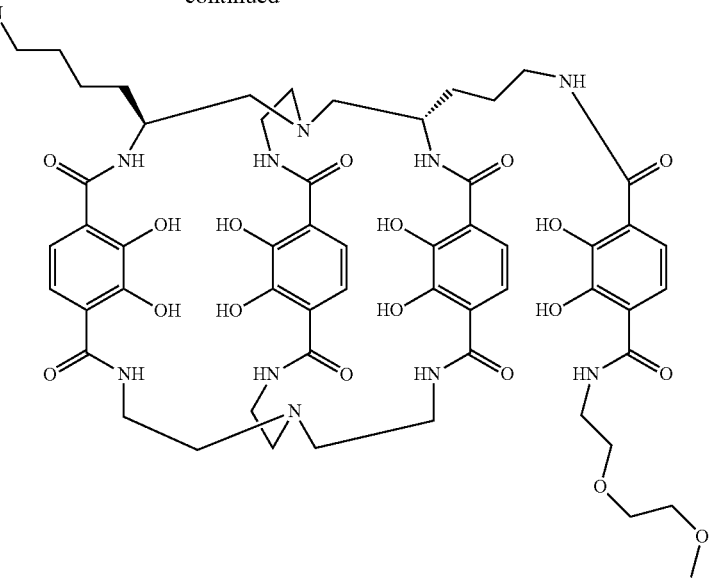

109

Preparation of a terephthalamide (TAM) bi-macrocyclic ligand begins with 2,3-dibenzyloxy-bis(2-mercaptothiazolide)terephthalamide 14, which is condensed with tris-(2-aminoethyl)amine derivative 100 under pseudo-first order conditions to provide the activated tri-amide 101, which is reacted with tris-(2-aminoethyl)amine 4 under high dilution conditions to form the bi-macrocycle 102. The alcohol group on bi-macrocycle 102 is reacted with methanesulfonyl chloride to form the sulfonyl ester 103. Sulfonyl ester 103 is treated with sodium azide in dimethylformamide to form azide 104. Reduction of azide 104 with triphenylphosphine yields amine 105. Amine 105 can be reacted with terephthalamide 14 to produce bi-macrocycle 106. The remaining active amide in 106 is reacted with amine 107 forming bi-macrocycle 108. Protective groups are removed from bi-macrocycle 108 using a solution of concentrated hydrochloric acid in acetic acid to provide bi-macrocycle 109.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A macrocycle having a structure:

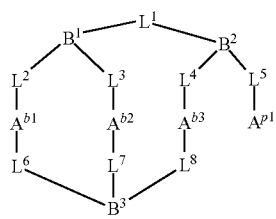

wherein
B$^1$, B$^2$, and B$^3$ are N;

L$^1$, L$^2$, L$^3$, L$^4$, L$^5$, L$^6$, L$^7$, and L$^8$ are independently selected from substituted or unsubstituted alkyl and substituted or unsubstituted heteroalkyl;

A$^{b1}$, A$^{b2}$, A$^{b3}$, and A$^{p1}$ are, respectively

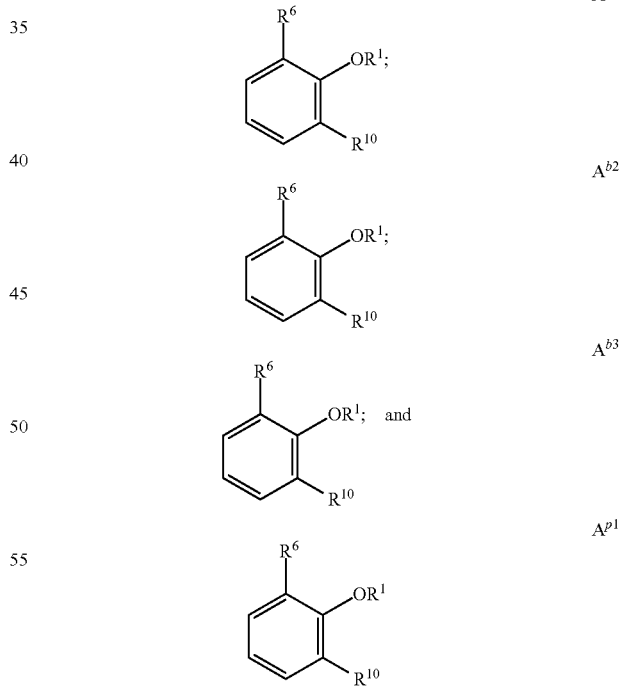

wherein
R$^1$ is a member selected from H and a negative charge;
R$^6$ of (A$^{b1}$) is a bond to L$^2$; and R$^{10}$ of (A$^{b1}$) is a bond to L$^6$;
R$^6$ of (A$^{b2}$) is a bond to L$^3$; and R$^{10}$ of (A$^{b2}$) is a bond to L$^7$;

$R^6$ of ($A^{b3}$) is a bond to $L^4$; and $R^{10}$ of ($A^{b3}$) is a bond to $L^8$;

$R^6$ of ($A^{p1}$) is a bond to $L^5$; and $R^{10}$ of ($A^{p1}$) is a bond to $L^{11}$-X wherein $L^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

and X is a reactive functional group or a targeting moiety.

2. The macrocycle according to claim 1, wherein $L^{11}$ is substituted or unsubstituted heteroalkyl.

3. The macrocycle according to claim 1, wherein $L^{11}$-X is $C(O)NR^{17}R^{18}$, wherein $R^{17}$ is H and $R^{18}$ is a modifying moiety selected from an oligonucleotide, a substituted or unsubstituted polyether, and a peptide.

4. The macrocycle according to claim 3, wherein oligonucleotide is a member selected from ssDNA, dsDNA, and RNA.

5. The macrocycle according to claim 3, wherein the peptide is an antibody.

6. The macrocycle according to claim 3, wherein the peptide is an antibody fragment.

7. The macrocycle according to claim 1, wherein $L^{11}$ is a member selected from:

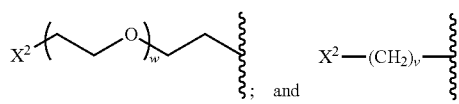

wherein w is an integer from 1 to 1,000;
v is an integer from 1 to 20; and
$X^2$ is a member selected from:

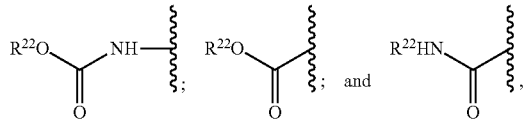

wherein $R^{22}$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

8. The macrocycle according to claim 7, wherein w is an integer from 1 to 10.

9. The macrocycle according to claim 1, wherein $L^{11}$ is $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ and $C_{20}$ alkyl in which 1, 2 or 3 atoms are replaced with a heteroatom selected from nitrogen and oxygen.

10. The macrocycle according to claim 1, wherein $L^{11}$ is a 5-member $C_4$ heteroalkyl moiety with one oxygen atom.

11. The macrocycle according to claim 1, wherein $L^{11}$-X is a member selected from:

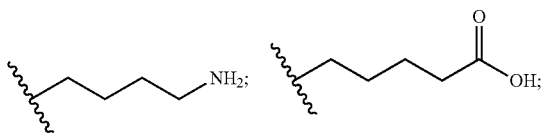

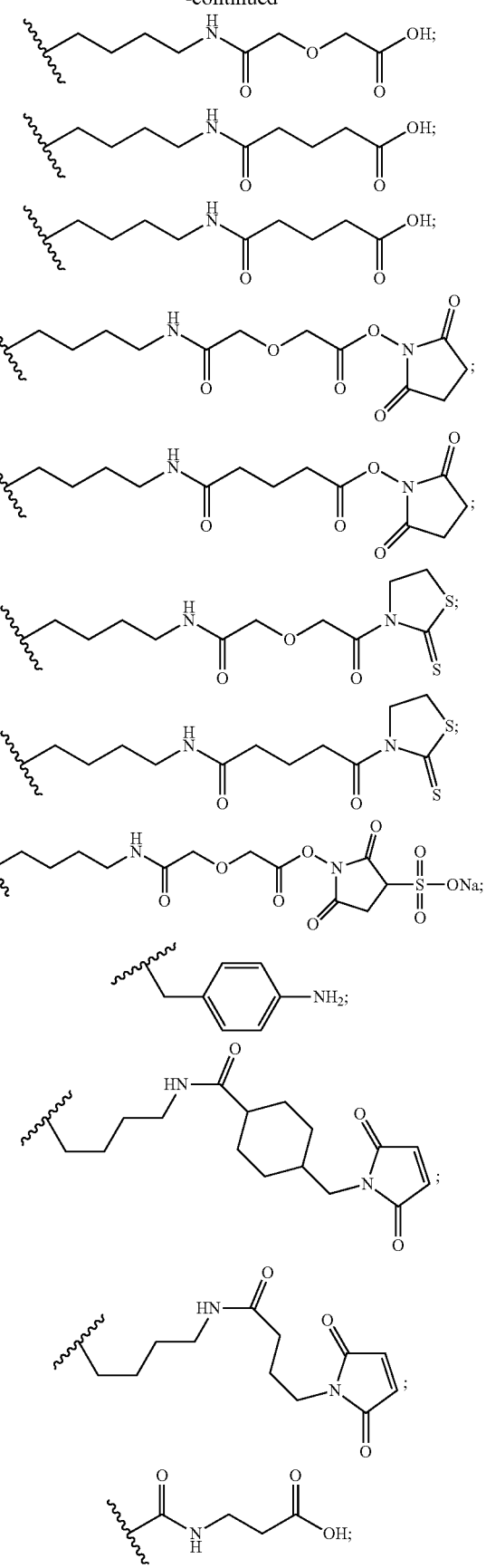

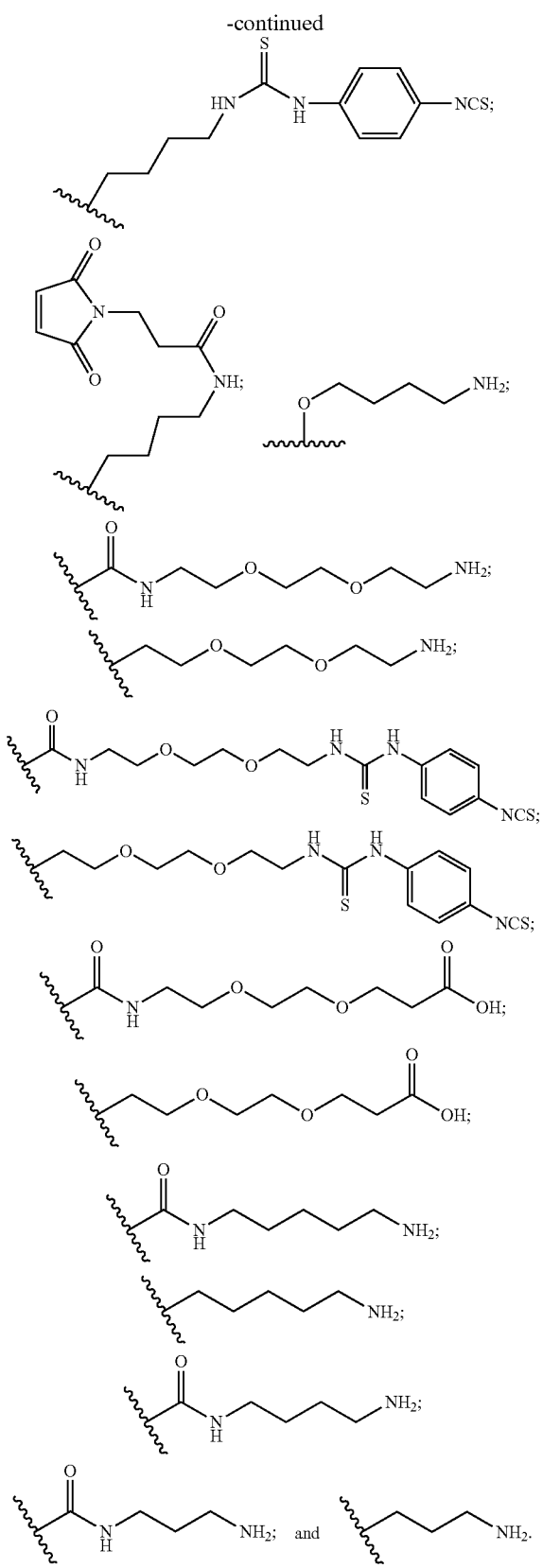

12. The macrocycle according to claim 1, wherein the targeting moiety is a member selected from a peptide, a polypeptide, a nucleic acid, an oligonucleotide, a carbohydrate, polysaccharide, a lipid, a hormone, a growth factor, a lectin, a receptor, a receptor ligand, and a cofactor.

13. The macrocycle according to claim 12, wherein the targeting moiety is a member selected from an antibody and an antibody fragment.

14. The macrocycle according to claim 1, wherein the reactive functional group is a member selected from olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso groups.

15. The macrocycle according to claim 14, wherein the reactive functional group is a member selected from a N-hydroxysuccinimide (NHS) ester, a sulfo-NHS ester, an imidoester, an isocyanate, an isothiocyanate, an acylhalide, an arylazide, a p-nitrophenyl ester, an aldehyde, a sulfonyl chloride, a thiazolide and a carboxyl group.

16. The macrocycle according to claim 14, wherein the reactive functional group is $NH_2$ or COOH.

17. The macrocycle according to claim 1, having the structure:

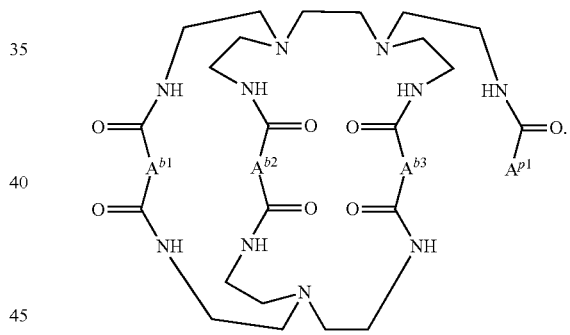

18. A complex comprising a macrocycle according to claim 1 and a metal ion.

19. The complex according to claim 18, wherein the metal is selected from a lanthanide, an actinide, yttrium (Y), and zirconium (Zr).

20. The complex according to claim 19, wherein the lanthanide is selected from terbium (Tb), europium (Eu), dysprosium (Dy), and lutetium (Lu).

21. The complex according to claim 19, wherein said actinide is thorium (Th).

22. The complex according to claim 18, wherein said metal is a radionuclide.

23. The complex according to claim 22, wherein said metal ion is $^{227}$Th(IV) or $^{89}$Zr(IV).

24. The complex according to claim 18, wherein said complex is a luminescent complex.

* * * * *